US008178683B2

(12) United States Patent
Gordeev

(10) Patent No.: US 8,178,683 B2
(45) Date of Patent: May 15, 2012

(54) ANTIMICROBIAL ORTHO-FLUOROPHENYL OXAZOLIDINONES FOR TREATMENT OF BACTERIAL INFECTIONS

(75) Inventor: Mikhail Fedorovich Gordeev, Castro Valley, CA (US)

(73) Assignee: Micurx Pharmaceuticals, Inc., George Town, Grand Cayman (KY)

( * ) Notice: Subject to any disclaimer, the term of this patent is extended or adjusted under 35 U.S.C. 154(b) by 452 days.

(21) Appl. No.: 12/187,302

(22) Filed: Aug. 6, 2008

(65) Prior Publication Data

US 2009/0048305 A1    Feb. 19, 2009

Related U.S. Application Data

(60) Provisional application No. 60/963,811, filed on Aug. 6, 2007.

(51) Int. Cl.
*C07D 413/14* (2006.01)
*A61K 31/4439* (2006.01)

(52) U.S. Cl. .................. 546/271.4; 546/268.4; 514/340
(58) Field of Classification Search ............ 546/271.4, 546/268.4; 514/340
See application file for complete search history.

(56) References Cited

U.S. PATENT DOCUMENTS

| | | | | |
|---|---|---|---|---|
| 5,668,286 A * | 9/1997 | Yamada et al. | ............... | 546/209 |
| 6,919,329 B2 * | 7/2005 | Thomas et al. | .......... | 514/217.01 |
| 7,105,547 B2 * | 9/2006 | Gordeev et al. | ............... | 514/340 |
| 7,141,588 B2 * | 11/2006 | Thomas et al. | ............... | 514/342 |

FOREIGN PATENT DOCUMENTS

| | | |
|---|---|---|
| WO | WO 03/006440 | 1/2003 |
| WO | WO 03072553 A1 * | 9/2003 |
| WO | WO 2004/059120 | 3/2004 |
| WO | WO 2004033449 A1 * | 4/2004 |
| WO | WO 2004/087697 | 10/2004 |
| WO | WO 2005/019213 A1 | 3/2005 |
| WO | WO 2005/113520 | 12/2005 |
| WO | WO 2006/038100 | 4/2006 |
| WO | WO 2007/000644 | 1/2007 |
| WO | WO 2007/004049 | 1/2007 |

OTHER PUBLICATIONS

Patani et. al. "Bioisosterism: A Rational Approach in Drug Design" Chemical Reviews 1996, 96, 3147-3176.*
Wakefield, Basil "Fluorinated Pharmaceuticals" Innovations in Pharmaceutical Technology 2000, 74, 76-78.*
Sawhney, S. K. and Singh, R. "Introductory Practical Biochemistry" Narosa: New Delhi, 2002, pp. 2-3.*
Humphrey et. al. "Cardiovascular Sympathomimetic Amine Interactions in Rats Treated with Monoamine Oxidase Inhibitors and the Novel Oxazolidinone Antibiotic Linezolid" Journal of Cardiovascular Pharmacology 2001, 37:548-563.*
PCT International Search Report dated Nov. 27, 2008, for International Application No. PCT/US2008/009441, filed Aug. 6, 2008.
PCT International Written Opinion dated Nov. 27, 2008, for International Application No. PCT/US2008/009441, filed Aug. 6, 2008.
PCT International Preliminary Report on Patentability dated Feb. 18, 2010, for International Application No. PCT/US2008/009441, filed Aug. 6, 2008.
Hutchinson D.K., "Oxazolidinone Antibacterial Agents: A Critical Review", 2003, *Current Topics in Medicinal Chemistry*, 3:1021-1042.
Jones et al., "Zyvox® Annual Appraisal of Potency and Spectrum program: linezolid surveillance program results for 2008", 2009, *Diagnostic Microbiology and Infectious Disease*, 65:404-413.
Mutnick et al., "Spectrum and potency evaluation of a new oxazolidinone, linezolid: report from the SENTRY Antimicrobial Surveillance Program, 1998-2000", 2002, *Diagnostic Microbiology and Infectious Disease*, 43:65-73.
Park et al., "Antibacterials. Synthesis and Structure—Activity Studies of 3-Aryl-2-oxooxazolidines. 4. Multiply-Substituted Aryl Derivatives", 1992, *J. Med. Chem.*, 35:1156-1165.
Prescribing Information for Zyvox, Jun. 2010, Pfizer LAB-0139-20.0, retrieved from U.S. Food & Drug Administration website.
Prescribing Information for Zyvox, Mar. 2007, Pfizer LAB-0139-16.0, retrieved from U.S. Food & Drug Administration website.
Renslo A.R., "Antibacterial oxazolidinones: emerging structure—toxicity relationships", 2010, *Expert Rev. Anti Infect. Ther.* 8(5):565-574.
Vinh et al., "Linezolid: a review of safety and tolerability", 2009, *Journal of Infection*, 59(S1):S59-S74.

* cited by examiner

*Primary Examiner* — David K O Dell
(74) *Attorney, Agent, or Firm* — Squire Sanders (US) LLP

(57) ABSTRACT

The present invention provides certain ortho-fluorophenyl oxazolidinones of the following formula I:

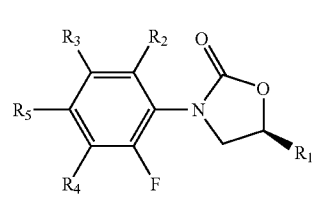

or pharmaceutically acceptable salts or prodrugs thereof that are antibacterial agents, pharmaceutical compositions containing them, methods for their use, and methods for preparing these compounds.

7 Claims, No Drawings

ANTIMICROBIAL ORTHO-FLUOROPHENYL OXAZOLIDINONES FOR TREATMENT OF BACTERIAL INFECTIONS

CROSS REFERENCE TO RELATED APPLICATIONS

The present application claims the benefit of priority of U.S. Provisional Application No. 60/963,811, filed Aug. 6, 2007, the content of which is hereby incorporated by reference in its entirety.

FIELD OF THE INVENTION

The present invention provides novel ortho-fluorophenyl derivatives of oxazolidinones, pharmaceutical compositions thereof, methods for their use, and methods for preparing of the same. These compounds have potent activities against pathogenic bacterial species.

BACKGROUND OF THE INVENTION

Due to an increasing antibiotic resistance, novel classes of antibacterial compounds with a new mode of action are acutely needed for the treatment of bacterial infections. The antibacterials should possess useful levels of activity against certain human and veterinary pathogens, including gram-positive aerobic bacteria such as multiply-resistant staphylococci and streptococci, select anaerobes such as bacteroides and clostridia species, and acid-fast microorganisms such as *Mycobacterium tuberculosis* and *Mycobacterium avium*.

It is also important that such antibacterial agents should offer sufficient safety with a minimal toxicity and adverse effects that can preclude or limit the therapy.

Among newer antibacterial agents, oxazolidinone compounds are the most recent synthetic class of antimicrobials active against a number of pathogenic microorganisms. To date, a sole antibacterial of this class linezolid (Zyvox®) has been approved for a treatment of select gram-positive infections. While oxazolidinones represented by this drug are useful for the treatment of microbial infections, their utility is limited due to serious adverse effects. Among these, monoamine oxidase inhibition and myelosuppression or bone marrow toxicity are among key factors limiting linezolid utility, as reflected in warnings in the drug's prescribing information for Zyvox® The latter type of the oxazolidinone toxicity manifested in a bone marrow suppression (also referred to as hematopoietic toxicity or myelosuppression) was reported, for example, by Monson et al. in Clinical Infectious Diseases, 2002, vol. 35, pp. e29-31. Several adverse effects for Zyvox® (including anemia, leukopenia, pancytopenia, and thrombocytopenia) have been ascribed to this phenomenon.

None of aforementioned publications specifically contemplates compounds of the present invention, their beneficial safety profiles, their combination therapies, or their novel compositions.

SUMMARY OF THE INVENTION

The present invention provides novel pharmaceutical ortho-fluorophenyl oxazolidinone compounds with useful antibacterial activity. The term ortho-fluorophenyl indicates the presence of the mandatory F substituent in a position 2 of a respective phenyl oxazolidinone, i.e. F at the phenyl group site adjacent to the oxazolidinone ring nitrogen. The activity for compounds of this invention includes antibacterial activity against gram-positive microorganisms, such as *Staphylococcus aureus*, *Streptococcus pneumoniae*, *Enterococcus faecalis*, and *Enterococcus faecium*. Within the scope of the invention, uniquely constructed ortho-fluorophenyl oxazolidinones incorporating select unsaturated heterocyclic rings (placed at the para- or 4-position of a phenyl group) provide therapeutically useful compounds with beneficial activity and safety profile.

Surprisingly, compounds of the present invention can combine high antibacterial activity with reduced monoamine oxidase inhibition. Furthermore, ortho-fluorophenyl oxazolidinones of the present invention can offer a beneficially reduced myelosuppression. The compounds provided herein are useful as antibacterial agents for treatment of infections including, but not limited to, skin infections, soft tissue infections, bacteremia, respiratory tract infections, urinary tract infections, bone infections, and eye infections.

The present invention provides a compound of the following formula I:

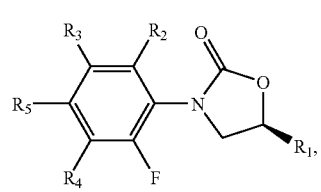

or a pharmaceutically acceptable salt or prodrug thereof wherein:

$R^1$ is $CH_2NHC(=O)R^6$, $CONHR^6$, $CHR^6OH$, $CH_2NHC(=S)R^6$, $CH_2NHC(=NCN)R^6$, $CH_2NH\text{-}Het^1$, $CH_2O\text{-}Het^1$, $CH_2S\text{-}Het^1$, $Het^2$, $CN$; and wherein $R^6$ is H, $NH_2$, $NHC_{1-4}alkyl$, $C_{1-4}alkyl$, $C_{3-6}cycloalkyl$, $C_{2-4}alkenyl$, $C_{2-4}alkynyl$, $C_{1-4}heteroalkyl$, $Het^1$, $Het^2$, $(CH_2)_mC(=O)C_{1-4}alkyl$, $OC_{1-4}alkyl$, $SC_{1-4}alkyl$, $(CH_2)_pC_{3-6}cycloalkyl$, $(CH_2)_mC(=O)\text{-}aryl$, or $(CH_2)_mC(=O)\text{-}Het^1$; and $R^2$ is H or F; and $R^3$ and $R^4$ are independently H, F, Cl, CN, or OH; and $R^3$ is $CONHR^6$, $C_{3-6}cycloalkyl$, aryl, biaryl, $Het^1$, $Het^2$, 4 to 7-membered heterocyclic group; and wherein m is 0, 1, or 2;

and with a proviso excluding embodiments wherein $R^1$ is $CH_2NHC(=O)R^6$, wherein $R^6$ is $C_{1-6}alkyl$, $OC_{1-4}alkyl$, or $NHC_{1-6}alkyl$; and $R^2$ is H; and $R^3$ and $R^4$ are both F; and $R^5$ is

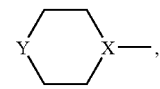

wherein X is CH or N; and Y is O or $S(O)_n$; or X is N and Y is $HOCH_2(C=O)N$; and n is 0, 1, or 2.

The alkyl, alkenyl, or cycloalkyl groups at each occurrence above independently are optionally substituted with one, two, or three substituents selected from the group consisting of halo, aryl, $Het^1$, and $Het^2$. $Het^1$ at each occurrence is independently a C-linked 5 or 6 membered heterocyclic ring having 1 to 4 heteroatoms selected from the group consisting of oxygen, nitrogen, and sulfur within the ring. $Het^2$ at each occurrence is independently a N-linked 5 or 6 membered heterocyclic ring having 1 to 4 nitrogen and optionally having one oxygen or sulfur within the ring.

In certain aspects, $R^2$ in a compound of formula I is H.

In certain aspects, $R^3$ and $R^4$ in a compound of formula I are independently selected from H and F.

In certain aspects, $R^2$ in a compound of formula I is H, and $R^3$ and $R^4$ are independently selected from H and F.

In certain aspects, $R^2$ in a compound of formula I is H, and $R^3$ and $R^4$ are both F.

In certain aspects, $R^2$ in a compound of formula I is $CH_2NHC(=O)R^6$, wherein $R^6$ is H, $C_{1-3}$alkyl, or $OC_{1-3}$alkyl. In certain aspects, $R^1$ in a compound of formula I is (4-$R^7$-1,2,3-triazol-1-yl)methyl, wherein $R^7$ is H, $C_{1-3}$alkyl, halo, or CN.

In certain aspects, $R^1$ in a compound of formula I is (5-$R^7$-isoxazol-3-yl)aminomethyl or (5-$R^7$-isoxazol-3-yl)oxymethyl, wherein $R^7$ is H, $C_{1-3}$alkyl, halo, or CN.

In certain aspects, $R^1$ in a compound of formula I is (4-$R^7$-1,2,3-triazol-1-yl)methyl, (5-$R^7$-isoxazol-3-yl)aminomethyl, or (5-$R^7$-isoxazol-3-yl)oxymethyl, wherein $R^7$ is H, $C_{1-3}$alkyl, halo, or CN.

In another aspect, compounds of formula I are selected from formula II

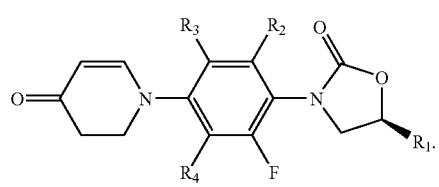

In another aspect, compounds of formula I are selected from formula III

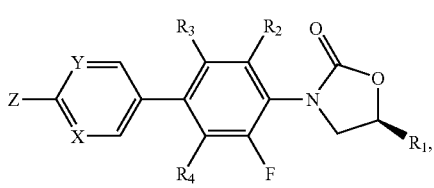

wherein X and Y are independently CH, CF, or N; and Z is $Het^1$, $Het^2$, a 4 to 7-membered heterocyclic group, CN, $CONH_2$, $CONHC_{1-6}$alkyl, NH—C(=O)H, NH—C(=O)$C_{1-6}$alkyl, NH—$SO_2C_{1-6}$alkyl, NH—C(=O)$OC_{1-6}$alkyl, or $NHC(=O)NHC_{1-6}$alkyl.

In certain aspects of a compound of formula III, X is CH, Y is N, and Z is 1-$C_{1-3}$alkyl-tetrazol-5-yl, 2-$C_{1-3}$alkyl-tetrazol-5-yl, or tetrazol-1-yl.

In certain aspects, X and Y in a compound of formula III are independently CH, CF, or N or CH, Z is $CH_2NHCH_2Het^1$ or $CH_2NHCH_2Het^2$, and $R^1$ is (4-$R^7$-1,2,3-triazol-1-yl)methyl, (5-$R^7$-isoxazol-3-yl)aminomethyl, or (5-$R^7$-isoxazol-3-yl)oxymethyl.

In another aspect, compounds of formula I are selected from formula IV

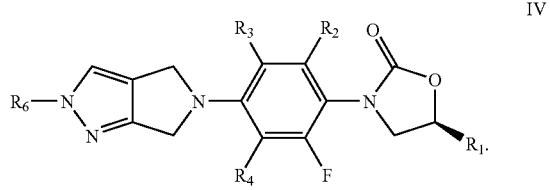

In certain aspects, compounds of formula IV are selected such that $R^1$ is (4-$R^7$-1,2,3-triazol-1-yl)methyl, (5-$R^7$-isoxazol-3-yl)aminomethyl, or (5-$R^7$-isoxazol-3-yl)oxymethyl.

In another aspect, compounds of formula I are selected from formula V

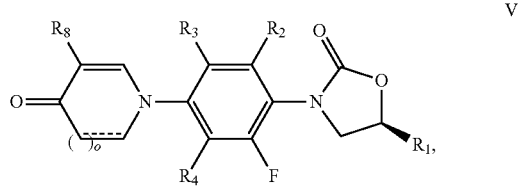

wherein $R^8$ is H, halo, CN, or $COR^6$; o is 1 or 2; and a line with a dotted line is either single or double bond.

In another aspect, compounds of formula I are selected from formula VI

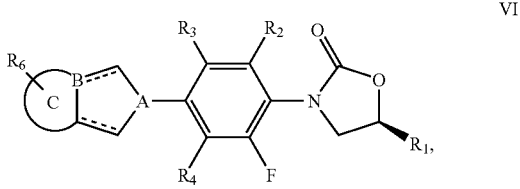

wherein A is N or $CH_2$, CHF, or CHMe; and
B is N, C, or CH; C is $Het^1$; and
the line with a dotted line is either a single or double bond.

In another aspect, compounds of formulas I are selected from formula VII

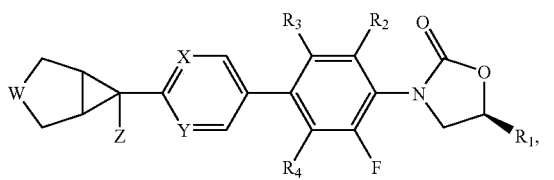

wherein X and Y are independently CH, CF, or N; Z is H, Me, CN, or F; and
W is NH, N—$C_{1-6}$alkyl, N—$C_{3-6}$cycloalkyl, N—C(=O)H, N—C(=O)$C_{1-6}$alkyl, N—Ar, N-$Het^1$, N-$Het^2$, N—CN, N—$SO_2C_{1-6}$alkyl, N—C(=O)$OC_{1-6}$alkyl, N—C(=O)$NHC_{1-6}$alkyl, O, or $S(O)_q$; and wherein q is 0, 1, or 2.

In another aspect, compounds of formula I are selected from formula VIII

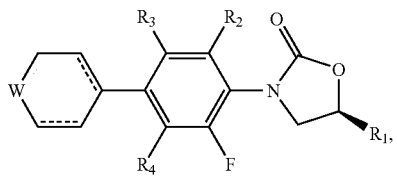

VIII wherein W is NH, N—$C_{1-6}$alkyl, N—$C_{3-6}$cycloalkyl, N—C(=O)H, N—C(=O)$C_{1-6}$alkyl, N—Ar, N-$Het^1$, N-$Het^1$, N—CN, N—$SO_2C_{1-6}$alkyl, N—C(=O)O$C_{1-6}$alkyl, N—C(=O)NH$C_{1-6}$alkyl, O, or S(O)$_q$; wherein q is 0, 1, or 2; and wherein the line with a dotted line is either a single or double bond.

In another aspect, compounds of formula I are selected from formula IX

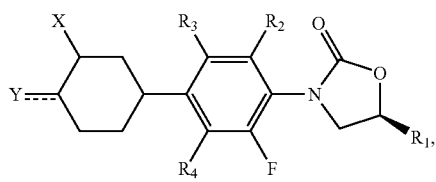

IX wherein X is F or OH; and
Y is O, OH, or F; and wherein the line with a dotted line is either a single or double bond.

In another aspect, the present invention provides a pharmaceutical composition comprising a compound of any of formulas I-IX, or a pharmaceutically acceptable salt thereof, and a pharmaceutically acceptable carrier.

In another aspect, the present invention provides a method for treating microbial infection in a mammal by administering to the mammal in need a therapeutically effective amount of a compound of any of formulas I-IX or a pharmaceutically acceptable salt thereof.

In certain aspects, the microbial infection is a gram-positive microbial infection.

The compounds of formulas I-IX may be administered orally, parenterally, transdermally, topically, rectally, or intranasally.

The compounds of formulas I-IX may be administered once-daily in an amount of from about 1 to about 75 mg/kg of body weight/day.

In certain aspects, provided herein is a compound according to any one of formulas I-IX for use in therapy.

In certain aspects, provided herein is a compound according to any one of formulas I-IX for use in the treatment of a microbial infection in a mammal in need thereof.

In certain aspects, provided herein is use of a compound according to any one of formulas I-IX in the manufacture of a medicament for therapy.

In certain aspects, provided herein is use of a compound according to any one of formulas I-IX in the manufacture of a medicament for treatment of a bacterial infection in a mammal in need thereof. In another aspect, the compounds of formulas I-IX can be used in combinations with other bioactive agents, such as anti-infective or anti-inflammatory agents. For example, to achieve an optimal therapeutic effect (such as a broad spectrum of action), compounds of formulas I-IX active against gram-positive pathogens may be co-administered in a combination with an antimicrobial agent active against gram-negative bacteria (e.g., quinolone, beta-lactam, aminoglycoside, colistin, macrolide agent, etc.), an agent active against pathogenic fungi or yeast (e.g., allylamine, terbinafine, azole, etc.), or in combination with an antiviral agent (such as an entry-blocker, viral protease or DNA inhibitor, antiretroviral agent, etc.).

In another aspect, the present invention provides antibacterial compounds of formulas I-IX with reduced monoamine oxidase inhibitory properties in vitro or in vivo.

In additional aspects, provided herein are compounds of formulas I-IX with reduced monoamine oxidase inhibitory properties over the antibacterial oxazolidinone therapy standard, such as linezolid.

In further aspect, the present invention provides compounds of formula I-IX with reduced monoamine oxidase inhibitory properties over their respective analogs lacking the mandatory ortho-fluorophenyl oxazolidinone substitution. The latter compounds can be, for example, said analogs featuring ortho-hydrogen instead of the ortho-F substituent.

Yet in another aspect, the present invention provides antibacterial compounds with a reduced hematopoietic (i.e. myelosuppression or bone marrow) toxicity in vitro or in vivo.

In additional aspects, provided herein are compounds of formulas I-IX with reduced myleosuppression over the antibacterial oxazolidinone therapy standard, such as linezolid.

In further aspect, the present invention provides compounds of formulas I-IX with reduced myleosuppression over their analogs lacking the ortho-fluorophenyl oxazolidinone substitution (for example, the latter analogs featuring ortho-hydrogen instead of the ortho-F substituent).

In yet another aspect, the present invention provides novel intermediates and processes for preparing compounds of formulas I-IX.

DETAILED DESCRIPTION OF THE INVENTION

Unless otherwise stated, the following terms used in the specification and Claims have the meanings given below:

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

Group $R^{\#}$ is same as $R_{\#}$: $R^1$ is same as $R_1$, etc.

The terms "alkyl," "alkenyl," etc. refer to both straight and branched groups, but reference to an individual radical such as "propyl" embraces only the straight chain radical, a branched chain isomer such as "isopropyl" being specifically referred to. The alkyl, alkenyl, etc., group may be optionally substituted with one, two, or three substituents selected from the group consisting of halo, aryl, $Het^1$, or $Het^2$. Representative examples include, but are not limited to, difluoromethyl, 2-fluoroethyl, trifluoroethyl, —CH=CH-aryl, —CH=CH-$Het^1$, —$CH_2$-phenyl, and the like.

The term "cycloalkyl" means a cyclic saturated monovalent hydrocarbon group of three to six carbon atoms, e.g., cyclopropyl, cyclohexyl, and the like. The cycloalkyl group may be optionally substituted with one, two, or three substituents selected from the group consisting of halo, aryl, $Het^1$, or $Het^2$.

The term "heteroalkyl" means an alkyl or cycloalkyl group, as defined above, having a substituent containing a heteroatom selected from N, O, or S(O)$_n$, where n is an integer from 0 to 2, including, hydroxy (OH), $C_{1-4}$alkoxy, amino, thio (—SH), and the like. Representative substituents include —NR$_a$R$_b$, —OR$_a$, or —S(O)$_n$R$_c$, wherein R$_a$ is hydrogen, C$_{1-4}$alkyl, C$_{3-6}$cycloalkyl, optionally substituted aryl, optionally substituted heterocyclic, or —COR (where R is C$_{1-4}$alkyl); R$_b$ is hydrogen, C$_{1-4}$alkyl, —SO$_2$R (where R is C$_{1-4}$alkyl or C$_{1-4}$hydroxyalkyl), —SO$_2$NRR' (where R and R' are independently of each other hydrogen or C$_{1-4}$alkyl), —CONR'R" (where R' and R" are independently of each other hydrogen or C$_{1-4}$alkyl); n is an integer from 0 to 2; and R$^c$ is hydrogen, C$_{1-4}$alkyl, C$_{3-6}$cycloalkyl, optionally substituted aryl, or NR$_a$R$_b$ where R$_a$ and R$_b$ are as defined above. Representative examples include, but are not limited to, 2-methoxyethyl (—CH$_2$CH$_2$OCH$_3$), 2-hydroxyethyl (—CH$_2$CH$_2$OH), hydroxymethyl (—CH$_2$OH), 2-aminoethyl (—CH$_2$CH$_2$NH$_2$), 2-dimethylaminoethyl (—CH$_2$CH$_2$NHCH$_3$), benzyloxymethyl, thiophen-2-ylthiomethyl, and the like.

The term "halo" refers to fluoro (F), chloro (Cl), bromo (Br), or iodo (I).

The term "aryl" refers to phenyl, biphenyl, or naphthyl, optionally substituted with 1 to 3 substituents independently selected from halo, —C$_{1-4}$alkyl, —OH, —OC$_{1-4}$alkyl, —S(O)$_n$C$_{1-4}$alkyl wherein n is 0, 1, or 2, —C$_{1-4}$alkylNH$_2$, —NHC$_{1-4}$alkyl, —C(=O)H, or —C=N—OR$_d$ wherein R$_d$ is hydrogen or —C$_{1-4}$alkyl. Likewise, the term phenyl refers to the phenyl group optionally substituted as above.

The term "heterocyclic ring" refers to an aromatic ring or a saturated or unsaturated ring that is not aromatic of 3 to 10 carbon atoms and 1 to 4 heteroatoms selected from the group consisting of oxygen, nitrogen, and S(O)$_n$ within the ring, where n is defined above. The heterocyclic ring may be optionally substituted with halo, —C$_{1-4}$alkyl, —OH, —OC$_{1-4}$ alkyl, —S(O)$_n$C$_{1-4}$alkyl wherein n is 0, 1, or 2, —C$_{1-4}$alkylNH$_2$, —NHC$_{1-4}$alkyl, —C(=O)H, or —C=N—OR$_d$ wherein R$_d$ is hydrogen or C$_{1-4}$alkyl.

Examples of heterocylic rings include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isoxazolinone, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiadiazole tetrazole, thiazolidine, thiophene, benzo[b]thiophene, morpholinyl, thiomorpholinyl (also referred to as thiamorpholinyl), piperidinyl, pyrrolidine, tetrahydrofuranyl, 1,3-benzoxazine, 1,4-oxazine-3-one, 1,3-benzoxazine-4-one, pyrrolidine, pyrrolidine-2-one, oxazolidine-2-one, azepine, perhydroazepine, perhydroazepine-2-one, perhydro-1,4-oxazepine, perhydro-1,4-oxazepine-2-one, perhydro-1,4-oxazepine-3-one, perhydro-1,3-oxazepine-2-one and the like. Heterocyclic rings include unsubstituted and substituted rings.

Specifically, Het$^1$ (same as het$^1$, Het$_1$ or het$_1$) refers to a C-linked five- (5) or six- (6) membered heterocyclic ring, including bicyclic rings. Representative examples of "Het$^1$" include, but are not limited to, pyridine, thiophene, furan, pyrazole, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,5-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-dithiazolone, or 3-azabicyclo[3.1.0]hexan-6-yl.

Het$^2$ (same as het$^2$, Het$_2$, or het$_2$) refers to an N-linked five- (5) or six- (6) membered heterocyclic ring having 1 to 4 nitrogen atoms, and optionally having one oxygen or sulfur atom, including bicyclic rings. Representative examples of "Het$^2$" include, but are not limited to pyrrolyl, imidazolyl, pyrazolyl, 1,2,3-triazolyl, 1,2,4-triazolyl, 1,2,3,4-tetrazolyl, isoxazolidinonyl group, 3-azabicyclo[3.1.0]hexan-3-yl, 1,3, 9,9a-tetrahydrooxazolo[3,4-a]indol-1-yl, 2-alkylpyrrolo[3, 4-c]pyrazol-5(2H,4H,6H)-yl, and 5H-pyrrolo[3,4-b]pyridin-6(7H)-yl.

"Optional" or "optionally" means that the subsequently described event or circumstance may, but need not, occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and Claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A hydrogen (H) or carbon (C) substitution for compounds of the formula I include a substitution with any isotope of the respective atom. Thus, a hydrogen (H) substitution includes a $^1$H, $^2$H (deuterium), or $^3$H (tritium) isotope substitution, as may be desired, for example, for a specific therapeutic or diagnostic therapy, or metabolic study application. Optionally, a compound of this invention may incorporate a known in the art radioactive isotope or radioisotope, such as $^3$H, $^{15}$O, $^{12}$C, or $^{13}$N isotope, to afford a respective radiolabeled compound of formula I.

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and Claims includes both one and more than one such carrier.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The therapeutically effective amount will vary depending on the compound, the disease and its severity and the age, weight, etc., of the mammal to be treated. Therapeutically effective amount may also be referred to as any amount of a compound that is sufficient to achieve the desired beneficial effect, including preventing the disease, inhibiting the disease, or relieving the disease, as described above in (1)-(3). For example, the amount of a compound can range between 0.1-250 mg/kg, or preferably, 0.5-100 mg/kg, or more preferably, 1-50 mg/kg, or even more preferably, 2-20 mg/kg. More preferably, said amount of a compound is administered to a mammal once-daily. Even more preferably, said amount of a compound is administered to a mammal once-weekly or once-biweekly.

"Leaving group" has the meaning conventionally associated with it in synthetic organic chemistry, i.e., an atom or group capable of being displaced by a nucleophile and includes halogen, $C_{1-4}$alkylsulfonyloxy, ester, or amino such as chloro, bromo, iodo, mesyloxy, tosyloxy, trifluorosulfonyloxy, methoxy, N,O-dimethylhydroxyl-amino, and the like.

"Prodrug" means any compound which releases an active parent drug according to a compound of the subject invention in vivo when such prodrug is administered to a mammalian subject. Various prodrugs have been described, for example, in the following publications: Alexander et al. J. Med. Chem. 1988, p. 318; Alexander et al. J. Med. Chem., 1991, p. 78; Murdock et al. J. Med. Chem., 1993, p. 2098; Davidsen et al. J. Med. Chem., 1994, p. 4423; Robinson et al. J. Med. Chem., 1996, p. 10; Keyes et al. J. Med. Chem., 1996, p. 508; Krise et al. J. Med. Chem., 1999, p. 3094; Rahmathullah et al. J. Med. Chem., 1999, p. 3994; Zhu et al. Bioorg. Med. Chem. Lett., 2000, p. 1121; Sun et al., J. Med. Chem., 2001, p. 2671; Ochwada et al., Bioorg. Med. Chem. Lett., 2003, p. 191; Sohma et al. Med. Chem., 2003, p. 4124; Ettmayer et al. J. Med. Chem., 2004, p. 2393; Stella et al., Adv. Drug Delivery Rev., 2007, p. 677, Josyula et al. International Patent Publication No. WO 2005/028473; Rhee et al. International Patent Publication No. WO 2005/058886, and EP 1,683,803. Following methods of these publications and refs. cited therein, respective prodrugs of the compounds of the present invention can be likewise prepared. Thus, prodrugs of compounds of the formula I are prepared by modifying functional groups present in a compound of the subject invention in such a way that the modifications may be cleaved in vivo to release the parent compound. Said prodrugs can be used, for example, to improve aq. solubility, oral, transdermal, or ocular bioavailability, to achieve a controlled (e.g., extended) release of the drug moiety, to improve tolerability, etc. Prodrugs include compounds of the subject invention wherein a hydroxy, sulfhydryl, amido or amino group in the compound is bonded to any group that may be cleaved in vivo to regenerate the free hydroxyl, amido, amino, or sulfhydryl group, respectively. Examples of prodrugs include, but are not limited to esters (e.g., acetate, formate, benzoate, phosphate or phosphonate derivatives), carbamates (e.g., N,N-dimethylaminocarbonyl), N-phosphoramides, of hydroxyl or amine-derived functional groups in compounds of the subject invention. Prodrug derivative can be used either as a neutral prodrug form (e.g. acid or amine), or a respective salt form thereof [e.g. sodium salt of a phosphate prodrug, or an amine salt (e.g. hydrochloride, citrate, etc.) for an amine group-bearing prodrug], or a zwitterionic form if both positively and negatively charged/ionizable functions are present. Prodrug groups may be incorporated at various sites of the formula I.

Several preferred prodrug structures of this invention are illustrated below.

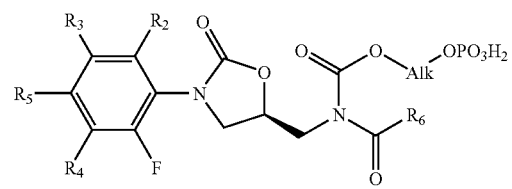

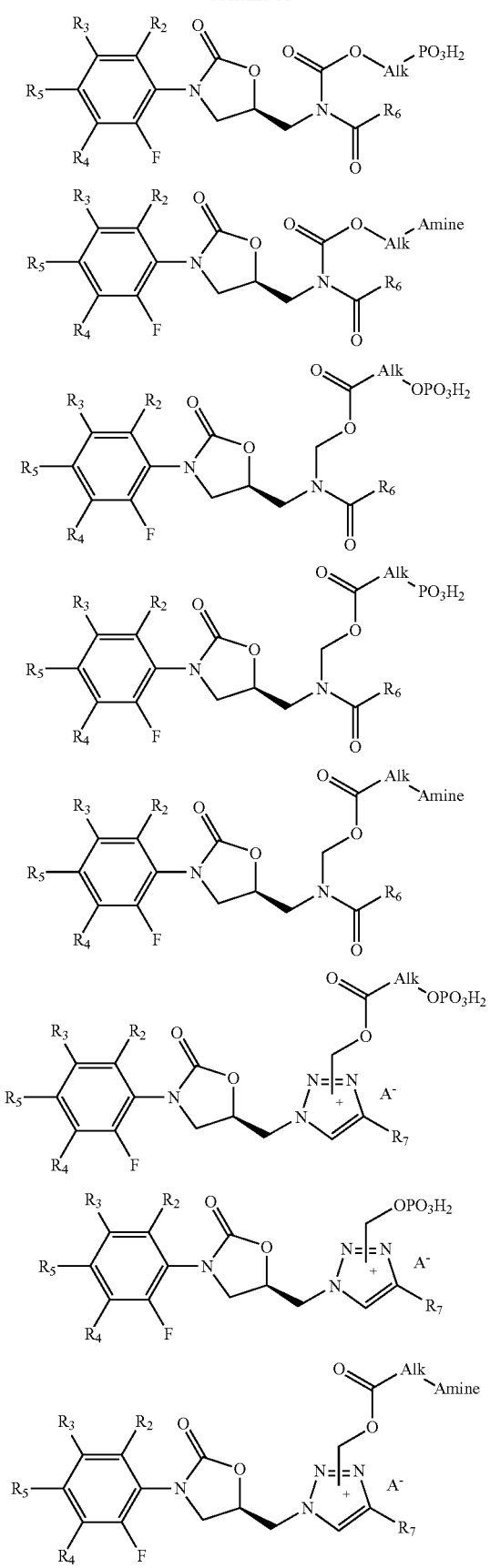
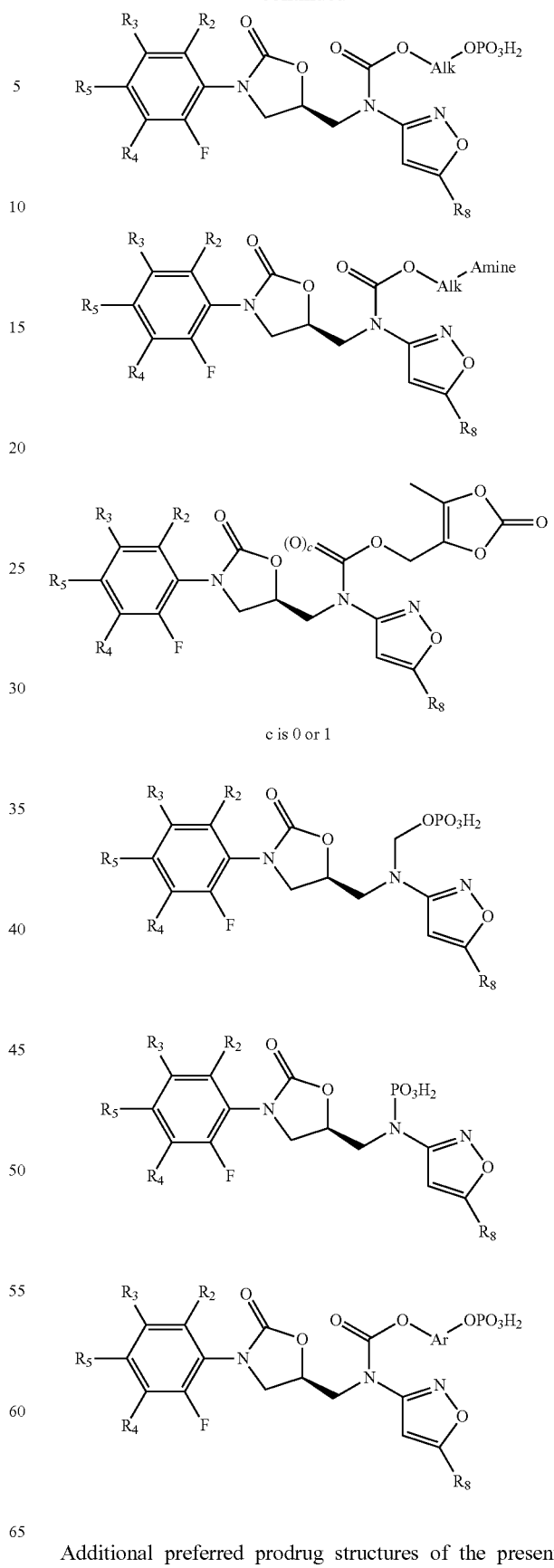
c is 0 or 1
Additional preferred prodrug structures of the present invention are illustrated below.

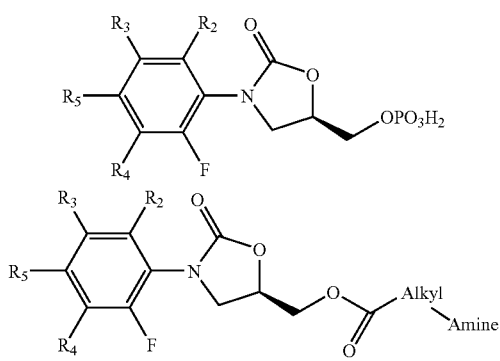

The term "mammal" refers to all mammals including humans, livestock, and companion animals.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "r.t." for room temperature).

Illustrative Aspects

Within the broadest definition of the present invention, certain compounds of the compounds of formula I may be preferred. Specific and preferred values listed below for radicals, substituents, and ranges, are for illustration only; they do not exclude other defined values or other values within defined ranges for the radicals and substituents.

In some preferred compounds of the present invention $C_{1-4}$alkyl can be methyl, ethyl, propyl, isopropyl, butyl, isobutyl, sec-butyl, and isomeric forms thereof.

In some preferred compounds of the present invention $C_{2-4}$alkenyl can be vinyl, propenyl, allyl, butenyl, and isomeric forms thereof (including cis and trans isomers).

In some preferred compounds of the present invention $C_{3-6}$cycloalkyl can be cyclopropyl, cyclobutyl, cyclopentyl, cyclohexyl, and isomeric forms thereof.

In some preferred compounds of the present invention $C_{1-4}$ heteroalkyl can be hydroxymethyl, hydroxyethyl, and 2-methoxyethyl.

In some preferred compounds of the present invention halo can be fluoro (F) or chloro (Cl).

In some preferred compounds of the present invention $R^1$ can be $CH_2C(=O)C_{1-4}$alkyl or $CH_2C(=O)OC_{1-4}$alkyl.

In some preferred compounds of the present invention $R^1$ can be (4-$R^7$-1,2,3-triazol-1-yl)methyl, (5-$R^7$-isoxazol-3-yl) aminomethyl, or (5-$R^7$-isoxazol-3-yl)oxymethyl, wherein $R^7$ is H, $C_{1-3}$alkyl, halo, or CN.

In some preferred aspects, group $R^1$ is selected from $CH_2OH$, $CH(OH)CH=CH_2$, or $CH(OH)C\equiv CH$.

In some preferred aspects, group $R^1$ is selected from $CONH_2$ or $CONHMe$.

In some preferred aspects, group $R^1$ is selected from $CH_2NHC(=O)Me$, $CH_2NHC(=O)Et$, or $CH_2NHC(=O)$ OMe.

In some preferred aspects, group $R^1$ is selected from $CH_2$ (1,2,3-triazol-1-yl) or $CH_2$(4-methyl-1,2,3-triazol-1-yl).

In some preferred aspects, group $R^1$ is selected from $CH_2NH$(isoxazol-3-yl), $CH_2O$(isoxazol-3-yl), $CH_2NH$(pyridin-2-yl), or $CH_2O$(pyridin-2-yl), $CH_2NH$(pyridin-3-yl), or $CH_2O$(pyridin-3-yl).

In some preferred aspects, groups $R^2$, $R^3$ and $R^4$ are independently selected from H or F.

In some preferred aspects, group $R^2$ is H, and group $R^6$ is F.

In some preferred aspects, $R^2$, $R^3$ and $R^4$ independently can be H or F.

In some preferred aspects, one of $R^4$ and $R^5$ is H and the other is F.

In some preferred aspects, $Het^1$ can be 2-pyridyl, 3-pyridyl, 4-pyridyl, 3-isoxazolyl, 4-isoxazolyl, 5-isoxazolyl, 1,2,3-triazol-1-yl, 1,2,5-thiadiazol-3-yl, and isoxazolidin-3-yl group.

In some preferred aspects, $Het^2$ can be pyrrolyl, imidazolyl, pyrazolyl, 1,2,3-triazolyl, 1,2,4-triazolyl, 1,2,3,4-tetrazolyl, and isoxazolidin-3-yl group.

It will also be appreciated by those skilled in the art that compounds of the present invention may have additional chiral centers and be isolated in optically active and racemic forms. The present invention encompasses any racemic, optically active, tautomeric, or stereoisomeric form, or mixture thereof, of a compound of the invention.

One preferred group of compounds of the present invention is illustrated by:

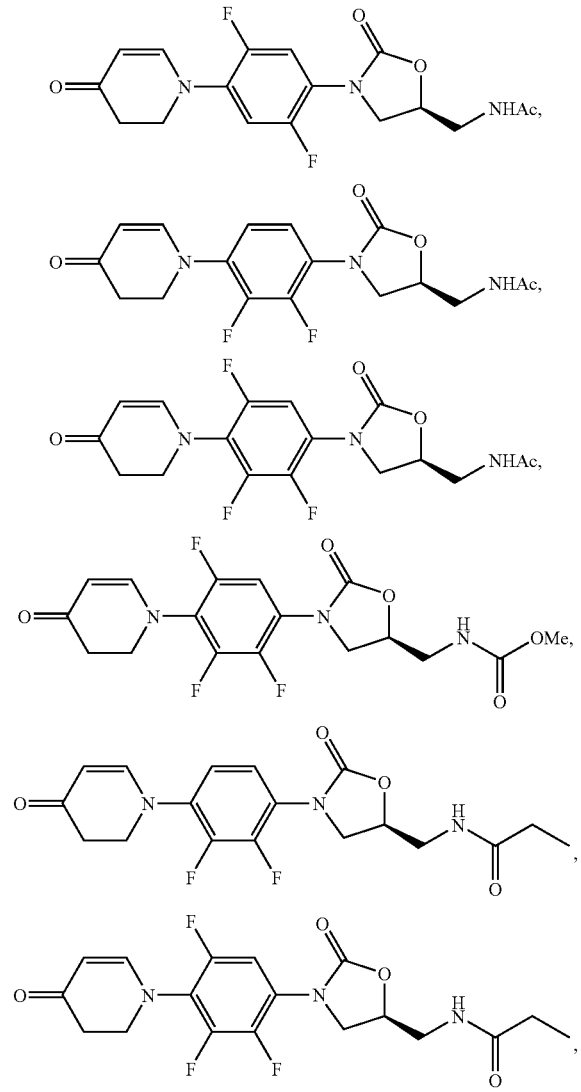

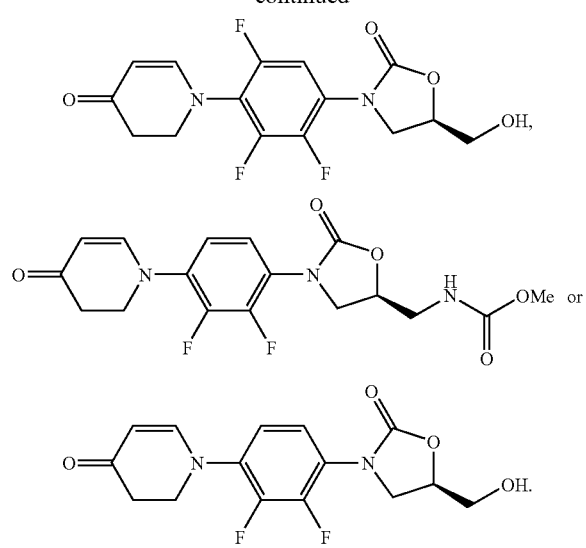
Additional preferred group of compounds of the present invention is illustrated by:
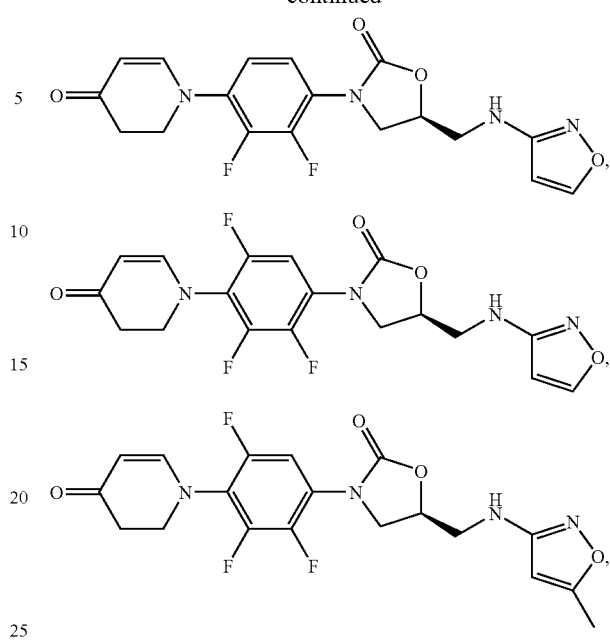
Another preferred group of compounds of the present invention is illustrated by:
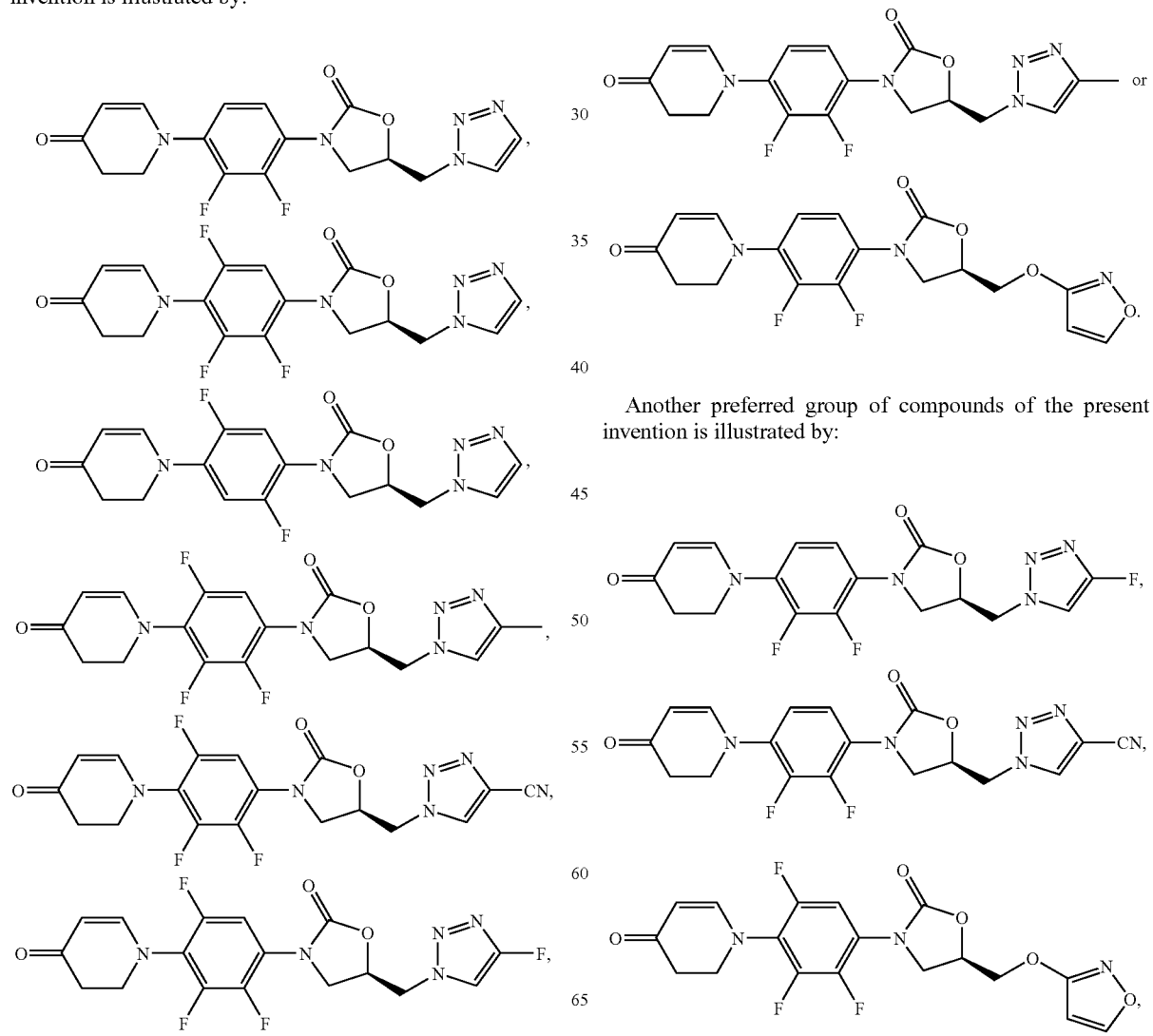

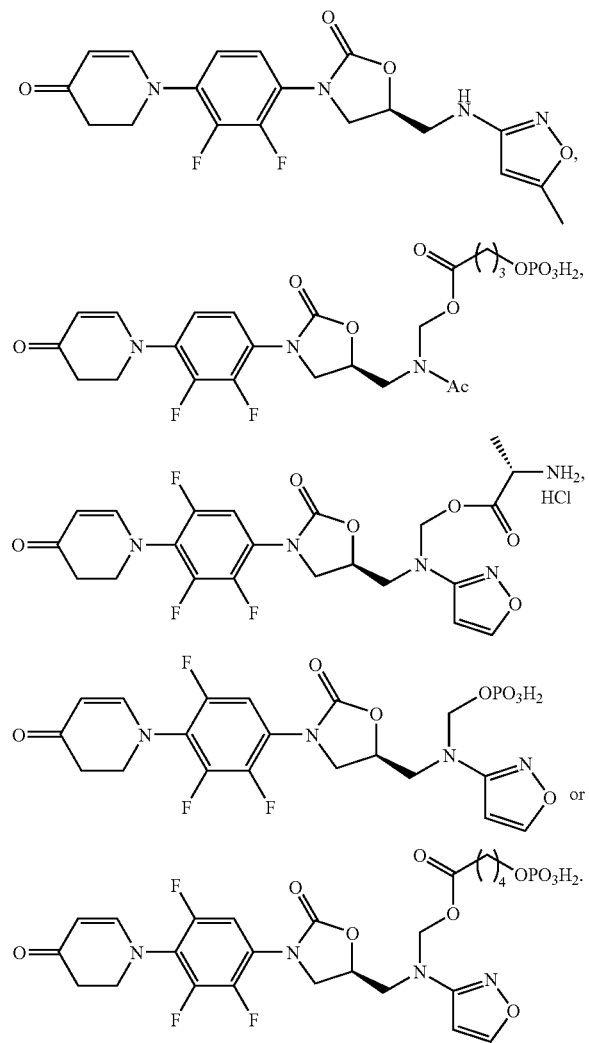
Additional preferred group of compounds of the present invention is illustrated by:
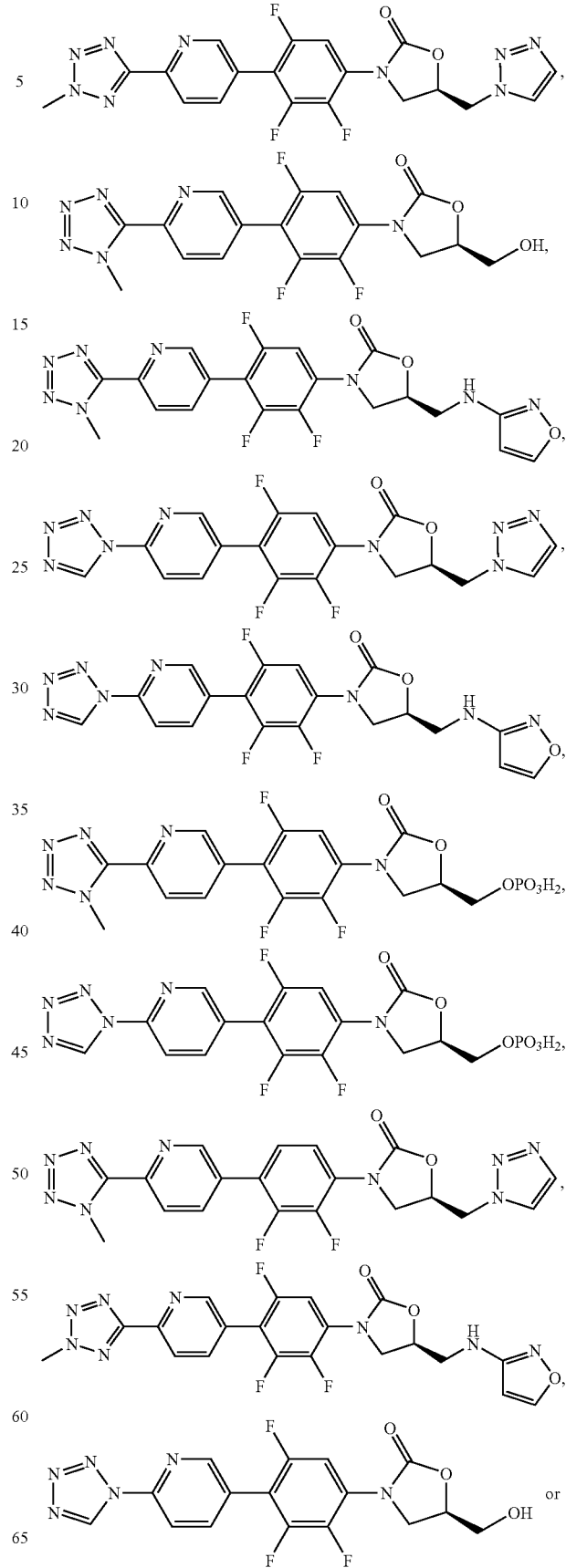

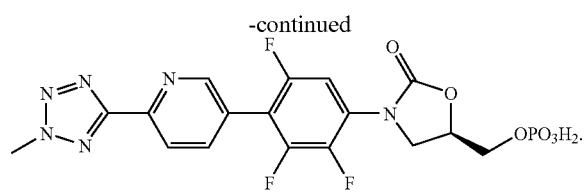
Another preferred group of compounds of the present invention is illustrated by:
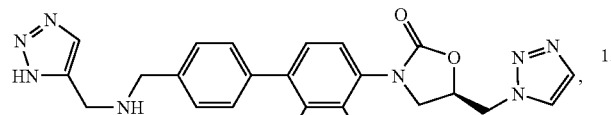
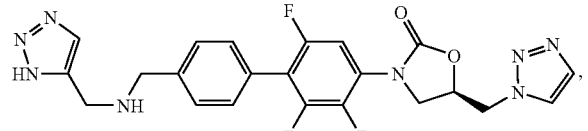
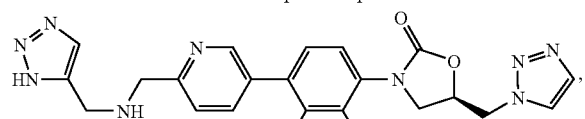
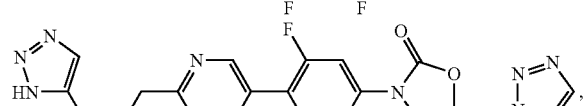
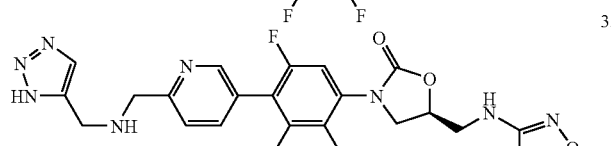
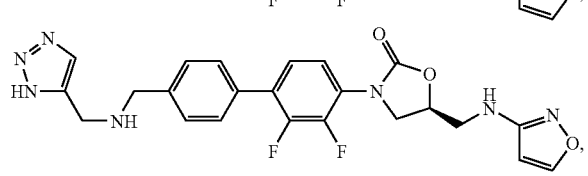
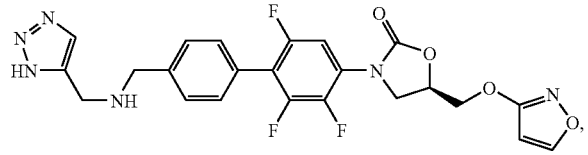
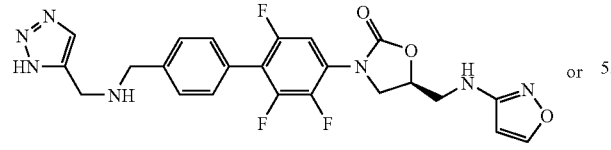
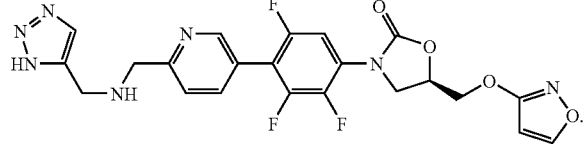
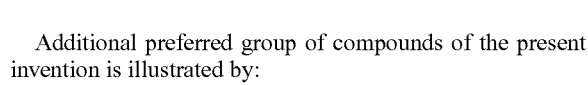
Additional preferred group of compounds of the present invention is illustrated by:
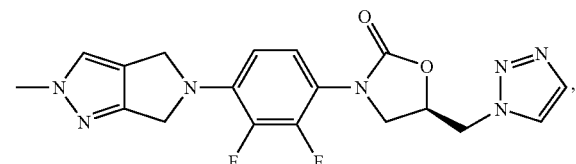
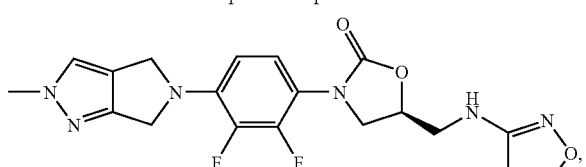
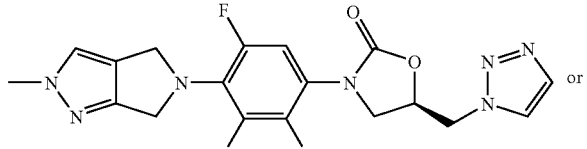
Another preferred group of compounds of the present invention is illustrated by:
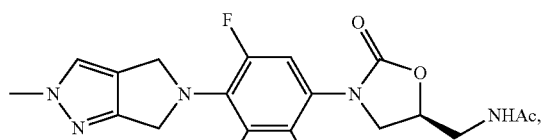
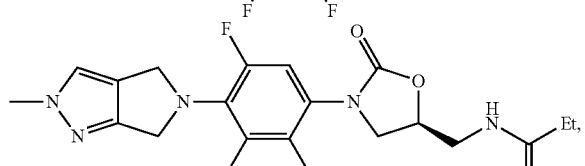
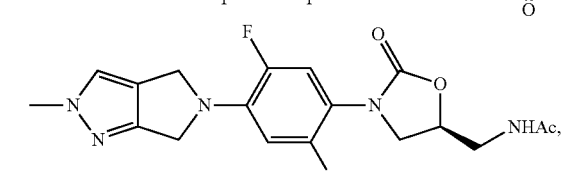
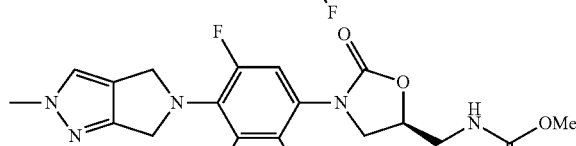
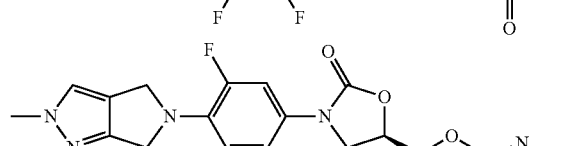
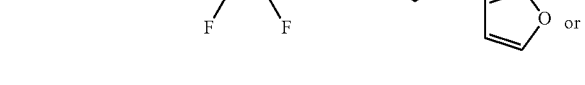

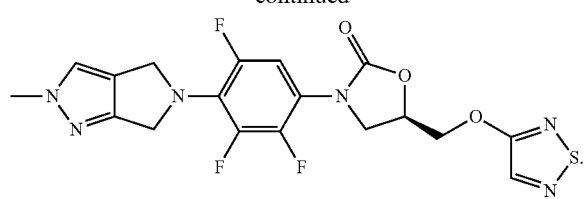
Another preferred group of compounds of the present invention is illustrated below.
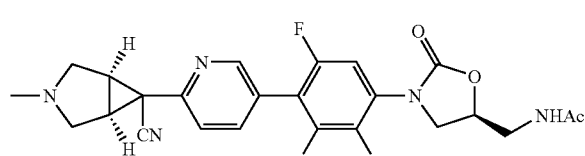
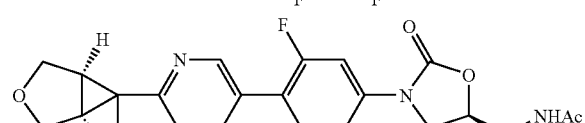
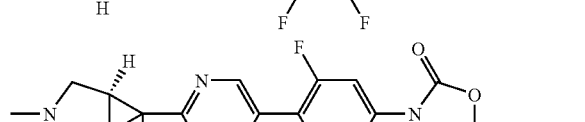
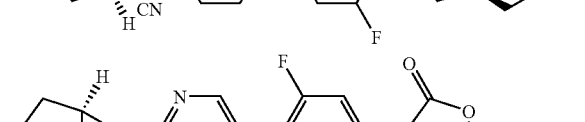
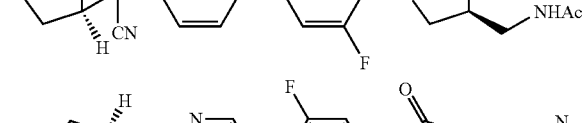
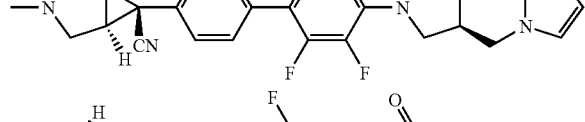
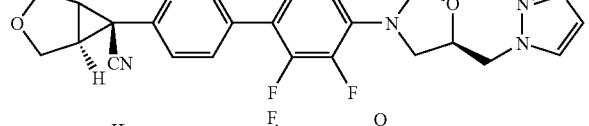
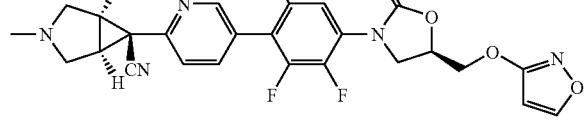
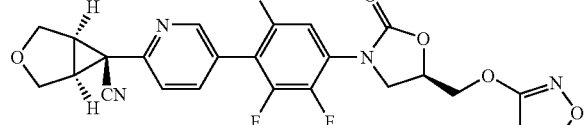
Another preferred group of compounds of the present invention is illustrated below.
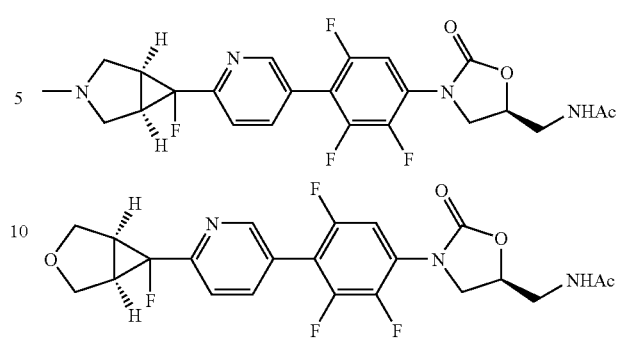
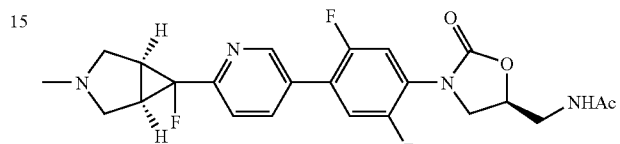
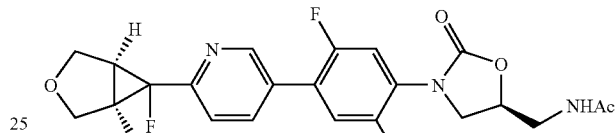
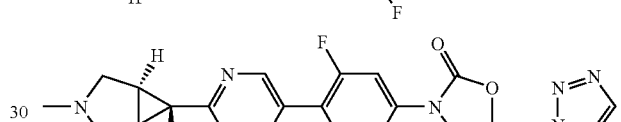
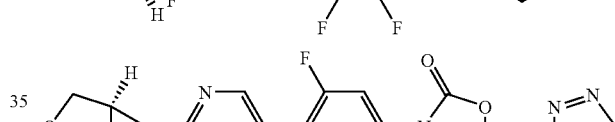
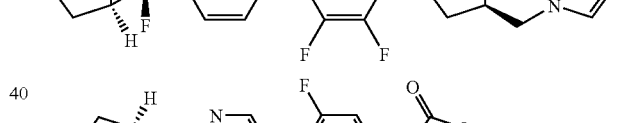
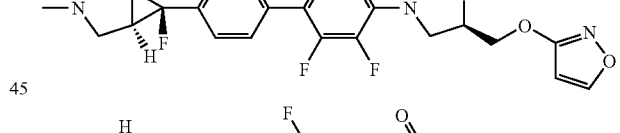
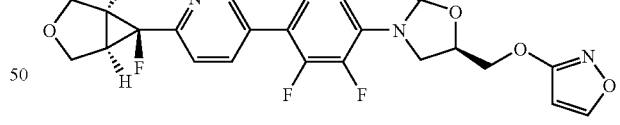
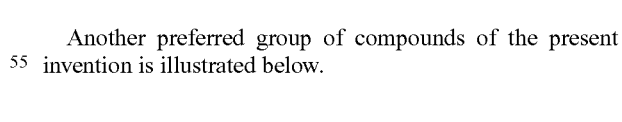
Another preferred group of compounds of the present invention is illustrated below.
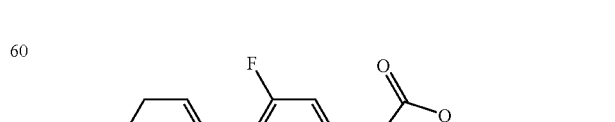

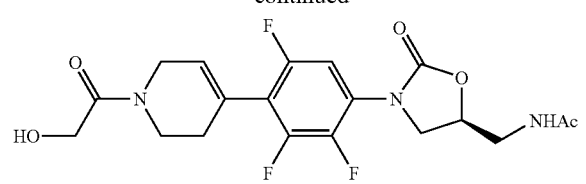
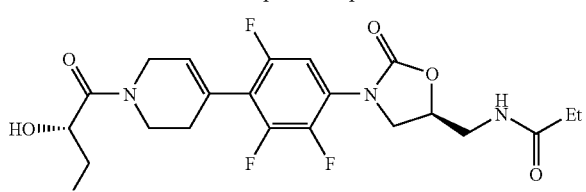
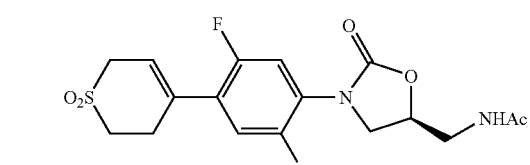
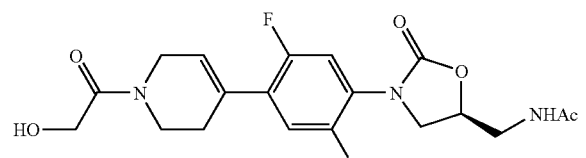
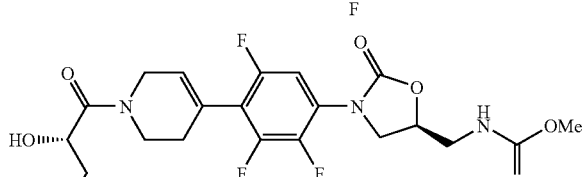
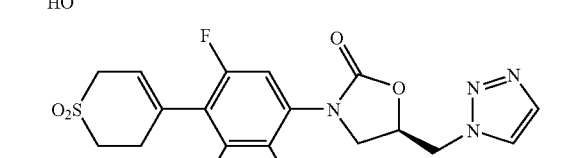
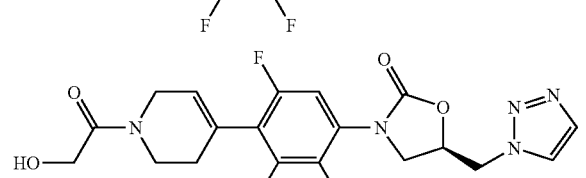
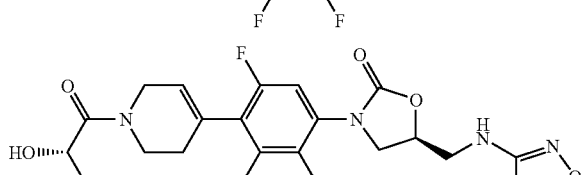
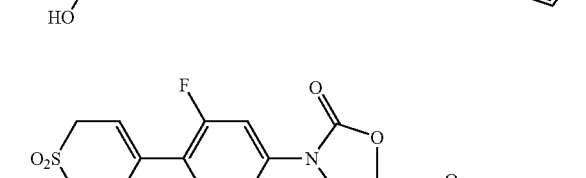
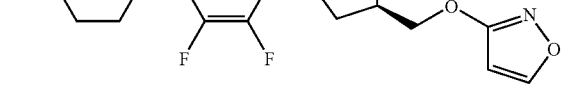
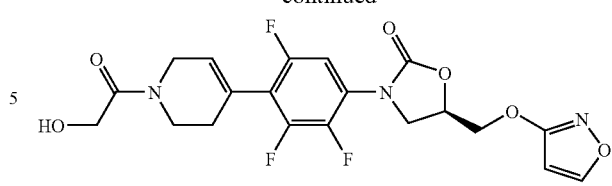
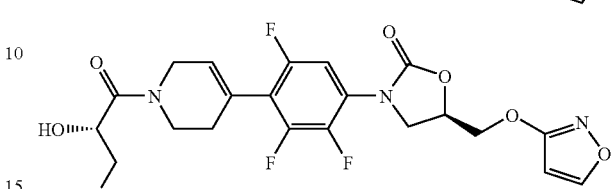
Yet another preferred group of compounds of the present invention is illustrated below.
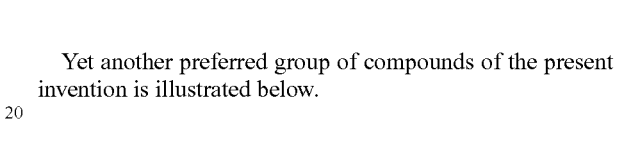
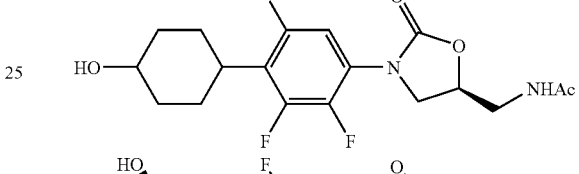
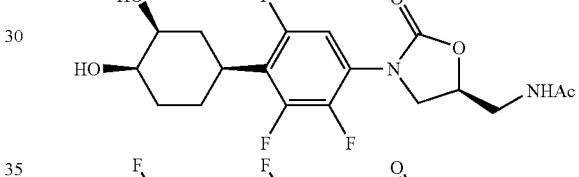
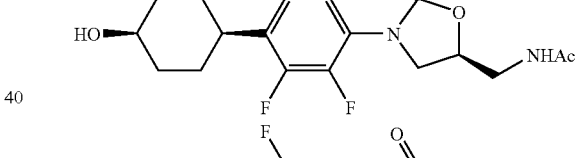
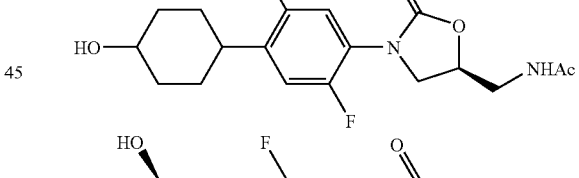
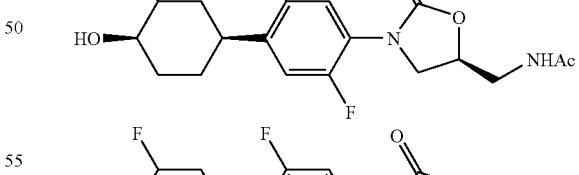
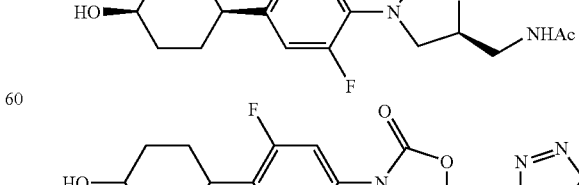
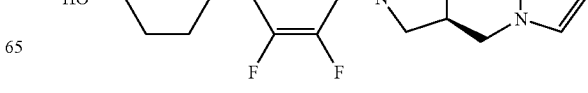

-continued

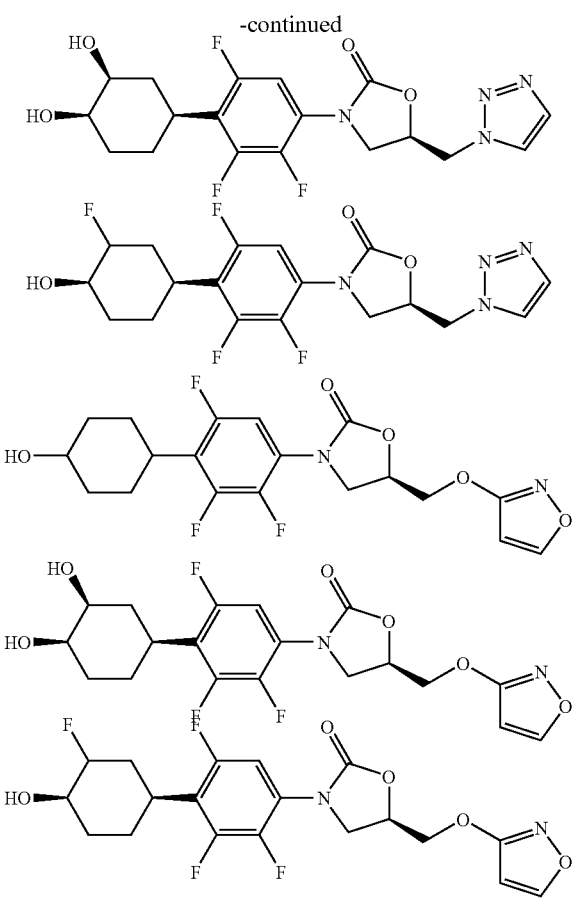

General Synthetic Methods

The compounds of this invention can be prepared in accordance with one or more of Schemes discussed below. Synthesis of ortho-fluorophenyl oxazolidinones of this invention may generally follow known in the heterocyclic synthetic art methods described for certain des-ortho-fluorophenyl heterocyclic derivatives (i.e. those lacking the ortho-F group). To achieve the requisite ortho-fluorophenyl substitution pattern in a compound of the present invention, an aromatic reagent generally described for preparation of des-ortho-fluorophenyl heterocyclic compounds can be intentionally replaced for a specific reagent containing at least one appropriately positioned ortho-F substituent.

One general approach to the compounds of this invention is illustrated in general Scheme 1. Each specific step of Scheme 1 has relevant analogy in the general synthetic and heterocyclic art. For example, several oxazolidinone-forming reagents similar to that employed at the step (c) of the Scheme 1 have been more generally described in Org. Proc. Res. & Development, 2003, p. 533. Variations of these methods may include non-critical manipulations to remove optional other protective groups, if different from tert-butoxycarbonyl (Boc) group illustrated in Scheme 1. For example, the former may be replaced with an imine protection as more generally described in International Patent Publication No. WO 2007/116284.

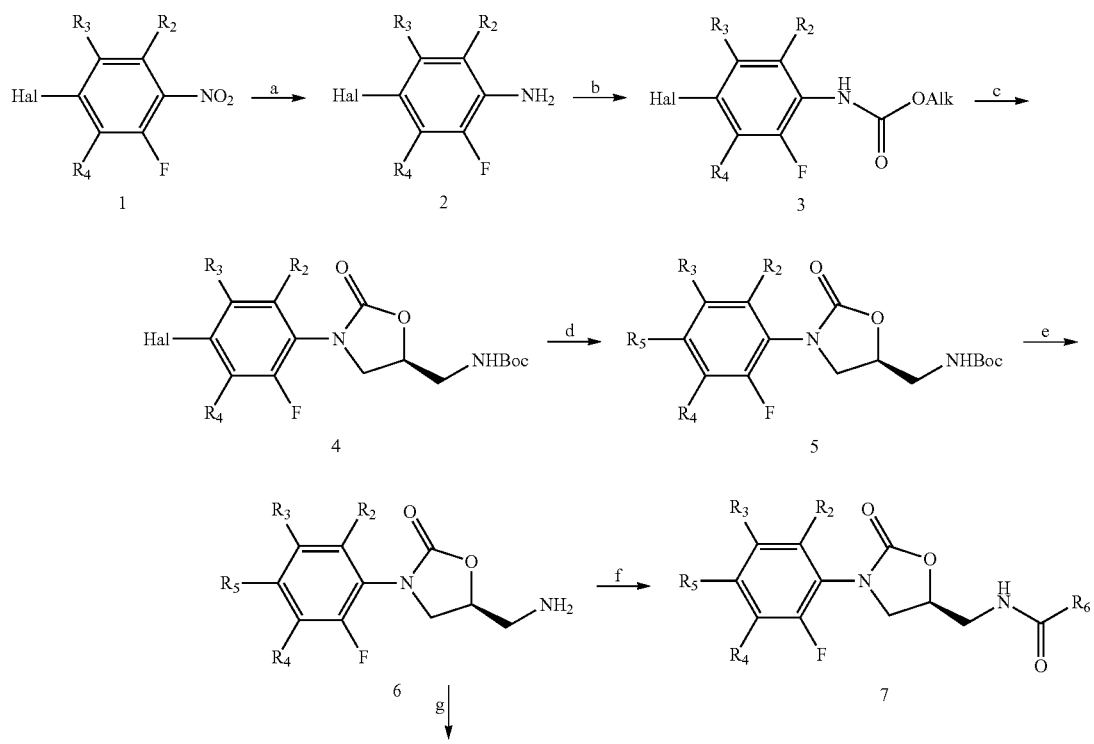

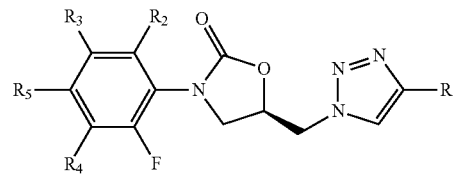

8

Scheme 1. General synthesis of ortho-fluorophenyl oxazolidinone derivatives. a) reducing reagent(s): e.g. $H_2$, Pd/C, Fe/$NH_4$Cl, or $SnCl_2$ etc.; b) Carbamate-forming reagent: e.g. AlkOC(=O)Cl, AlkOCOC$_6$F$_5$, or alike; base: NaOH, NaH, Py, triethylamine (TEA) or alike; c) oxazolidinone-forming reagent(s): e.g., (S)-tert-butyl 3-chloro-2-hydroxypropylcarbamate, or (S)-tert-butyl oxiran-2-ylmethylcarbamate; base: LiOBu-t, KOBu-t, NaH, or alike; d) arylating or heteroarylating reagent(s): e.g. Ar—B(OH)$_2$, Ar—B(OAlk')$_2$, Het$^1$-B(OH)$_2$, Het$^1$-B(OAlk')$_2$, Het$^2$-B(OH)$_2$, or Het$^2$-B(OAlk')$_2$ selected from boronic acid, boronic acid ester (e.g. (picolinato)boron ester) or alike, Pd catalyst (e.g. PdCl$_2$(dppf)DCM, Pd(PPh$_3$)$_4$ or alike); e) acid (e.g. TFA or HCl solution in organic solvent, e.g. THF or dioxane), base (e.g., NaHCO$_3$, TEA, or alike); f) acylating agent: e.g. R$^6$C(=O)Cl, R$^6$C(=)OC$_6$F$_5$, or R$^6$COOH/HATU; base: K2CO3, TEA or alike; g) triazole-forming reagent: e.g. TsNHN=C(CHCl$_2$)Alk; base: e.g., K$_2$CO$_3$, TEA, or alike.

Analogously to the step (d) of Scheme 1, various heterocyclic derivatives have been prepared by metal-mediated transformations of 4-halo-phenyl heterocyclic derivatives as more generally described, for example, in International Patent Publication Nos. WO 1999/064417, 2005/012271, and WO 2005/058886. Likewise, boron-coupling chemistry of step (d) may be optionally supplanted by other metal-mediated couplings, such as tin-coupling chemistry similar to that described more generally in WO 2005/012271.

Additional general routes to the compounds of this invention are illustrated in Scheme 2. Mitsunobu alkylation chemistry of step (c) is precedented in analogous heterocyclic chemistry more generally described, for example, in International Patent Publication No. WO 1999/064416. Triazole-forming chemistry analogous to that of step (e) of this scheme has been generally described, for example, in Heterocycles, 1998, p. 895, and in Org. Lett., 2008, p. 497.

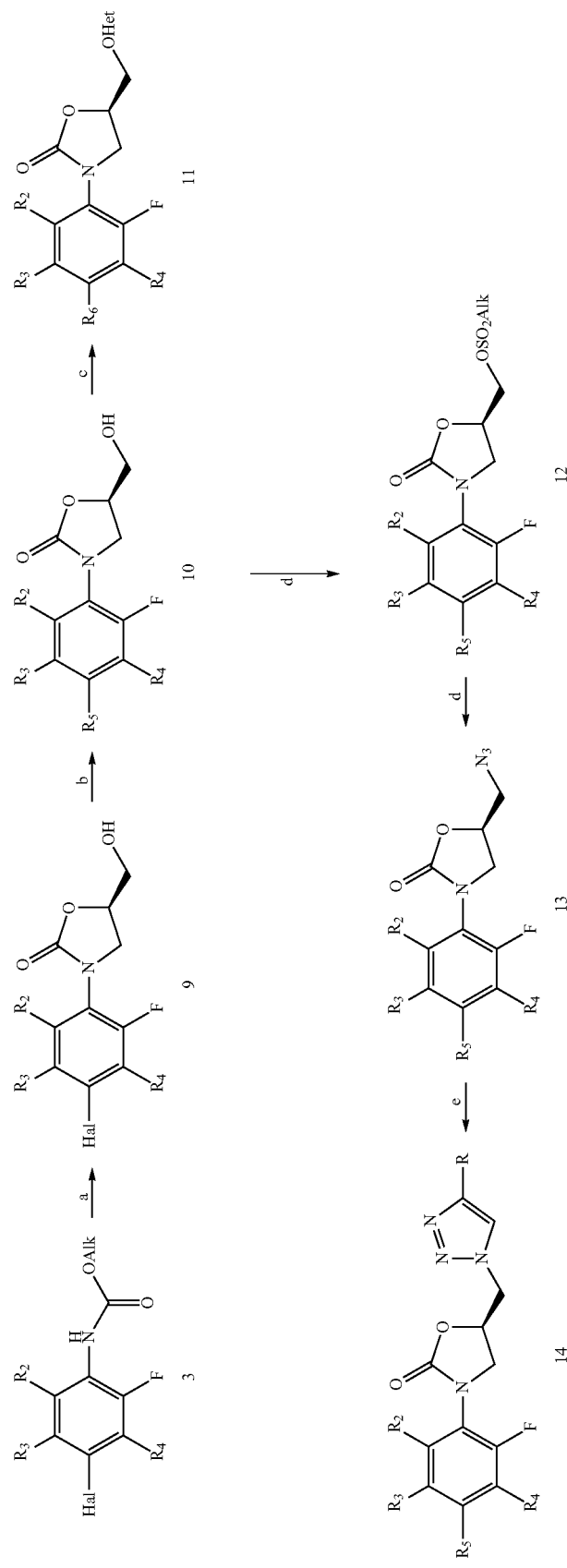

Scheme 2. General synthesis of ortho-fluorophenyl oxazolidinone derivatives. a) oxazolidinone-forming reagent(s): (R)-glycidyl butyrate, (R)-glycidol, or alike; base: BuLi, lithium hexamethyldisilylamide (LHMDS), LiOBu-t, KOBu-t, NaH, or alike; b) arylating or heteroarylating reagent(s): e.g. Ar—B(OH)$_2$, Ar—B(OAlk')$_2$, Het$^1$-B(OH)$_2$, Het$^1$-B(OAlk')$_2$, Het$^2$-B(OH)$_2$, or Het$^2$-B(OAlk')$_2$ selected from boronic acid, boronic acid ester (e.g. (picolinato)boron ester) or alike, Pd catalyst (e.g. PdCl$_2$(dppf)DCM, Pd(PPh$_3$)$_4$ or alike); c) Het$^1$OH or Het$^2$OH, Mitsunobu reagents: e.g., triphenylphosphine, DIAD, base; d) RSO$_2$Cl, base; e) azide-forming reagent: NaN$_3$, LiN$_3$, or alike; f) triazole-forming reagent: e.g. R—C≡C—H, norbornadiene, or alike.

Another general route to compounds of the present invention featuring 3-isoxazolylamine group is illustrated in Scheme 3 below. Some synthetic methods to install a similar heterocyclic isoxazolyl group have been more generally described, for example, in International Patent Publication No. WO 2000/021960.

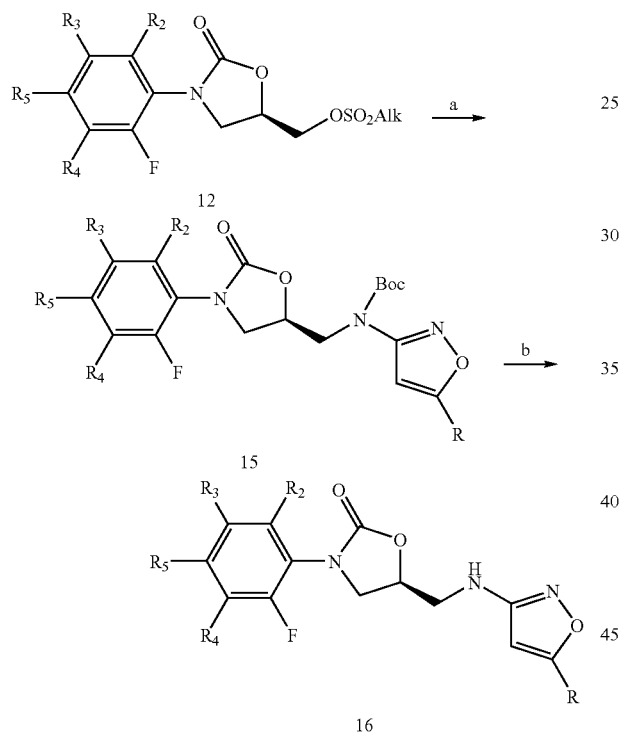

Scheme 3. General synthesis of 3-isoxazolylamine oxazolidinone derivatives. a) 3-(N-Boc-amino)-5-R-isoxazole; base: e.g. NaH, LiOBu-t, KOBu-t, tetramethylguanidine, or alike; c) acid: TFA or HCl solution in organic solvent, e.g. THF or dioxane); then base: NaHCO$_3$, TEA, or alike.

Optionally, the substituent R$^5$ can be installed into the requisite phenyl reagent prior to the oxazolidinone formation. Thus, various methods for synthesis of a dihydropyridone group derivatives have been generally described, for example, in publications Tetrahedron Lett., 1973, p. 5095; Tetrahedron Lett., 1991, p. 3643; Tetrahedron Lett., 1995, p. 3985; Tetrahedron Lett., 1995, p. 9449; Heterocycles, 1997, p. 57, Tetrahedron Lett., 1997, p. 7565.

Once the desired group R$^5$ is installed, the synthesis can be completed by general methods of any one of Schemes 1-3 or non-critical variations thereof, except that no coupling step to replace the Hal group for R$^5$ group is required (i.e. R$^5$ instead of Hal in the intermediate 1 of Scheme 1). For example, if the R$^5$ group is a dihydropyridone group, then compounds of structure II are obtained. When the group R$^5$ is a 6-member aryl or heteroaryl group, then compounds of structure III are obtained. Likewise, if R$^5$ group is a 2,4,5,6-tetrahydropyrrolo[3,4-c]pyrazolyl group, then compounds of structure IV are obtained.

Additional detailed synthetic schemes for the syntheses of specific compounds of the present invention are illustrated by methods described for Examples below.

EXAMPLES

Embodiments of the present invention are described in the following examples, which are meant to illustrate and not limit the scope of this invention. Common abbreviations well known to those with ordinary skills in the synthetic art used throughout. $^1$H NMR spectra (δ, ppm) are recorded in CDCl$_3$ unless specified otherwise. Mass-spectroscopy data for a positive ionization method are provided. Chromatography means silica gel chromatography unless specified otherwise. TLC means thin-layer chromatography. Unless specified otherwise, all reagents were either from commercial sources, or made by conventional methods described in available literature.

Example 1

Compound of Structure

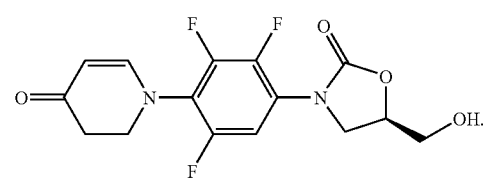

Scheme for the Compound of Example 1

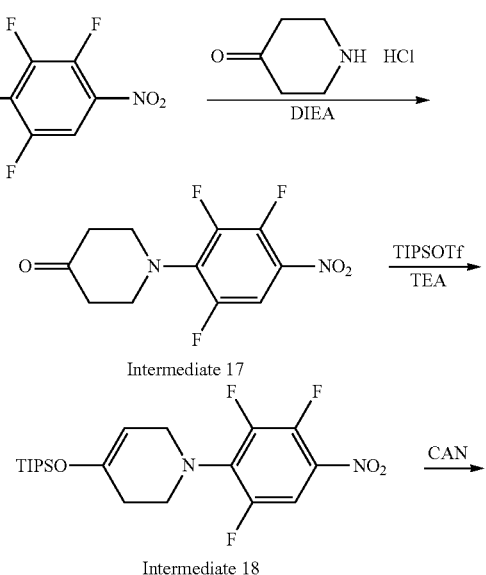

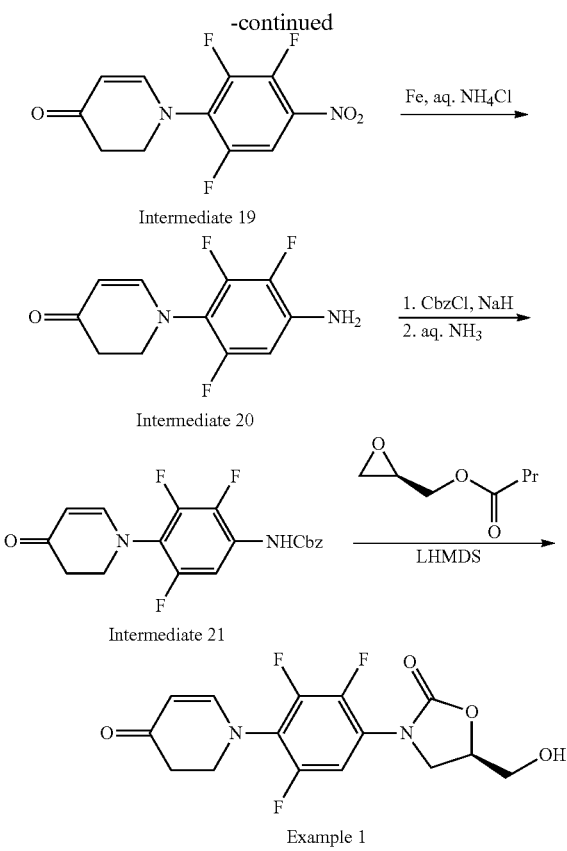

Intermediate 17. 2,3,4,5-Tetrafluoronitrobenzene (1.17 g, 6.0 mmol) in N-methylpiperidone (NMP; 25 mL) was added dropwise with stirring to 4-piperidone hydrochloride (0.84 g, 6.2 mmol) and N,N-diisopropyl-N-ethylamine (DIEA; 2.45 mL, 14.0 mmol) in NMP (20 mL) at ca. −10 to −5° C. under nitrogen. The mixture was allowed to warm up to r.t. and stirred o.n. The mixture was taken into EtOAc (ca. 100 mL), washed with 2% aq. citric acid (2×50 mL), water (10×50 mL), brine, and dried ($Na_2SO_4$). Solvent was removed under vacuum, and the crude product was washed with hexanes (4×20 mL) and dried. Yellow crystals. $^1$H NMR (400 MHz): 7.74 (m, 1H); 3.73 (t, J=6.0 Hz, 4H); 2.66 (t, J=6.0 Hz, 4H). MS (m/z): 275 [M+H].

Intermediate 18. Triethylamine (TEA; 5.6 mL, 43.87 mmol) was added to the Intermediate 17 (8.1 g, 29.56 mmol) in THF (120 mL) at 0° C., followed by triisopropylsilyl triflate (TIPSOTf; 10.7 g, 34.97 mmol). The mixture was allowed to warm up to r.t. over ca. 40 min, and stirred for another 2 h. Solvent was removed on a rotary evaporator. EtOAc (180 mL) was added, and the solution washed with 10% aq. $NaHCO_3$ (40 mL), brine (60 mL) and dried ($Na_2SO_4$). Solvent was removed under vacuum and to afford the product as a red-brownish oil. This was directly used at the next step without purification.

Intermediate 19. Ceric ammonium nitrate (CAN, 19.0 g, 34.65 mmol) was added portionwise with stirring to a solution of the Intermediate 18 (12.4 g, 28.80 mmol) in dry DMF (100 mL) at 0° C. The reaction mixture was allowed to warm up to r.t. and stirred for another 4 h. Most of solvent was removed under vacuum. Water (ca. 75 mL) was added and the mixture was extracted with EtOAc (2×100 mL). The combined organic layers were washed with brine and dried ($Na_2SO_4$). Solvent was removed and the residue purified by column chromatography (gradient 20% to 30% EtOAc in petroleum ether). The product was obtained as a yellow solid. $^1$H NMR (400 MHz): 7.84 (m, 1H); 7.14 (m, 1H); 5.43 (d, J=8.2 Hz, 1H); 4.06 (t, J=7.2 Hz, 2H); 2.74 (t, J=7.2 Hz, 2H). MS (m/z): 273 [M+H].

Intermediate 20. $NH_4Cl$ (0.33 g, 6.2 mmol) in water (5 mL) was added to a hot solution of the Intermediate 19 (0.170 g, 0.62 mmol) in EtOH (10 mL). Iron powder (0.173 g, 3.1 mmol) was added portionwise with stirring, and the mixture at ca. 100-105° C. for 50 min. The solution was filtered, and the precipitate washed with EtOH (5×10 mL). EtOH was removed under vacuum, and residue distributed between EtOAc (ca. 50 mL) and water (10 mL). Aq. layer was washed with EtOAc (3×20 mL), and combined organic layers were washed with water (3×7 mL), brine, and dried ($MgSO_4$). Solvent was removed under vacuum to afford the product as yellow crystals. $^1$H NMR (400 MHz): 7.03 (m, 1H); 6.36 (m, 1H); 5.19 (d, J=8.0 Hz, 1H); 4.12 (d, J=7.2 Hz, 2H); 3.80 (t, J=7.2 Hz, 2H); 2.66 (t, J=7.2 Hz, 2H). MS (m/z): 243 [M+H].

Intermediate 21. 60% NaH in mineral oil (1.4 g, 36.0 mmol) was added portionwise with stirring to the Intermediate 20 (2.9 g, 11.94 mmol) in THF (20 mL) at 0° C. under Ar, and the mixture was stirred at this temperature for 30 min. Benzyl chloroformate (4.1 g, 24.03 mmol) was added dropwise with stirring. The reaction mixture was allowed to warm up to r.t. and stirred o.n. The reaction was carefully quenched with water (10 mL), and THF was removed under vacuum. The residue was taken in DCM (80 mL). Organic layer was washed with brine (50 mL) and dried ($Na_2SO_4$). Solvent was removed under vacuum, and the residue dissolved with MeOH (40 mL). Aq. $NH_3$ (25 mL) was added with stirring, and the mixture was stirred at r.t. for 2 h. Solvent was removed under vacuum, and EtOAc (100 mL) was added. The organic layer was washed with brine and dried ($Na_2SO_4$). Solvent was removed under vacuum, and the residue purified by column chromatography (gradient 25% to 100% DCM/petroleum ether). White solid. $^1$H NMR (400 MHz): 7.95 (m, 1H); 7.41 (m, 6H); 7.07 (m, 2H); 5.28 (s, 2H); 3.88 (t, J=7.6 Hz, 2H); 2.69 (t, J=7.6 Hz, 2H). MS (m/z): 377 [M+H].

Compound of Example 1. 1.06M Lithium hexamethyldisilylamide (LHMDS; 3.0 mL, 3.18 mmol) in THF was added dropwise with stirring to a solution of the Intermediate 21 (1.0 g, 2.66 mmol) in THF (8.0 mL) at −78° C., and the mixture was stirred at this temperature for 30 min. (R)-Glycidyl butyrate (0.8 mL, 5.55 mmol) was added dropwise, and the mixture was allowed to warm up to r.t. and stirred o.n. The reaction was quenched with 10% aq. $NH_4Cl$ (15 mL), and THF was removed under vacuum. The residue was extracted with EtOAc (2×30 mL). Combined organic layers were washed with brine and dried ($Na_2SO_4$). Solvent was removed under vacuum. MeOH (5 mL) and 20% aqueous $Cs_2CO_3$ (5 mL) were added, and the mixture was stirred at r.t. for 20 min. The mixture was taken into EtOAc (50 mL), washed with water (2×15 mL), brine, and dried ($Na_2SO_4$). Solvent was removed under vacuum and the crude product was purified by column chromatography (2% methanol/DCM). Off-white solid. $^1$H NMR (400 MHz): 7.44 (m, 1H); 7.10 (d, J=7.6 Hz, 1H); 5.33 (d, J=8.0 Hz, 1H); 4.84 (m, 1H); 4.19 (m, 1H); 4.08 (m, 2H); 3.92 (t, J=7.4 Hz, 2H); 3.81 (dd, J=12.4, 3.2 Hz, 1H); 2.71 (t, J=7.4 Hz, 2H); 2.14 (br, 1H). MS (m/z): 343 [M+H].

Example 2

Compound of Structure

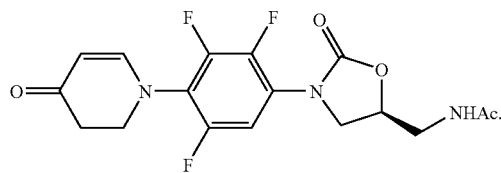

Scheme for Compound of Example 2

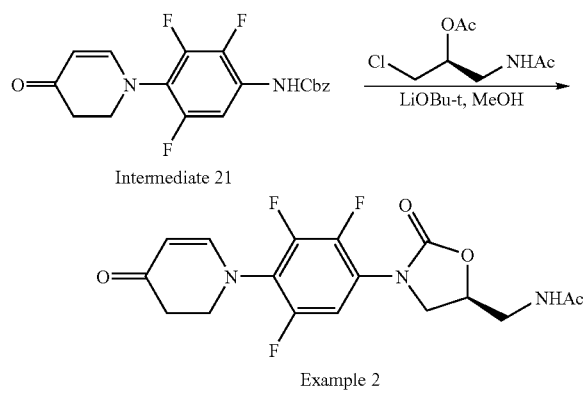

Compound of Example 2. 1M LiOBu-t in THF (0.96 mmol) was added to Intermediate 21 (90 mg, ca. 0.24 mmol) in DMF (0.18 mL) and MeOH (0.029 mL) at −10° C. under $N_2$, followed by N-[(2S)-2-acetoxy-3-chloropropyl]acetamide (139 mg, 0.72 mmol; prepared as described in Org. Proc. Res. Develop., 2003, p. 533). The mixture was allowed to warm up to r.t. over ca. 5 h and stirred o.n. The mixture was quenched with 10% aq. $NH_4Cl$ (ca. 1 mL) and extracted with EtOAc (ca. 3×10 mL). Combined organic layers were washed with brine and dried ($MgSO_4$). Solvent was removed under vacuum and the product isolated by column chromatography (eluent: ca. 2-3% MeOH in DCM). Off-white crystals. $^1$H NMR (300 MHz): 7.36-7.27 (m, 1H), 7.27-7.05 (m, 1H), 5.95 (br. t, 1H), 5.31 (d, J=8.1 Hz, 1H); 4.86 (m, 1H), 4.18-3.87 (m, 1H), 3.94-3.87 (m, 4H), 3.71 (m, 1H), 2.71 (t, J=7.5 Hz, 2H). MS (m/z): 384 [M+H].

Example 3

Compound of Structure

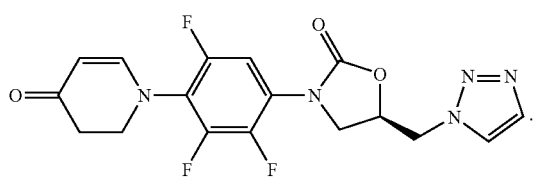

Scheme for Compound of Example 3

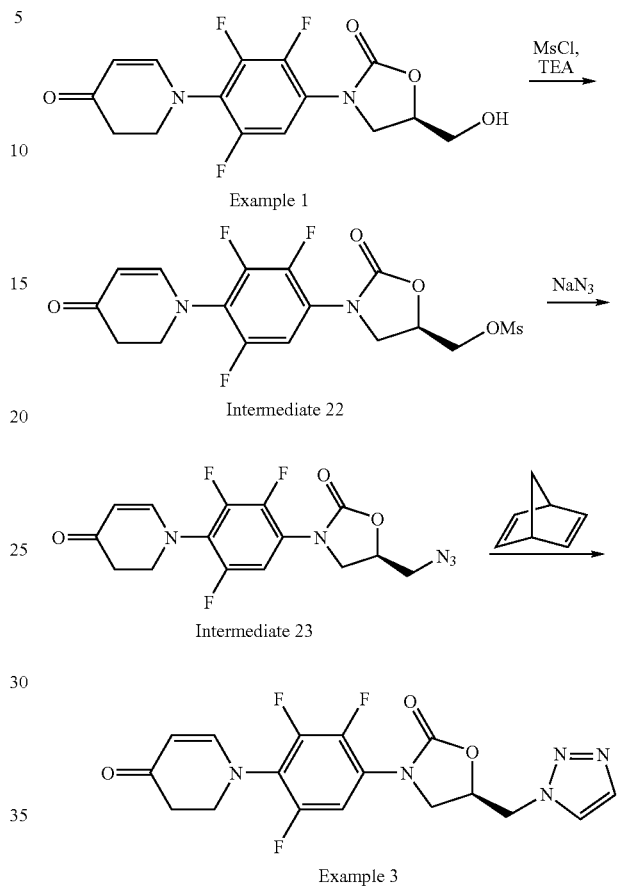

Intermediate 22. Methylsulfonyl chloride (MsCl; 79 uL, 1.00 mmol) was added dropwise with stirring to the compound of Example 1 (290 mg, 0.85 mmol) and TEA (177 uL, 1.27 mmol, 1.50 equiv.) in DCM (5 mL) at ca. 0° C. The mixture was stirred for 20 min and allowed to warm up to r.t. The reaction mixture distributed between water and the DCM. Aq. layer was extracted with DCM (2×10 mL), and the combined organic layers washed with brine and dried ($Na_2SO_4$). Solvent was removed under vacuum to afford the product that was used for the next step without purification.

Intermediate 23. A mixture of the Intermediate 22 (567 mg, 1.35 mmol) and $NaN_3$ (438 mg, 6.75 mmol) in DMF (5 mL) was stirred at 55° C. o.n. After cooling to r.t., water (15 mL) was added, and the reaction mixture was extracted with DCM (3×30 mL). Combined organic layers were washed with brine (30 ml) and dried ($Na_2SO_4$). Solvent was removed under vacuum to afford the product as a light yellow solid. This was used directly for the next step without further purification.

Compound of Example 3. A mixture of the Intermediate 23 (785 mg, 2.14 mmol) and bicyclo[2.2.1]hepta-2,5-diene (2.2 mL, 21.4 mmol) in 1,4-dioxane (22 mL) under $N_2$ was heated at 100° C. for 3 h. Most of volatiles were removed under vacuum, and the residue was purified by column chromatography (1% MeOH/DCM). Thus isolated product was recrystallized from MeOH. White solid. $^1$H NMR (400 MHz): 7.83 (s, 2H), 7.05 (m, 2H), 5.30 (d, J=8 Hz, 1H), 5.16 (m, 1H), 4.83

(d, J=3.6 Hz, 2H), 4.33 (m, 1H), 4.06 (m, 1H), 3.91 (t, J=14.8 Hz, 2H), 2.69 (t, J=14.8 Hz, 2H). MS (m/z): 394 [M+H].

Example 4

Compound of Structure

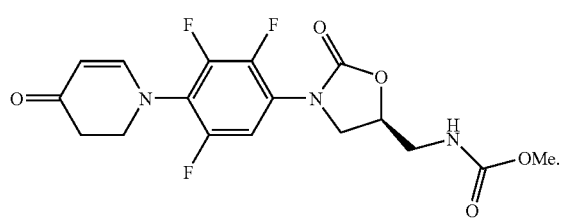

Scheme for Compound of Example 4

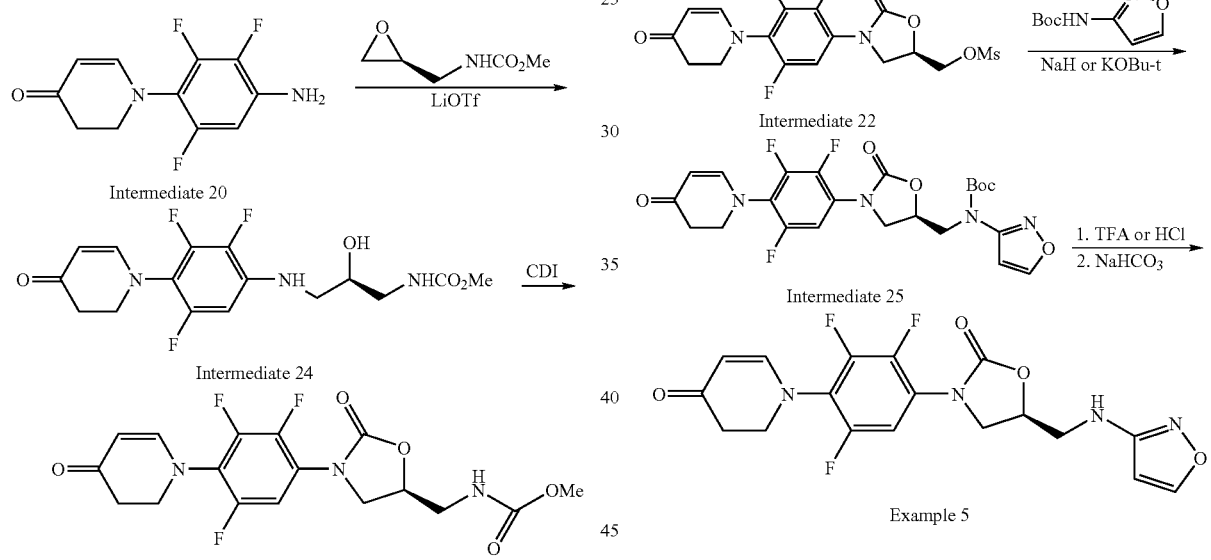

Example 4

Intermediate 24. A mixture of the Intermediate 20 (500 mg, 2.1 mmol), (S)-methyl oxiran-2-ylmethylcarbamate (270 mg, 2.1 mmol), and LiOTf (970 mg, 6.2 mmol) in MeCN (4 mL) was stirred at 100° C. o.n. Solvent was removed under vacuum, and water (5 mL) was added. The mixture was extracted with EtOAc (8 mL×3), and combined organic layers dried (Na$_2$SO$_4$). Solvent was removed under vacuum, and the residue purified by preparative TLC (28% ethyl acetate/DCM) to afford the product as a light yellow solid.

Compound of Example 4. N,N'-Carbonyldiimidazole (CDI; 0.16 g, 0.97 mmol) was added to a solution of the Intermediate 24 (181 mg, 0.48 mmol) in MeCN (2 ml), and the mixture was stirred at 80° C. under Ar o.n. Solvent was removed under vacuum, and the product purified by preparative TLC (5% methanol/DCM). The product was obtained as a white solid. $^1$H NMR (400 MHz, DMSO-d$_6$): 7.60 (m, 2H), 7.51 (d, J=7.6 Hz, 1H), 5.08 (d, J=7.6 Hz, 1H), 4.79 (m, 1H), 4.13 (t, J=8.8 Hz, 1H), 3.88 (m, 3H), 3.55 (s, 3H), 3.38 (overlapped with DMSO, 2H), 2.48 (overlapped with DMSO-d$_6$, 2H). MS (m/z): 400 [M+H].

Example 5

Compound of Structure

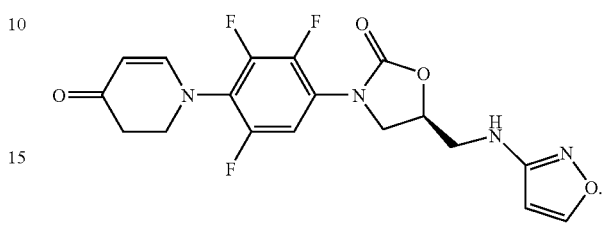

Scheme for Compound of Example 5

Intermediate 25.

Method A. A solution of tert-butyl isoxazol-3-ylcarbamate (187 mg, 1.00 mmol) in DMF (1 mL) was added dropwise with stirring to a suspension of NaH (60% in mineral oil, 48 mg, 1.20 mmol) in DMF (2 mL). The mixture was stirred under N$_2$ for 15 min. at 35° C. The Intermediate 22 (357 mg, 0.85 mmol) in DMF (1 mL) was added, and the mixture was stirred at 50° C. for 1.5 h. The reaction mixture was taken into EtOAc (30 mL), washed with 10% aq. NH$_4$Cl (2×15 mL), brine, and dried (Na$_2$SO$_4$). Solvent was removed under vacuum and the crude material was purified by column chromatography (2% MeOH/DCM) to afford the product as a light yellow solid.

Method B. A solution of tert-butyl isoxazol-3-ylcarbamate (694 mg, 3.8 mmol) in DMF (3 mL) was added dropwise with stirring to Bu$^t$OK (439 mg, 3.8 mmol) in DMF (3 mL) at 0° C. The mixture was warmed up to r.t. and stirred for 30 min. The Intermediate 22 (1.34 g, 3.2 mmol) in DMF (6 mL) mL) was added, and the mixture was stirred at 35° C. for 2 h. The reaction was quenched with saturated aq. NH$_4$Cl solution (10 mL), and isolation performed just as described above for Method A to afford the product as a light yellow solid. $^1$H NMR (400 MHz): 8.28 (s, 1H), 7.44 (m, 1H), 7.09 (d, J=7.6 Hz, 1H), 7.00 (s, 1H), 5.32 (d, J=7.6 Hz, 1H), 5.15 (m, 1H), 4.44 (m, 1H), 4.20 (m, 2H), 3.94 (m, 3H), 2.70 (t, J=7.4 Hz, 2H), 1.45 (s, 9H). MS (m/z): 509 [M+H].

Compound of Example 5

Method A. TFA (2.0 mL) was added dropwise to the solution of the Intermediate 25 (310 mg, 0.61 mmol) in 1,2-dichloroethane (DCE; 2 mL) at 0° C., and the solution was stirred at 0° C. for 30 min. Volatiles were removed under vacuum, and the residue taken into EtOAc (30 mL). The solution was washed with saturated NaHCO$_3$ solution (2×15 mL), brine, and dried (Na$_2$SO$_4$). Solvent was removed under vacuum and the crude product was purified by column chromatography (3% MeOH/DCM). Light-yellow solid.

Method B. 4M HCl in THF (56 mL) was added dropwise to the Intermediate 25 (3.0 g, 5.9 mmol) at 0° C. Water (0.59 mL) was added, and the solution was stirred at r.t. for 2 h. Most of volatiles were removed under vacuum, the residue taken into water (30 mL) and sat. aq. NaHCO$_3$ (15 mL), and pH adjusted to ca. 8. After stirring for 15 min, the mixture was extracted with EtOAc (3×60 mL). Combined organic layers were washed with brine (2×30 mL), and dried (Na$_2$SO$_4$). Solvent was removed under vacuum. The residue was re-dissolved in 2% MeOH in DCM (3 mL), and passed through a short pad of silica, eluting the product with 2% MeOH in DCM. Light-yellow solid. $^1$H NMR (400 MHz, DMSO-d$_6$): 8.41 (d, J=1.6 Hz, 1H); 7.57 (m, 1H), 7.50 (d, J=8.0 Hz, 1H), 6.58 (t, J=5.8 Hz, 1H), 6.02 (d, J=1.6 Hz, 1H), 5.08 (d, J=8.0 Hz, 1H), 4.90 (m, 1H), 4.17 (t, J=8.6 Hz, 1H), 3.86 (m, 3H), 3.48 (t, J=5.6 Hz, 2H), 2.49 (m, overlapped with DMSO-d$_6$, 2H). MS (m/z): 409 [M+H].

Example 6

Compound of Structure

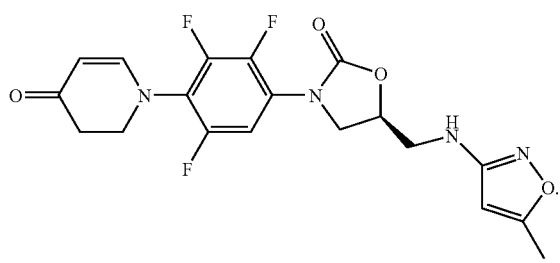

Scheme for Compound of Example 6

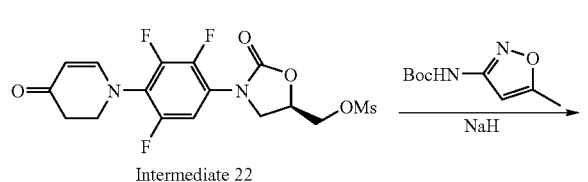

Intermediate 22

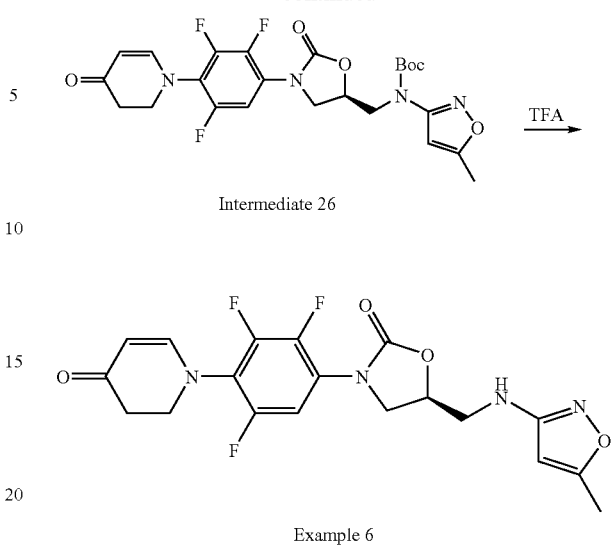

Intermediate 26

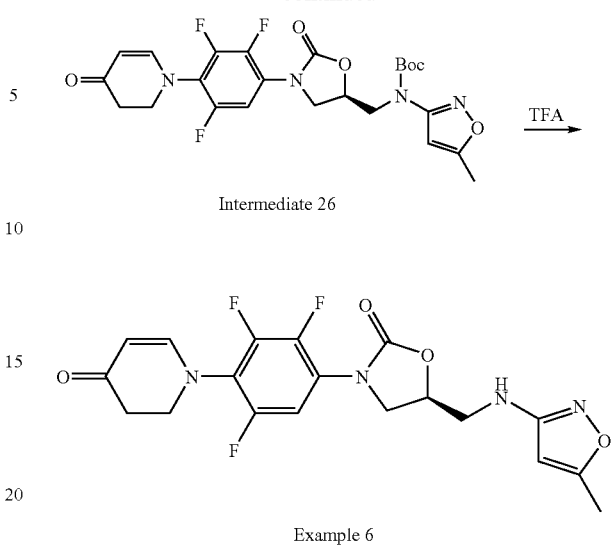

Example 6

Intermediate 26. NaH (60% in mineral oil, 7 mg, 0.18 mmol) was added with stirring to tert-butyl 5-methylisoxazol-3-ylcarbamate (34 mg, 0.17 mmol) in DMF (1 mL) at 0° C. The mixture was stirred at this temperature for 15 min, and then at 35° C. for 30 min. The Intermediate 22 (60 mg, 0.14 mmol) in DMF (1.00 mL) was added, and the mixture was stirred at 50° C. for 1.5 h. The reaction mixture was taken into EtOAc (30 mL), washed with 10% aq. NH$_4$Cl (2×15 mL), brine, and dried (Na$_2$SO$_4$). Solvent was removed under vacuum and the crude product was purified by column chromatography (2% MeOH/DCM) to afford the product that was used for the next step without purification.

Compound of Example 6. The synthetic step was performed just as described for the Compound of Example 5, except using the Intermediate 26 from above step instead of the Intermediate 25. The crude product was purified by preparative TLC (5% methanol/DCM). Light-yellow solid. $^1$H NMR (400 MHz, DMSO-d$_6$): 7.57 (m, 1H), 7.49 (d, J=8.0 Hz, 1H), 6.47 (t, J=6.0 Hz, 1H), 5.70 (s, 1H), 5.07 (d, J=8.0 Hz, 1H), 4.92 (m, 1H), 4.16 (t, J=8.8 Hz, 1H), 3.87 (m, 3H), 3.43 (t, J=5.6 Hz, 2H), Example 7

Compound of Structure

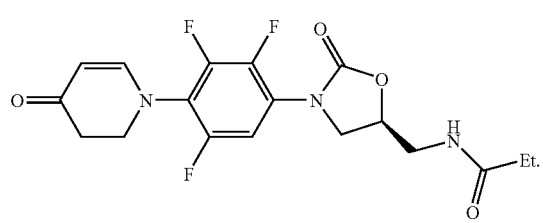

41

Scheme for Compound of Example 7

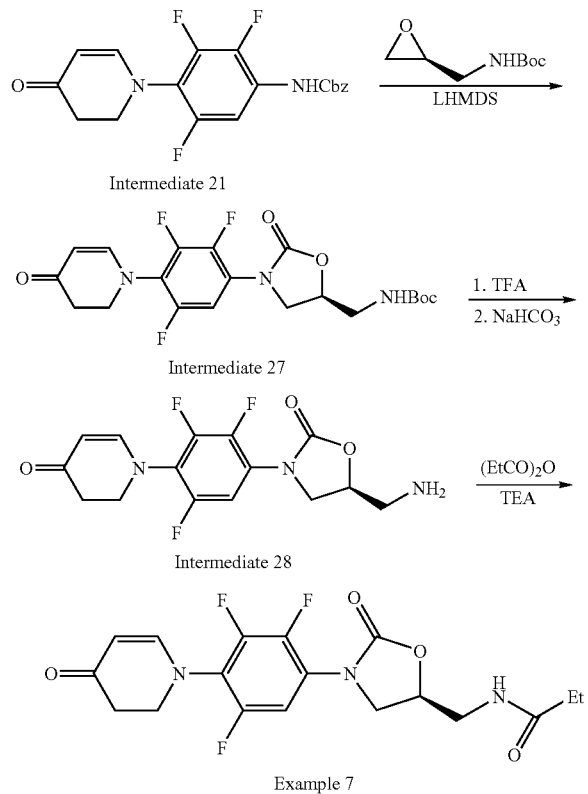

Intermediate 27. 1.06M Lithium hexamethyldisilylamide in THF (LHMDS; 0.45 mL, 0.48 mmol) was added dropwise with stirring to a solution of the Intermediate 21 (151 mg, 0.40 mmol) in THF (2 mL) under $N_2$ at −78° C. After ca. 30 min, a solution of (S)-tert-butyl oxiran-2-ylmethylcarbamate (139 mg, 0.80 mmol) in THF (1.5 mL) was added dropwise with stirring. The mixture was allowed to warm up to r.t. and stirred o.n. Saturated aq. $NH_4Cl$ solution (10 mL) was added, and the solution extracted with EtOAc (3×10 mL). Combined organic layers were washed with brine and dried ($Na_2SO_4$). The product was isolated by preparative TLC (95% DCM/MeOH) as yellow oil that was used directly for the next step.

Intermediate 28. TFA (0.2 mL) was added to the Intermediate 27 (102 mg, 0.23 mmol) in DCE (2 mL) at 0° C., and the solution was kept at this temperature for ca. 15 min. The reaction was quenched with 5% aq. $NaHCO_3$ and extracted with DCM (2×10 mL). The combined organic layers were dried ($Na_2SO_4$), and the solvent was removed in vacuo to afford the product as a pale yellow solid.

Compound of Example 7. TEA (139 μL, 1.0 mmol) was added to a solution of the Intermediate 28 in DCM (2 mL) at 0° C., followed by propionic anhydride (52 μl, 0.40 mmol). The reaction mixture was stirred at 0° C. for 30 min. Water (2 mL) was added, and the mixture extracted with DCM (3×5 mL). Combined organic layers were washed with brine and dried ($Na_2SO_4$). The crude material was purified by preparative TLC (5% MeOH/DCM) to afford the product as a white solid. $^1$HNMR (400 MHz): 7.31 (m, 1H); 7.07 (d, J=7.6 Hz, 1H); 6.36 (t, J=12.4 Hz, 1H); 5.29 (d, J=8.0 Hz, 1H); 4.86 (m, 1H); 4.15 (t, J=17.6 Hz, 1H); 3.91 (t, J=14.8 Hz, 3H); 3.70 (m, 2H); 2.69 (t, J=15.2 Hz, 2H); 2.30 (m, 2H); 3.21 (t, J=14.8 Hz, 3H). MS (m/z): 398 [M+H].

Example 8

Compound of Structure

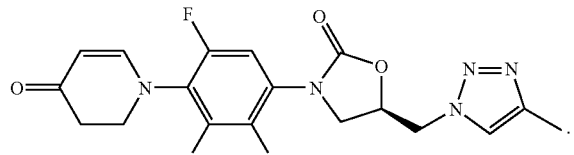

Scheme for Compound of Example 8

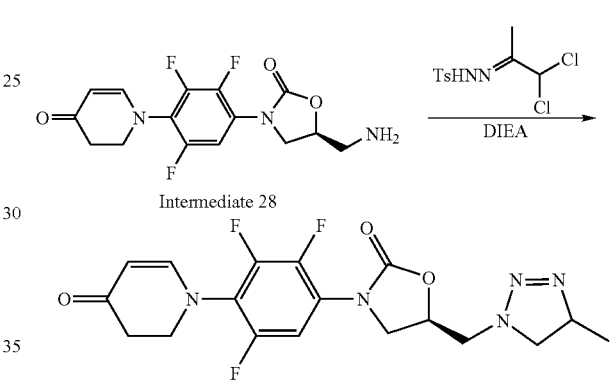

Compound of Example 8. N'-(1,1-Dichloropropan-2-ylidene)-4-methylbenzenesulfonohydrazide (106 mg, 0.36 mmol) was added with stirring to a solution of the Intermediate 28 (82 mg, 0.24 mmol) and DIEA (200 μL, 1.2 mmol) in MeOH (1 mL) under Ar at 0° C. The reaction mixture was allowed to warm up to r.t. and stirred for 3 h. The solvent was removed under vacuum and the residue taken into DCM. Resulting mixture was washed with water and dried ($Na_2SO_4$). The filtrate was concentrated under vacuum and the residue was purified by preparative TLC (eluent 6.7% MeOH/DCM). The product was isolated as a white solid. $^1$H NMR (400 MHz, DMSO-$d_6$): 7.88 (s, 1H), 7.50 (d, J=8.0 Hz, 1H), 7.43 (m, 1H), 5.18 (m, 1H), 5.08 (d, J=7.6 Hz, 1H), 4.78 (d, J=4.4 Hz, 2H), 4.26 (t, J=8.8 Hz, 1H), 3.87 (m, 3H) 2.48 (m, overlapped with DMSO-$d_6$, 2H); 2.25 (s, 3H). MS (m/z): 408 [M+H].

Example 9

Compound of Structure

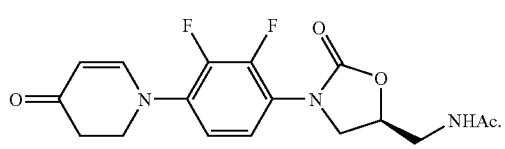

Scheme for Compound of Example 9

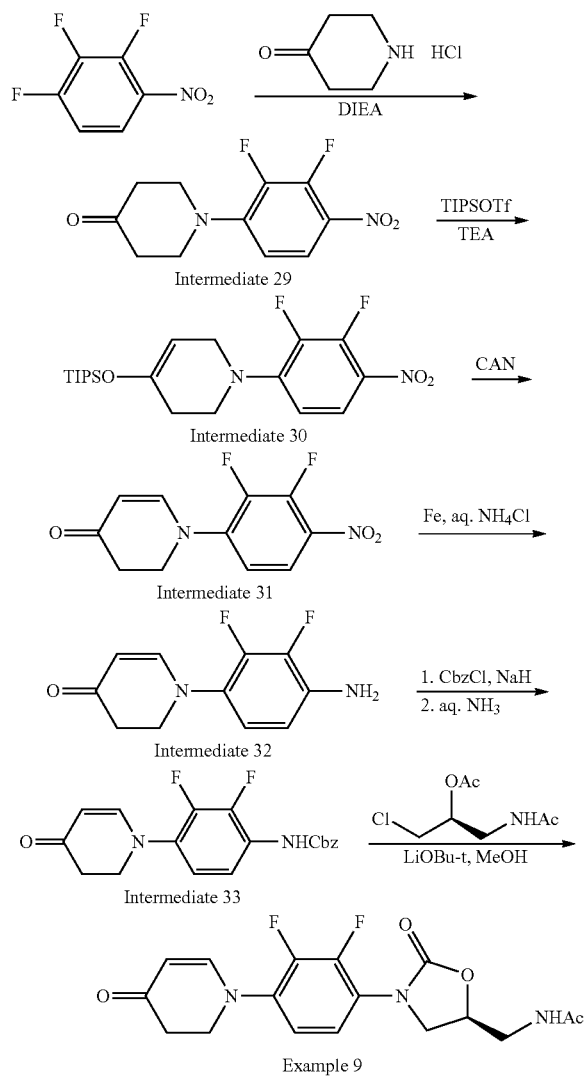

Intermediate 29. 2,3,4-Trifluoronitrobenzene (5.5 g, 30.8 mmol) was added dropwise with stirring to 4-piperidone hydrochloride (4.6 g, 33.9 mmol) and DIEA (9.2 g, 71.2 mmol) in NMP (50 mL) at ca. −5° C. under Ar. The mixture was allowed to warm up to r.t. and stirred o.n. The mixture was cooled in an ice bath and quenched with ice water (ca. 300 mL). The precipitate yellow product was filtered off, washed with water and dried under vacuum. This was used for the next step without further purification.

Intermediate 30. TEA (5.3 mL, 40.7 mmol) was added to the Intermediate 29 (7.1 g, 27.7 mmol) in THF (80 mL) at 0° C., followed by triisopropylsilyl triflate (9.5 g, 32.5 mmol). The mixture was allowed to warm up to r.t. over ca. 40 min, and stirred for another 2 h. Solvent was removed on a rotary evaporator. EtOAc (120 mL) was added, and the solution washed with 10% aq. $NaHCO_3$ (25 mL), brine (60 mL) and dried ($Na_2SO_4$). Solvent was removed under vacuum and to afford the product as a red-brownish oil. This was used at the next step without purification.

Intermediate 31. CAN (17.7 g, 32.3 mmol) was added portionwise with stirring to a solution of the Intermediate 30 (11.1 g, 26.9 mmol) in dry DMF (100 mL) at 0° C. The reaction mixture was allowed to warm up to r.t. and stirred for another 4 h. Most of solvent was removed under vacuum. Water (ca. 75 mL) was added and the mixture was extracted with ethyl acetate (2×100 mL). The combined organic layers were washed with brine and dried ($Na_2SO_4$) Solvent was removed and the residue purified by column chromatography (gradient 20% to 30% EtOAc in petroleum ether). The product was obtained as a yellow solid (5.3 g, 78%). This was used without purification for the next step.

Intermediate 32. $NH_4Cl$ (4.5 g, 83.3 mmol) in water (10 mL) was added to a hot solution of the Intermediate 31 (1.8 g, 7.1 mmol) in EtOH (40 mL). Iron powder (5.0 g, 89.7 mmol) was added portionwise with stirring, and the mixture at ca. 100-105° C. for 40 min. The solution was filtered through Celite, and the precipitate washed with EtOAc. EtOAc was removed under vacuum, and residue distributed between EtOAc and water. Aq. layer was washed with EtOAc (2×60 mL), and combined organic layers were washed with brine and dried ($Na_2SO_4$). Solvent was removed under vacuum, and the resulting product used for the next step without further purification.

Intermediate 33. 60% NaH in mineral oil (0.33 g, 13.7 mmol) was added portionwise with stirring to the Intermediate 32 (1.1 g, 4.9 mmol) in THF (20 mL) at 0° C. under Ar, and the mixture was stirred at this temperature for 30 min. Benzyl chloroformate (1.25 g, 7.3 mmol) was added dropwise with stirring. The reaction mixture was allowed to warm up to r.t. and stirred o.n. The reaction was carefully quenched with water (10 mL), and THF was removed under vacuum. The residue was taken in DCM (80 mL). Organic layer was washed with brine (50 mL) and dried ($Na_2SO_4$). Solvent was removed under vacuum, and the residue dissolved with MeOH (20 mL). Aq. $NH_3$ (10 mL) was added with stirring, and the mixture was stirred at r.t. for 2 h. Solvent was removed under vacuum, and EtOAc (100 mL) was added. The organic layer was washed with brine and dried ($Na_2SO_4$). Solvent was removed under vacuum, and the residue was purified by column chromatography (gradient 25% to 100% DCM/petroleum ether). To afford the product as a white solid.

Compound of Example 9. 2.2M LiOBu-t in THF (0.36 mL. 0.79 mmol) was added to Intermediate 33 (70 mg, 0.20 mmol) in DMF (1.0 mL) and MeOH (0.024 mL, 0.60 mmol) at 0° C. under Ar, followed by N-[(2S)-2-acetoxy-3-chloropropyl]acetamide (193.6 mg, 1.00 mmol; prepared as described in Org. Proc. Res. Develop., 2003, p. 533). The mixture was allowed to warm up to r.t. over ca. 5 h and stirred o.n. The mixture was quenched with 10% aq. $NH_4Cl$ and extracted with EtOAc (ca. 2×20 mL). Combined organic layers were washed with brine and dried ($Na_2SO_4$). Solvent was removed under vacuum and the product isolated by preparative TLC (eluent: 5% MeOH in DCM). White crystals. $^1$H NMR (400 MHz): 7.30 (d, J=7.6 Hz, 1H), 7.25 (d, J=8.0 Hz, 1H), 6.96 (d, J=7.6 Hz, 1H), 5.31 (d, J=8.0 Hz, 1H), 4.84 (m, 1H), 4.09 (m, 1H), 3.97 (t, J=12.8 Hz, 2H), 3.84 (m, 1H), 3.70 (m, 1H), 2.68 (t, J=12.8 Hz, 2H). MS (m/z): 366 [M+H].

Example 10

Compound of Structure

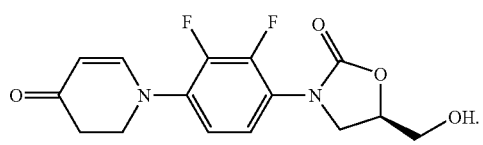

Scheme for Compound of Example 10

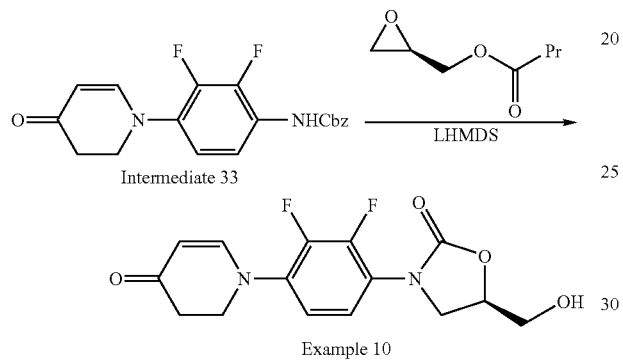

Compound of Example 10. 1.06M LHMDS (3.0 mL, 3.18 mmol) in THF was added dropwise with stirring to a solution of the Intermediate 33 (1.0 g, 2.79 mmol) in THF (8.0 mL) at −78° C., and the mixture was stirred at this temperature for 30 min. (R)-Glycidyl butyrate (0.8 mL, 5.55 mmol) was added dropwise, and the mixture was allowed to warm up to r.t. and stirred o.n. The reaction was quenched with 10% aq. NH$_4$Cl (15 mL), and THF was removed under vacuum. The residue was extracted with EtOAc (2×30 mL). Combined organic layers were washed with brine and dried (Na$_2$SO$_4$). Solvent was removed under vacuum. MeOH (5 mL) and 20% aqueous Cs$_2$CO$_3$ (5 mL) were added, and the mixture was stirred at r.t. for 20 min. The mixture was taken into EtOAc (50 mL), washed with water (2×15 mL), brine, and dried (Na$_2$SO$_4$). Solvent was removed under vacuum and the crude product was purified by column chromatography (2% methanol/DCM). White solid. $^1$H NMR (400 MHz): 7.40 (m, 1H), 7.26 (dd, J=1.6 and 8.0 Hz, 1H), 6.97 (m, 1H), 5.33 (d, J=7.6 Hz, 1H), 4.85 (m, 1H), 4.09 (m, 1H), 4.15 (t, J=8.8 Hz, 1H), 4.06 (m, 1H), 3.99 (m, 2H), 3.82 (m, 1H), 2.70 (m, 2H), 2.15 (br. s, 1H). MS (m/z): 325 [M+H].

Example 11

Compound of Structure

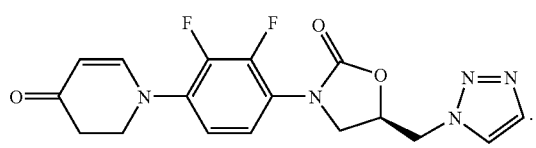

Scheme for Compound of Example 11

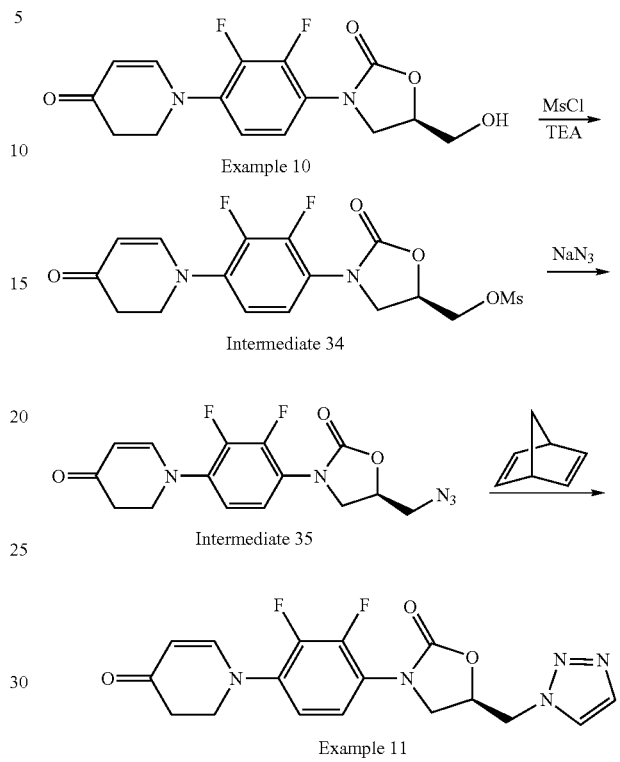

Intermediate 34. Methylsulfonyl chloride (MsCl; 79 uL, 1.00 mmol) was added dropwise with stirring to the compound of Example 10 (200 mg, 0.62 mmol) and TEA (220 mg, 2.1 mmol) in DCM (5 mL) at ca. 0° C. The mixture was stirred for 20 min and allowed to warm up to r.t. The reaction mixture distributed between water and the DCM. Aq. layer was extracted with DCM (2×10 mL), and the combined organic layers washed with brine and dried (Na$_2$SO$_4$). Solvent was removed under vacuum to afford the product that was used for the next step without purification.

Intermediate 35. A mixture of the Intermediate 34 (120 mg, 0.31 mmol) and NaN$_3$ (110 mg, 1.70 mmol) in DMF (5 mL) was stirred at 55° C. o.n. After cooling to r.t., water (15 mL) was added, and the reaction mixture was extracted with DCM (3×30 mL). Combined organic layers were washed with brine (30 ml) and dried (Na$_2$SO$_4$). Solvent was removed under vacuum to afford the product as a light yellow solid. This was used directly for the next step without further purification.

Compound of Example 11. A mixture of the Intermediate 35 (80 mg, 0.3 mmol) and bicyclo[2.2.1]hepta-2,5-diene (240 mg, 2.5 mmol) in 1,4-dioxane (7 mL) under N$_2$ was heated at 100° C. for 3 h. Most of volatiles were removed under vacuum, and the residue was purified by column chromatography (1% MeOH/DCM). White solid. $^1$H NMR (400 MHz): 7.83 (d, J=9.2 Hz, 2H), 7.22 (d, J=9.2 Hz, 1H), 7.02 (m, 1H), 6.89-7.00 (m, 1H), 5.31 (d, J=8.0 Hz, 1H, 5.14-5.11 (m, 1H), 4.84 (d, J=3.6 Hz, 2H), 4.26 (t, J=18.4 Hz, 1H), 3.98 (m, 3H), 2.68 (t, J=14.8 Hz, 2H). MS (m/z): 376 [M+H].

Example 12

Compound of Structure

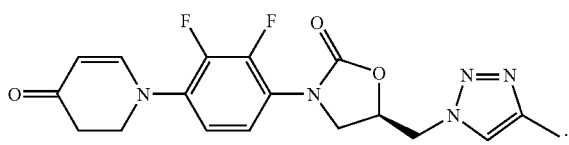

Scheme for Compound of Example 12

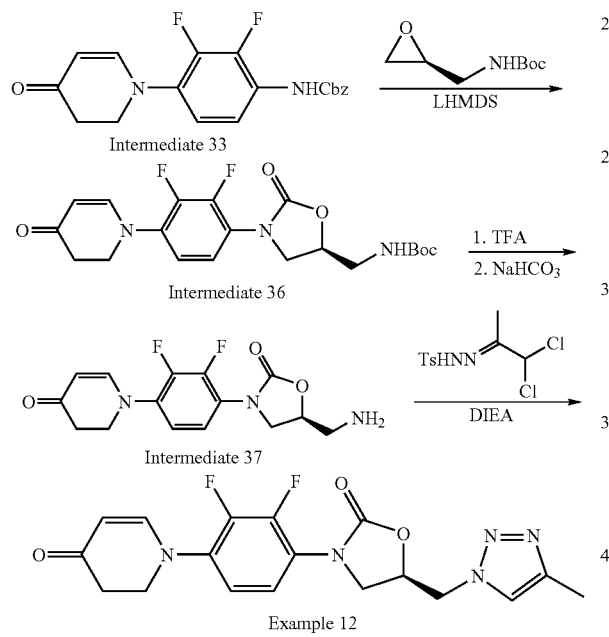

Intermediate 36. 1.06M LHMDS in THF (4.6 mL, 4.90 mmol) was added dropwise with stirring to a solution of the Intermediate 33 (700 mg, 1.96 mmol) in THF (5 mL) under $N_2$ at −40° C. After ca. 30 min, (S)-tert-butyl oxiran-2-ylmethylcarbamate (407 mg, 2.35 mmol) was added with stirring. The mixture was allowed to warm up to r.t. and stirred o.n. Water (5 mL) was added, and the solution extracted with EtOAc (3×8 mL). Combined organic layers were washed with brine and dried ($Na_2SO_4$). The product was isolated by preparative TLC (20% EtOAc/DCM) as a white solid. This was used directly for the next step.

Intermediate 37. TFA (1.0 mL) was added to the Intermediate 36 (200 mg, 0.47 mmol) in DCE (4 mL) at 0° C., and the solution was kept at r.t. for 2 h. Volatiles were removed under vacuum with a repeated addition of extra DCE (ca. 3 times). Resulted TFA salt was quenched with 5% aq. $NaHCO_3$ and extracted with DCM (3×10 mL). The combined organic layers were dried ($Na_2SO_4$), and the solvent was removed in vacuo to afford the product as an oil.

Compound of Example 12. N'-(1,1-Dichloropropan-2-ylidene)-4-methylbenzenesulfonohydrazide (120 mg, 0.93 mmol) was added with stirring to a solution of the Intermediate 37 (100 mg, 0.31 mmol) and DIEA (150 mg, 0.45 mmol) in MeOH (4 mL) under Ar at 0° C. The reaction mixture was allowed to warm up to r.t. and stirred for 3 h. The solvent was removed under vacuum and the residue taken into DCM. Resulting mixture was washed with water and dried ($Na_2SO_4$). The filtrate was concentrated under vacuum and the residue was purified by preparative TLC (5% MeOH/DCM). The product was isolated as a white solid. $^1H$ NMR (300 MHz): 7.54 (d, J=0.6 Hz, 1H), 7.23 (dd, J=2.1 and 7.8 Hz, 1H), 7.04 (m, 1H), 6.91 (m, 1H), 5.31 (d, J=8.1 Hz, 1H), 5.12 (m, 1H), 4.74 (d, J=4.2 Hz, 2H), 4.25 (m, 1H), 3.99 (m, 3H), 2.69 (m, 2H), 2.40 (d, J=0.6 Hz, 3H). MS (m/z): 390 [M+H].

Example 13

Compound of Structure

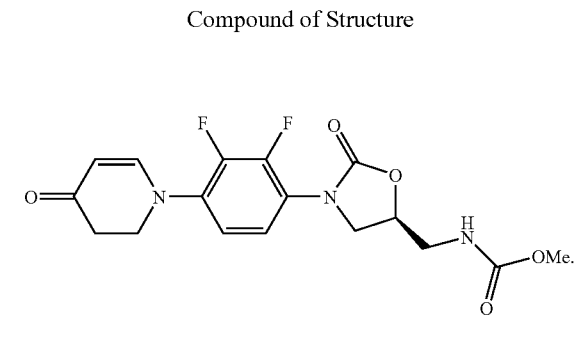

Scheme for Compound of Example 13

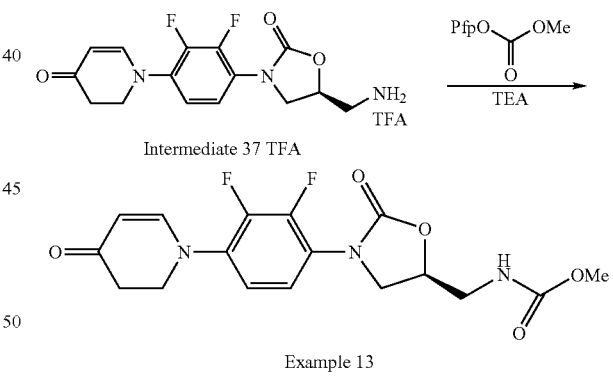

Compound of Example 13. Pentafluorophenyl methyl carbonate (115 mg, 0.48 mmol) was added with stirring to the Intermediate 37 (TFA salt; 138 mg, 0.32 mmol) and TEA (220 µL, 1.60 mmol) in MeCN (2 mL) at ca. 0° C. The mixture was stirred at this temperature for 15 min, quenched with sat. aq. $NH_4Cl$ solution, and extracted with EtOAc (2×10 mL). Combined organic layers were washed with brine and dried ($Na_2SO_4$). Solvent was removed under vacuum, and the residue purified by column chromatography (4.8% methanol/DCM) to afford the product was obtained as a white solid. $^1H$ NMR (400 MHz): 7.36 (t, J=7.6 Hz, 1H), 7.26 (dd, J=6.0, 2.0 Hz, 1H), 6.98 (d, J=8.4 Hz, 1H), 5.34 (d, J=7.6 Hz, 1H), 5.15 (m, 1H), 4.86 (m, 1H), 4.12 (t, J=8.8 Hz, 1H), 3.99 (t, J=7.2

Hz, 2H), 3.90 (dd, J=15.2, 6.8 Hz, 1H), 3.73 (s, 3H), 3.63 (m, 2H), 2.71 (t, J=7.6 Hz, 2H). MS (m/z): 382 [M+H].

Example 14

Compound of Structure

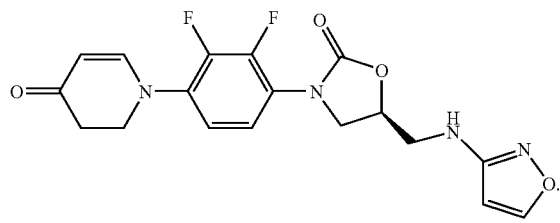

Scheme for Compound of Example 14

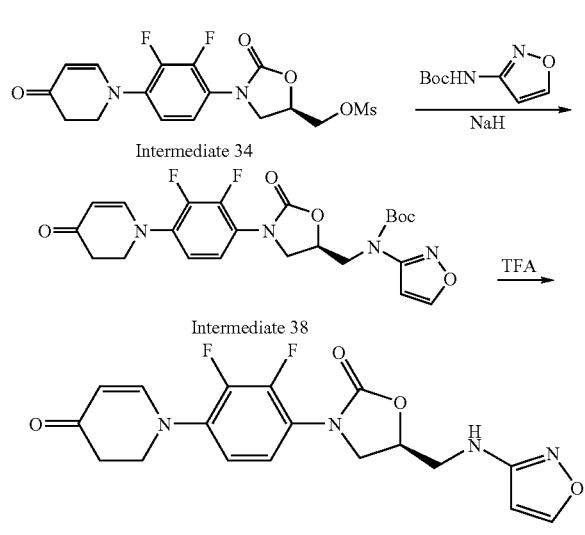

Intermediate 38. A solution of tert-butyl isoxazol-3-ylcarbamate (86 mg, 0.47 mmol) in DMF (1 mL) was added dropwise with stirring to a suspension of NaH (60% in mineral oil, 19 mg, 0.47 mmol) in DMF (1 mL). The mixture was stirred under $N_2$ for 15 min. at 35° C. The Intermediate 34 (0.43 mmol) in DMF (1.00 mL) was added, and the mixture was stirred at 50° C. for 1.5 h. The reaction mixture was taken into EtOAc (30 mL), washed with 10% aq. $NH_4Cl$ (2×15 mL), brine, and dried ($Na_2SO_4$). Solvent was removed under vacuum and the crude product was purified by column chromatography (2% MeOH/DCM) to afford the product as a yellow solid.

Compound of Example 14. 4M HCl in ether (3 mL) was added dropwise to the solution of the Intermediate 38 (84 mg, 0.17 mmol) in DCM at 0° C., and the solution was stirred at 0° C. for 30 min, and then 1 h at r.t. Volatiles were removed under vacuum, and the residue taken into EtOAc (30 mL). The solution was washed with saturated $NaHCO_3$ solution (2×15 mL), brine, and dried ($Na_2SO_4$). Solvent was removed under vacuum and the crude product was purified by column chromatography ((5% methanol/DCM). White solid. $^1$H NMR (400 MHz, DMSO-$d_6$): 8.10 (s, 1H); 7.33 (t, J=8.5 Hz, 1H), 7.25 (d, J=8.0 Hz, 1H), 6.96 (t, J=8.1 Hz, 1H), 5.92 (s, 1H), 5.32 (d, J=7.6 Hz, 1H), 5.04 (m, 1H), 4.58 (br, 1H), 4.15 (t, J=8.8 Hz, 1H), 3.98 (t, J=7.2 Hz, 2H), 3.93 (t, J=7.6 Hz, 1H), 3.79 (dd, J=14.5, 2.9 Hz, 1H), 3.67 (dd, J=14.4, 6.4 Hz, 1H), 2.69 (t, J=7.3 Hz, 2H). MS (m/z): 391 [M+H].

Example 15

Compound of Structure

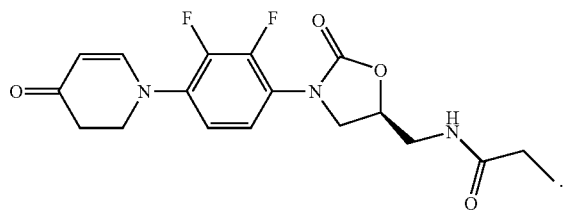

Scheme for Compound of Example 15

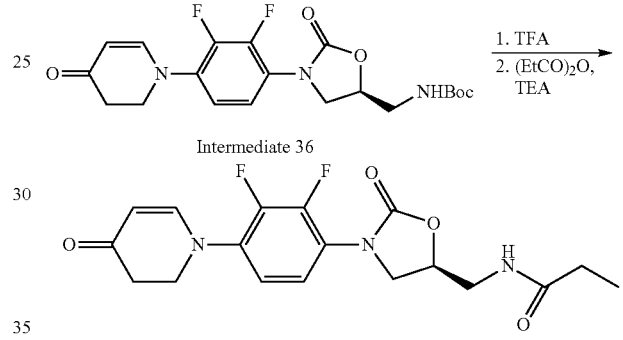

Compound of Example 15. TFA (0.2 mL) was added to the Intermediate 36 (37 mg, 0.093 mmol) in DCM (1 mL) at 0° C. After 30 min, the solvent was removed under vacuum, and the residue was dissolved in DCM (1 mL) with TEA (64 µL, 0.47 mmol). Propionic anhydride (24 µL, 0.19 mmol) was added at 0° C., and the mixture was stirred for 30 min. The mixture was extracted with DCM (2×10 mL), and the organic layers washed with water and dried ($Na_2SO_4$). Solvent was removed under vacuum, and the residue was purified by TLC (10% MeOH/DCM) to afford the product as a white solid. $^1$H NMR (400 MHz, DMSO-$d_6$): 8.22 (m, 1H), 7.60 (dd, J=7.2, 2.0 Hz, 1H), 7.39 (m, 1H), 7.26 (m, 1H), 5.08 (d, J=7.6 Hz, 1H), 4.81 (m, 1H), 4.09 (t, J=7.0 Hz, 1H), 3.95 (t, J=7.2 Hz, 2H), 3.74 (t, J=7.4 Hz, 1H), 3.45 (m, 2H), 2.53 (m, overlapped with DMSO-$d_6$, 2H), 2.12 (q, 4H), 0.99 (t, J=7.8 Hz, 3H). MS (m/z): 380 [M+H].

Example 16

Compound of Structure

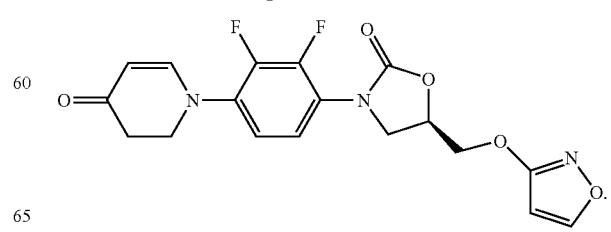

Scheme for Compound of Example 16

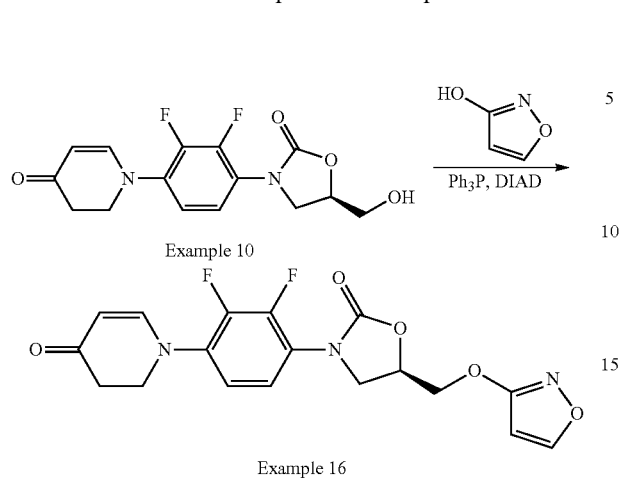

Example 16

Compound of Example 16. Diisopropyl azodicarboxylate DIAD (60 uL, 0.30 mmol) was added with stirring to PPh$_3$ (80 mg, 0.30 mmol) and dry THF (2 mL), and the mixture was stirred for 5 min. Isoxazol-3-ol (26 mg, 0.30 mmol) was added, after 5 min followed by the compound of Example 10 (97 mg, 0.27 mmol). The mixture was stirred for 1.5 h at r.t. Water (2 mL) was added, and the mixture was extracted with DCM (3×5 mL). Combined organic layers were washed with 0.1N HCl (3 mL), brine (3 mL) and dried (Na$_2$SO$_4$). Solvent was removed under vacuum, and the residue was purified by preparative TLC (2.4% methanol/DCM) to afford the product as a white solid. $^1$H NMR (400 MHz, DMSO-d$_6$): 8.20 (d, J=1.6 Hz, 1H), 7.42 (t, J=7.4 Hz, 1H), 7.25 (overlapped by CHCl$_3$, 1H), 6.99 (t, J=8.4 Hz, 1H), 6.05 (d, J=1.6 Hz, 1H), 5.33 (d, J=3.8 Hz, 1H), 5.09 (m, 1H), 4.63 (dd, J=11.2, 3.6 Hz, 1H), 4.55 (dd, J=11.6, 4.4 Hz, 1H), 4.25 (t, J=9.0 Hz, 1H), 4.03 (m, 3H), 2.70 (t, J=6.8 Hz, 2H). MS (m/z): 392 [M+H].

Example 17

Compound of Structure

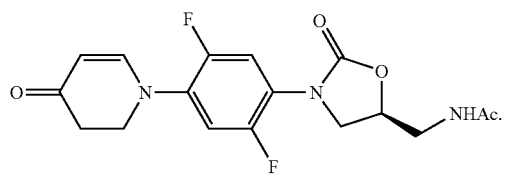

Scheme for Compound of Example 17

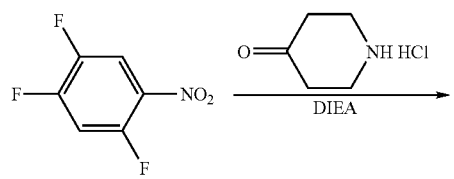

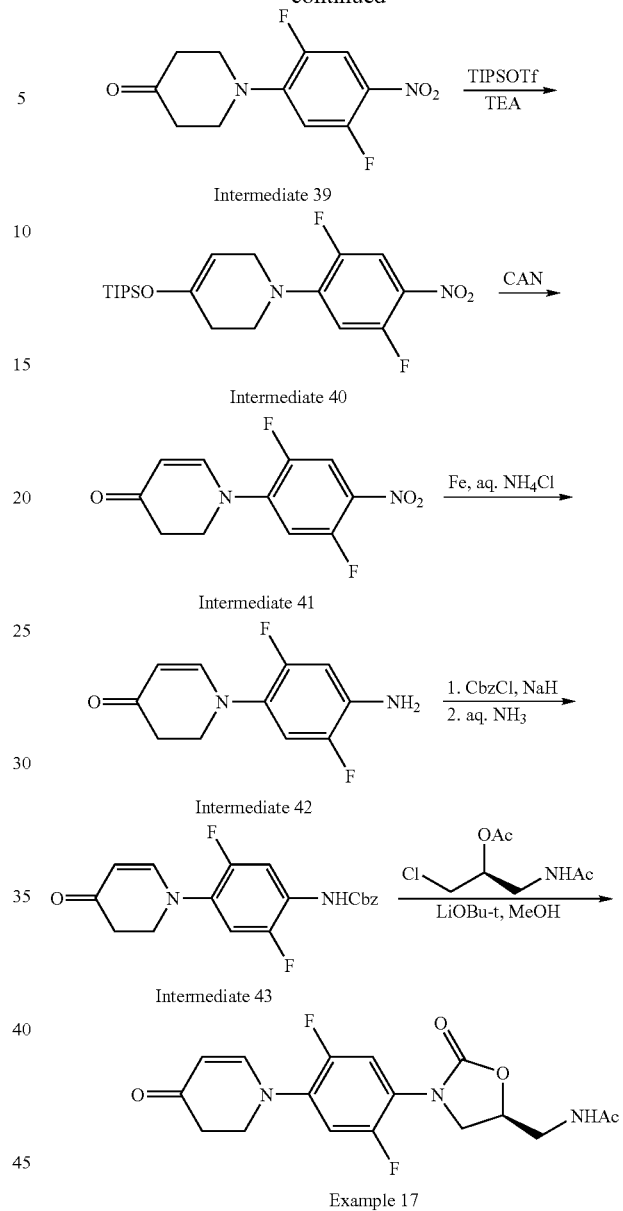

Intermediate 39. 2,4,5-Trifluoronitrobenzene (10 g, 61.2 mmol) was added dropwise with stirring to 4-piperidone hydrochloride (8.3 g, 61.2 mmol) and DIEA 18 g, 143.3 mmol) in NMP (120 mL) at ca. −5° C. under Ar. The mixture was allowed to warm up to r.t. and stirred o.n. The mixture was cooled in an ice bath and quenched with ice water (ca. 400 mL). The precipitate yellow product was filtered off, washed with water and dried under vacuum. The yellow solid obtained was used for the next step without further purification.

Intermediate 40. Triethylamine (2.3 g, 18.2 mmol) was added to the Intermediate 39 (3.5 g, 15.3 mmol) in THF (50 mL) at 0° C., followed by triisopropylsilyl triflate (5.6 g, 22.7 mmol). The mixture was allowed to warm up to r.t. over ca. 40 min, and stirred for another 2 h. Solvent was removed on a rotary evaporator. EtOAc (100 mL) was added, and the solution washed with 10% aq. NaHCO$_3$ (20 mL), brine (60 mL) and dried (Na$_2$SO$_4$). Solvent was removed under vacuum and to afford the product as dark oil. This was used at the next step without purification.

Intermediate 41. CAN (9.0 g, 16.4 mmol) was added portionwise with stirring to a solution of the Intermediate 40 (5.9 g, 13.2 mmol) in dry DMF (60 mL) at 0° C. The reaction mixture was allowed to warm up to r.t. and stirred for another 4 h. Most of solvent was removed under vacuum. Water was added and the mixture was extracted with EtOAc (2×100 mL). The combined organic layers were washed with brine and dried ($Na_2SO_4$). Solvent was removed and the residue purified by column chromatography (gradient 20% to 30% EtOAc in petroleum ether). The product was obtained as a yellow solid.

Intermediate 42. $NH_4Cl$ (4.8 g, 89.7 mmol) in water (20 mL) was added to a hot solution of the Intermediate 41 (2.1 g, 8.2 mmol) in EtOH (60 mL). Iron powder (5.2 g, 92.8 mmol) was added portionwise with stirring, and the mixture at ca. 100-105° C. for 40 min. The solution was filtered through Celite, and the precipitate washed with EtOH (5×10 mL). EtOH was removed under vacuum, and residue distributed between EtOAc (ca. 50 mL) and water (10 mL). Aq. layer was washed with EtOAc (2×60 mL), and combined organic layers were washed with water (3×7 mL), brine, and dried ($MgSO_4$). Solvent was removed under vacuum to afford the product as yellow crystals. Yield 1.5 g (81%).

Intermediate 43. 2M aq. LiOH (0.53 mL, 1.06 mmol) was chilled to ca. 5° C. and then added with stirring to the Intermediate 42 (138 mg, 0.53 mmol) in THF (3 mL) at 0° C., followed by benzyl chloroformate (0.093 mL, 0.64 mmol) in THF (0.25 mL). The mixture was stirred and allowed to warm up to r.t. over ca. 5 h. THF was removed under vacuum, and the mixture was extracted with EtOAc (3×20 mL). Combined organic layers were washed with 10% aq. citric acid (ca. 7×20 mL), water (3×15 mL), brine, and dried ($MgSO_4$). Solvent was removed under vacuum, and the crude was crystallized from ether and dried under vacuum. White solid.

Compound of Example 17. 1M LiOBu-t in THF (0.84 mL, 0.84 mmol) was added to Intermediate 43 (72 mg, 0.21 mmol) in DMF (0.12 mL) and MeOH (0.026 mL) at −10° C. under nitrogen, followed by N-[(2S)-2-acetoxy-3-chloropropyl]acetamide (122 mg, 0.63 mmol; prepared as described in Org. Proc. Res. Develop., 2003, p. 533). The mixture was allowed to warm up to r.t. over ca. 5 h and stirred o.n. The mixture was quenched with 10% aq. $NH_4Cl$ (1.5 mL) and extracted with EtOAc (3×15 mL). Combined organic layers were washed with brine and dried ($MgSO_4$). Solvent was removed under vacuum and the product isolated by column chromatography (5% MeOH in DCM). Off-white crystals. $^1$H NMR (300 MHz): 7.44 (m, 1H), 7.23 (dd, J=2.1 and 7.8 Hz, 1H), 6.96 (m, 1H), 5.96 (br. t, 1H), 5.31 (d, J=7.8 Hz, 1H); 4.84 (m, 1H), 4.11 (m, 1H), 3.96 (m, 2H), 3.83 (m, 1H), 3.80-3.62 (m, 2H), 2.71 (t, J=7.5 Hz, 2H), 2.07 (s, 3H). MS (m/z): 366 [M+H].

Example 18

Compound of Structure

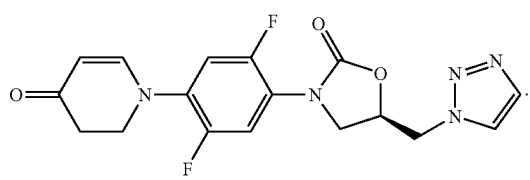

Scheme for Compound of Example 18

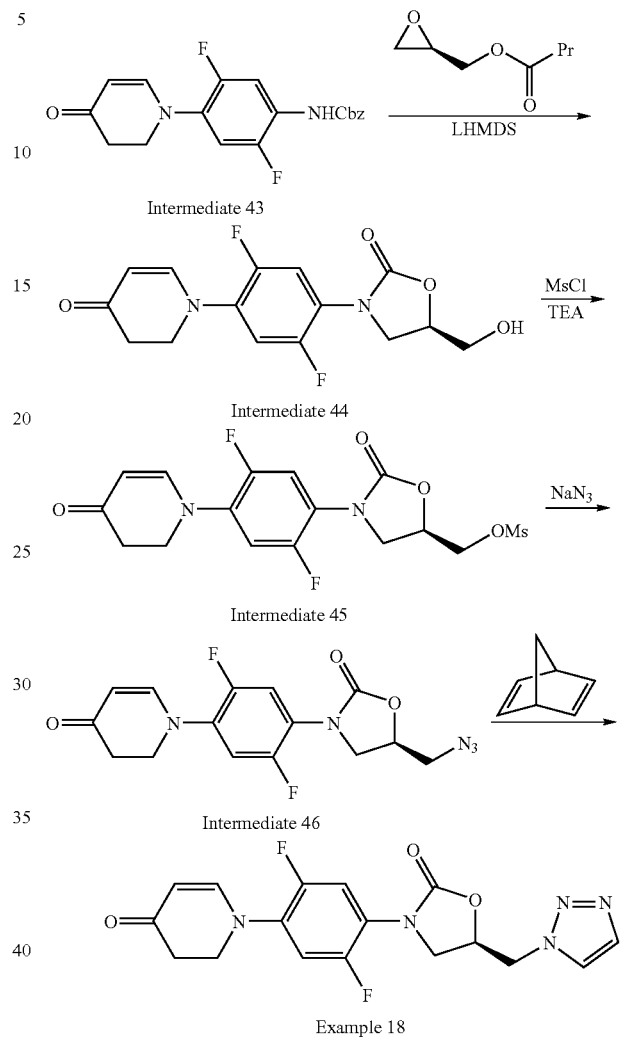

Intermediate 44. 1.06M LHMDS in THF (1.5 mL, 1.09 mmol) was added dropwise with stirring to a solution of the Intermediate 43 (0.6 g, 1.68 mmol) in THF (8.0 mL) at −78° C., and the mixture was stirred at this temperature for 30 min. (R)-Glycidyl butyrate (0.4 mL, 2.28 mmol) was added dropwise, and the mixture was allowed to warm up to r.t. and stirred o.n. The reaction was quenched with 10% aq. $NH_4Cl$ (15 mL), and THF was removed under vacuum. The residue was extracted with EtOAc (2×30 mL). Combined organic layers were washed with brine and dried ($Na_2SO_4$). Solvent was removed under vacuum. MeOH (5 mL) and 20% aqueous $Cs_2CO_3$ (5 mL) were added, and the mixture was stirred at r.t. for 20 min. The mixture was taken into EtOAc (50 mL), washed with water (2×15 mL), brine, and dried ($Na_2SO_4$). Solvent was removed under vacuum and the crude product was purified by column chromatography (2% methanol/DCM). The product isolated as a white solid.

Intermediate 45. MsCl (350 mg, 2.1 mmol) was added dropwise with stirring to the Intermediate 44 (280 mg, 0.91 mmol) and TEA (320 mg, 3.1 mmol) in DCM (5 mL) at ca. 0° C. The mixture was stirred for 20 min and allowed to warm up to r.t. The reaction mixture distributed between water and the DCM. Aq. layer was extracted with DCM (2×10 mL), and the combined organic layers washed with brine and dried (Na₂SO₄). Solvent was removed under vacuum to afford the product that was used for the next step without purification.

Intermediate 46. A mixture of the Intermediate 45 (350 mg, 0.91 mmol) and NaN₃ (296 mg, 4.56 mmol) in DMF (6 mL) was stirred at 55° C. o.n. After cooling to r.t., water (15 mL) was added, and the reaction mixture was extracted with DCM (3×30 mL). Combined organic layers were washed with brine (30 ml) and dried (Na₂SO₄). Solvent was removed under vacuum to afford the product as a light yellow solid. This was used directly for the next step without further purification.

Compound of Example 18. A mixture of the Intermediate 46 (220 mg, 0.6 mmol) and bicyclo[2.2.1]hepta-2,5-diene (600 mg, 6.2 mmol) in 1,4-dioxane (15 mL) under N₂ was heated at 100° C. for 10 h. Most of volatiles were removed under vacuum, and the product was purified by column chromatography (1% MeOH/DCM). White solid. $^1$H NMR (400 MHz): 7.83 (d, J=9.2 Hz, 2H), 7.13 (m, 2H), 6.89 (m, 1H), 5.31 (d, J=7.8 Hz, 1H), 5.13 (m, 1H), 4.83 (d, J=7.2 Hz, 2H), 4.27 (t, J=8.4 Hz, 1H), 3.95 (m, 1H), 3.94 (t, J=8.6 Hz, 2H), 2.68 (t, J=8.6 Hz, 2H). MS (m/z): 376 [M+H].

Example 19

Compound of Structure

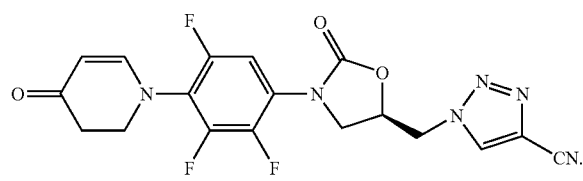

Scheme for Compound of Example 19

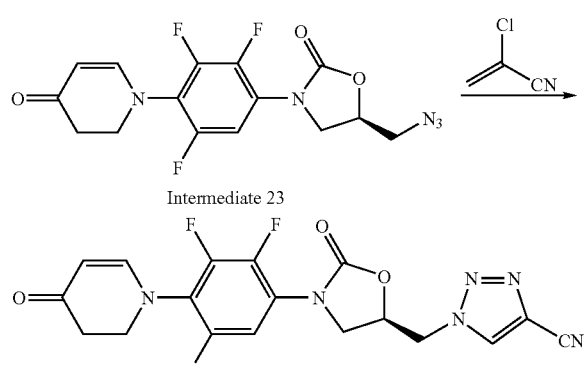

Example 19

Compound of Example 19. 2-Chloroacrylonitrile (44 uL, 0.54 mmol) was added to the Intermediate 23 (100 mg, 0.27 mmol) in DMF (1 mL) under Ar. The reaction mixture was stirred at 95° C. for 2 d. After cooling to r.t., the mixture was taken into water (5 mL), extracted with EtOAc (3×5 mL), and dried (Na₂SO₄). The product was purified by preparative TLC (5% methanol/DCM). Light yellow solid. $^1$H NMR (400 MHz): 8.28 (s, 1H), 7.20 (m, 1H), 7.09 (d, J=7.6 Hz, 1H), 5.32 (d, J=7.6 Hz, 1H), 5.18 (m, 1H), 4.94 (dd, J=14.4, 3.2 Hz, 1H), 4.86 (dd, J=15.2, 5.2 Hz, 1H), 4.35 (t, J=8.8 Hz, 1H), 4.06 (dd, J=9.2, 6.4 Hz, 1H), 3.92 (t, J=7.4 Hz, 2H), 2.70 (t, J=7.2 Hz, 2H). MS (m/z): 419 [M+H].

Example 20

Compound of Structure

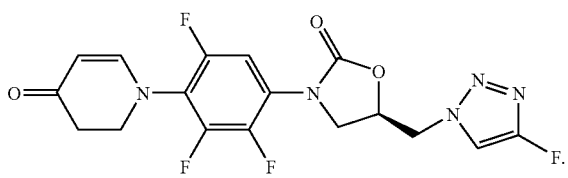

Scheme for Compound of Example 20

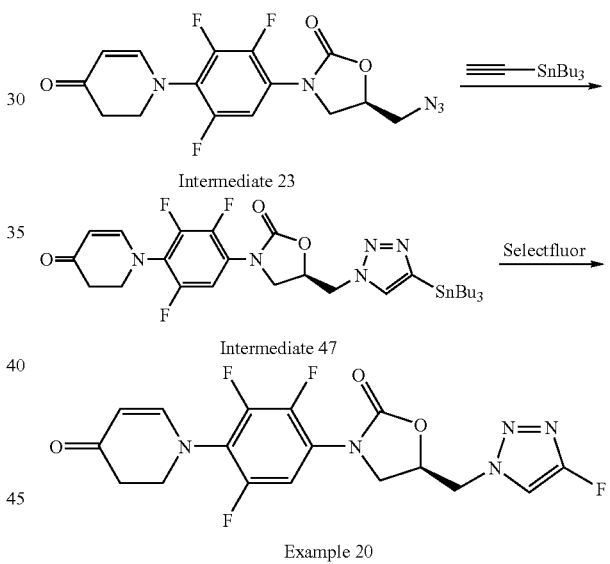

Intermediate 47. Tributylethynylstannane (260 μL, 0.90 mmol) was added to the Intermediate 23 in toluene (6 mL), and the mixture was stirred at 70° C. for 2 d. Solvent was removed under vacuum, and the residue was purified by column chromatography (2.4% methanol/DCM) to afford the product. MS (m/z): 684 [M+H].

Compound of Example 20. 1-Chloromethyl-4-fluoro-1,4-diazoniobicyclo[2.2.2]octane bis(tetrafluoroborate) (Selectfluor™; 278 mg, 0.78 mmol) was added to the Intermediate 47 (447 mg, 0.65 mmol) in MeCN (6 mL). The reaction mixture was stirred for 3 d at r.t., quenched with brine, and extracted with DCM (2×10 mL). Combined organic layers were dried (Na₂SO₄), and concentrated under vacuum. The residue was purified by preparative TLC (2.4% methanol/DCM) to afford the product as a pale yellow solid. $^1$H NMR (400 MHz): 8.19 (s, 1H), 7.97 (d, J=10.0 Hz, 1H), 7.80 (s, 1H), 7.43 (ddd, J=12.0, 6.8, 2.4 Hz, 1H), 5.22 (m, 1H), 4.87

(d, J=4.8 Hz, 2H), 4.27 (t, J=8.8 Hz, 1H), 3.92 (dd, J=8.8, 5.6 Hz, 1H), 3.85 (t, J=7.2 Hz, 2H), 2.61 (td, J=8.0, 2.8 Hz, 2H). MS (m/z): 412 [M+H].

Example 21

Compound of Structure

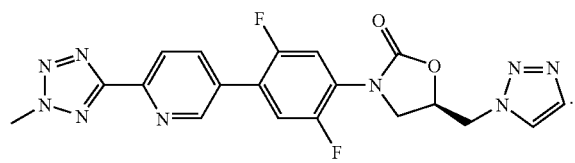

Scheme for Compound of Example 21

(9.0 mmol) was added dropwise, and the mixture was stirred for 16 h at r.t. Water (5 mL) was added, and THF removed under vacuum. Methanol (25 mL) and conc. aq. ammonia (ca. 5 mL) were added, and the solution was stirred for 1 h at r.t. The solution was concentrated under vacuum and extracted with EtOAc (3×20 mL). Combined organic layers were dried ($Na_2SO_4$), solvent was removed under vacuum, and the product was purified by column chromatography (5% ethyl acetate/petroleum ether). White solid.

Intermediate 49. (S)-tert-butyl 3-chloro-2-hydroxypropyl-carbamate (122 mg, 0.58 mmol; prepared as described in Org. Proc. Res. Develop., 2003, p. 533) was added to the Intermediate 48 (100 mg, 0.29 mmol) in MeCN (0.5 mL) at 0° C., followed by t-BuOLi (2.2 M in THF, 0.33 mL, 0.73 mmol). The reaction mixture was stirred at 0° C. for 3 h and then o.n. at r.t. Water (5 mL) was added and the mixture was extracted with ethyl acetate (3×15 mL). Combined organic layers were dried ($Na_2SO_4$), solvent was removed under vacuum, and the product was purified by preparative TLC (5% methanol/DCM). The product was obtained as light yellow oil.

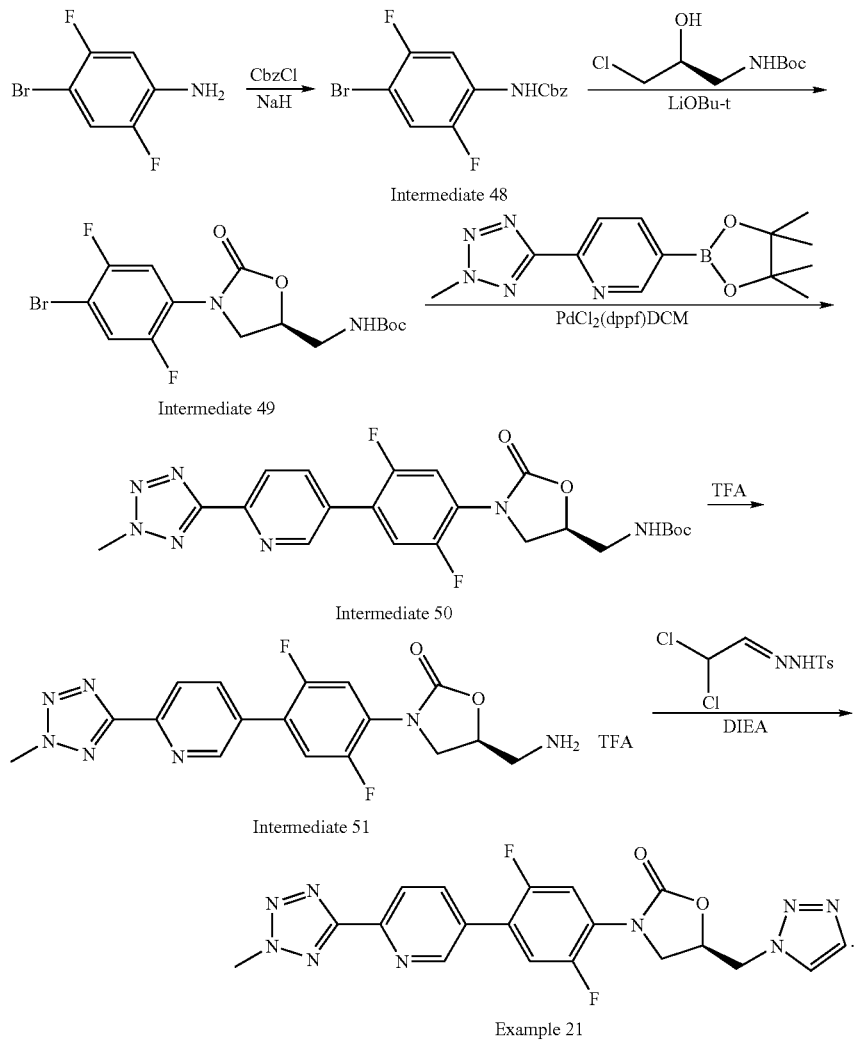

Intermediate 48. To a solution of 4-bromo-2,5-difluoroaniline (1.7 g, 8.2 mmol) in dry THF (25 mL) was added NaH (60% dispersion in mineral oil, 1.0 g, 25.1 mmol) in portions, and the mixture was cooled to 0° C. Benzyl chloroformate Intermediate 50. 2-(2-Methyl-2H-tetrazol-5-yl)-5-(4,4,5,5-tetramethyl-1,3,2-dioxaborolan-2-yl)pyridine (230 mg, 0.8 mmol) and Intermediate 49 (320 mg, 0.78 mmol) were dissolved in DMF (15 mL) under Ar. KOAc (230 mg, 2.4 mmol)

and PdCl$_2$(dppf)DCM (58 mg, 0.078 mmol) were added, the mixture was degassed, and then stirred at 80° C. o.n. Resulted solution was filtered through Celite and washed with 50 mL of EtOAc. The filtrate was concentrated, washed with 10% NH$_4$Cl, brine, and dried (Na$_2$SO$_4$). Solvent was removed under vacuum, and the product was purified by preparative TLC (5% methanol/DCM). White solid.

Intermediate 51. TFA (0.75 mL) was added with stirring to the Intermediate 50 (23 mg, 0.047 mmol) in DCE (2.5 mL) at 0° C. The reaction mixture was stirred for 2 h at r.t. and concentrated under vacuum to afford the product that was used directly at the next step.

Compound of Example 21. N'-(2,2-Dichloroethylidene)-4-methylbenzenesulfonohydrazide (42 mg, 0.11 mmol; prepared as described in Heterocycles, 1998, p. 895) was added with stirring to the Intermediate 51 (50 mg, 0.10 mmol) and DIEA (55 mg, 0.17 mmol) in MeOH (4 mL) at 0° C. The reaction mixture was stirred at 0° C. for 3 h, and then concentrated under vacuum. Water (ca. 5 mL) was added, and the mixture was extracted with dichloroethane (3×15 ml). Combined organic layers were dried (Na$_2$SO$_4$), concentrated under vacuum, and the residue was purified by preparative TLC (5% DCM/methanol). The product was obtained as a white solid. $^1$H NMR (400 MHz): 8.89 (s, 1H), 8.48 (d, J=7.6 Hz, 1H), 8.06 (d, J=7.8 Hz, 1H), 7.85 (d, J=7.6 Hz, 2H), 7.29 (m, 2H), 5.18 (m, 1H), 4.86 (d, J=7.6 Hz, 2H), 4.58 (s, 3H), 4.38 (t, J=8.8 Hz, 1H), 4.09-4.12 (m, 1H). MS (m/z): 440 [M+H].

Example 22

Compound of Structure

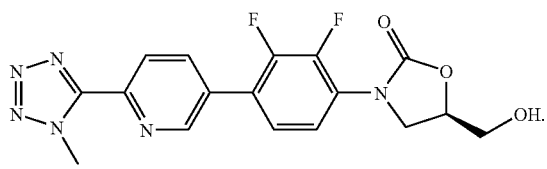

Scheme for Compound of Example 22

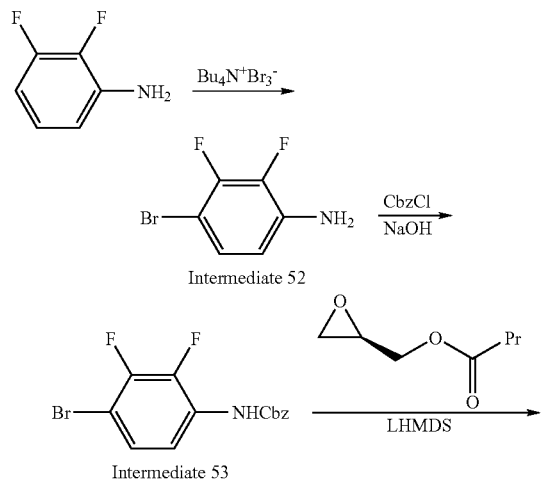

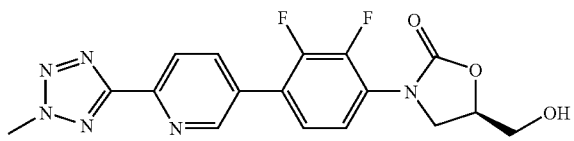

Intermediate 52. Bu$_4$NBr$_3$ (2.9 g, 6.0 mmol) in DCM (10 mL) was added dropwise with stirring to 2,3-difluoroaniline (645 mg, 5.0 mmol) in DCM (10 mL). The reaction was stirred at r.t. until the starting materials disappeared. Solvent was then removed under vacuum, water added, and the mixture was extracted with EtOAc (2×60 mL). Combined organic layers were washed with brine, dried (Na$_2$SO$_4$), and concentrated under vacuum to afford the product was obtained as a colorless oil. MS (m/z): 209 [M+H].

Intermediate 53. Benzyl chloroformate (1.1 mL, 7.5 mmol) was added dropwise with stirring to the Intermediate 52 (1.0 g, 4.8 mmol) in 10% aq. NaOH (15 mL)) and THF (30 mL) at ca. 0° C. The reaction mixture was stirred at r.t. for ca. 6 h. The reaction was quenched with 10% NH$_4$Cl solution and extracted with DCM (2×50 mL). Combined organic layers were washed with brine, dried (Na$_2$SO$_4$), and concentrated under vacuum. The residue was purified by preparative TLC (10% ethyl acetate/petroleum ether) to give the product as a white solid. $^1$H NMR (400 MHz, CDCl$_3$): 7.88 (m, 1H); 7.40 (m, 5H); 6.90 (m, 1H); 5.25 (s, 2H).

Intermediate 54. 1.06M Lithium hexamethyldisilylamide in THF (LHMDS; 1.2 mL, 1.3 mmol) was added dropwise with stirring to a solution of the Intermediate 53 (350 mg, 1.0 mmol) in THF (8.0 mL) at −78° C., and the mixture was stirred at this temperature for 30 min. (R)-Glycidyl butyrate (290 mg, 2.0 mmol) was added dropwise, and the mixture was allowed to warm up to r.t. and stirred o.n. The reaction was quenched with 10% aq. NH$_4$Cl (15 mL), and THF was removed under vacuum. The residue was extracted with EtOAc (2×20 mL). Combined organic layers were washed with brine and dried (Na$_2$SO$_4$). Solvent was removed under vacuum and the crude product was purified by preparative TLC (10-20% methanol/DCM) to give the product as a white solid. $^1$H NMR (400 MHz): 7.30 (m, 2H), 4.81 (m, 1H), 4.11 (t, J=8.8 Hz, 1H), 4.01 (m, 2H), 3.78 (m, 1H).

Compound of Example 22. 5-Bromo-2-(1-methyl-1H-tetrazol-5-yl)pyridine (2.44 g, 10 mmol) was dissolved in 30 mL of anhydrous DMSO. To this solution was added bis-(pinocalato)diboron (5.08 g, 20 mmol), followed by KOAc (4.00 g, 40 mmol) and PdCl$_2$(dppf)DCM (0.75 g, 1 mmol). The reaction mixture was degassed, and then stirred at 80° C. o.n. Resulted solution was filtered through Celite, and the precipitate was washed with EtOAc (100 mL). The filtrate was concentrated and washed with 10% NH$_4$Cl, brine, and dried (Na$_2$SO$_4$). Solvent was removed under vacuum, and the residue was dissolved in ether and filtered through a short silica gel pad. The filtrate was concentrated and the formed solid was washed with methanol. Thus isolated [2-(1-methyl-1H-tetrazol-5-yl)pyridyl-5-yl)(pinacolato)boron was obtained as a white solid [$^1$H NMR (400 MHz): 9.10 (s, 1H); 8.25 (s, 2H); 4.48 (s, 3H); 1.48 (s, 12H)]. This compound (68 mg, 0.24 mmol) wad added to the Intermediate 54 (50 mg, 0.16 mmol)

in dioxane (5 mL) and water (1 mL), followed by PdCl$_2$(dppf) DCM (18 mg, 0.024 mmol) and K$_2$CO$_3$ (88 mg, 0.64 mmol). The reaction mixture was degassed, and then stirred at 80° C. o.n. The reaction mixture was filtered through Celite, and the precipitate was washed with EtOAc (50 mL). The filtrate was concentrated and washed with 10% NH$_4$Cl, brine, and dried (Na$_2$SO$_4$). Solvent was removed under vacuum, and the residue was purified by preparative TLC (5% methanol/DCM), to afford the product was obtained as a white solid. $^1$H NMR (400 MHz): 8.96 (m, 1H), 8.36 (d, J=8.0 Hz 1H), 8.05 (d, J=8.0 Hz, 1H), 7.54-7.60 (m, 1H), 7.32 (m, 1H), 4.88 (m, 1H), 4.51 (s, 3H), 4.18 (dd, J=8.0 Hz, 1H), 4.05 (m, 2H), 3.82 (dd, J=3.6, 9.2 Hz, 1H). MS (m/z): 389 [M+H].

Example 23

Compound of Structure

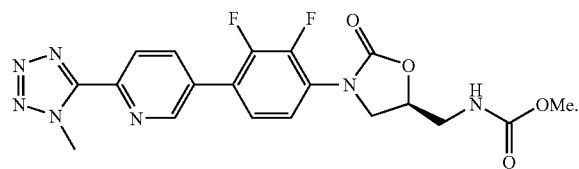

Scheme for Compound of Example 23

Intermediate 55. (S)-tert-butyl 3-chloro-2-hydroxypropyl-carbamate (120 mg, 0.57 mmol; prepared as described in Org. Proc. Res. Develop., 2003, p. 533) was added to the Intermediate 53 (150 mg, 0.44 mmol) in DMF (0.5 mL) at ca. −10° C., followed by t-BuOLi (2.2 M, 480 µL, 1.06 mmol). The reaction mixture was stirred at 0° C. for 3 h and then o.n. at r.t. Saturated aq. NH$_4$Cl (ca. 5 mL) was added, and the mixture was extracted with EtOAc (3×15 mL). Combined organic layers were dried (Na$_2$SO$_4$), solvent was removed under vacuum, and the product was purified by preparative TLC (5% methanol/DCM). The desired product was obtained as a colorless solid. MS (m/z): 429 [M+Na].

Intermediate 56. The compound was prepared by the coupling procedure described for Compound of Example 22, except that [2-(1-methyl-1H-tetrazol-5-yl)pyridyl-5-yl)(pinacolato)boron (40 mg, 0.14 mmol) was reacted with above Intermediate 55 (57 mg, 0.14 mmol) instead of the Intermediate 54. White solid. MS (m/z): 488 [M+H].

Compound of Example 23. TFA (0.4 mL) was added to the Intermediate 56 (25 mg, 0.051 mmol) in DCE (2 mL) at 0° C., and the mixture was stirred for 1 h at 0° C. Solvent removed under vacuum, and the residue taken into MeCN (2 mL) with TEA (36 µL). Pentafluorophenyl methyl carbonate (19 mg) was added, and the mixture was stirred for 30 min at r.t. Solvent was removed under vacuum, and the residue was purified by preparative TLC (5% methanol/DCM) to afford the product as a white solid (18 mg, 78%). $^1$H NMR (400 MHz): 8.99 (s, 1H), 8.28 (s, 2H), 7.59 (m, 3H), 4.81 (m, 1H),

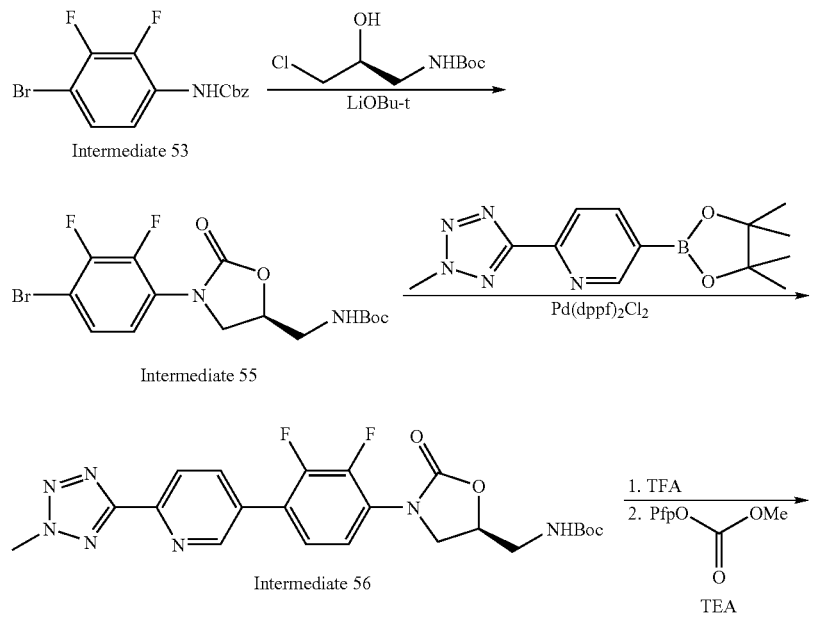

Example 23

4.50 (s, 3H), 4.20 (t, J=8.8 Hz, 1H), 3.89 (t, J=6.8 Hz, 1H), 3.57 (s, 3H), 3.41 (t, J=5.6 Hz, 2H). MS (m/z): 446.0 [M+H].

Example 24

Compound of Structure

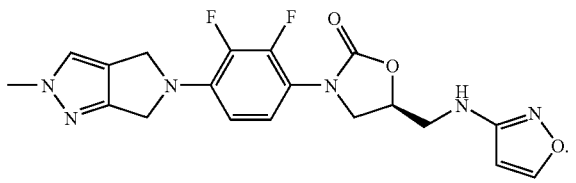

Scheme for Compound of Example 24

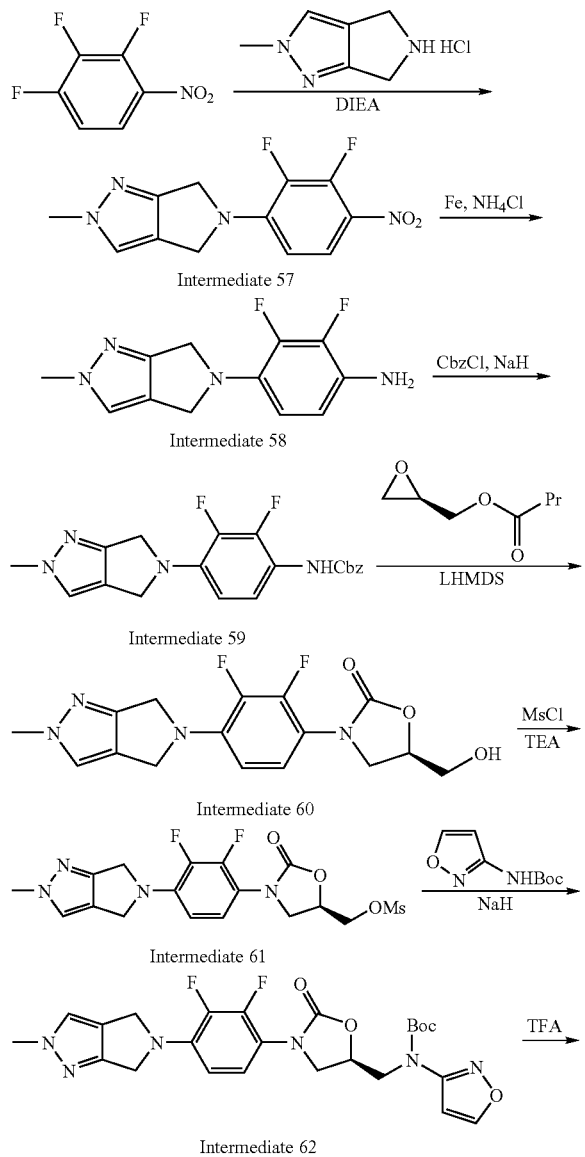

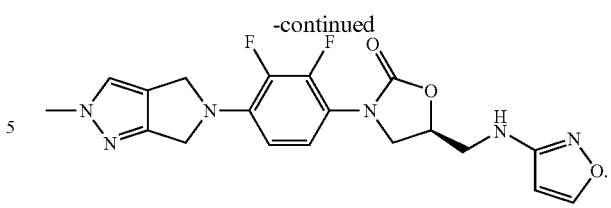

Example 24

Intermediate 57. DIEA (3.8 mL) was added dropwise with stirring to 2-methyl-2,4,5,6-tetrahydropyrrolo[3,4-c]pyrazole hydrochloride (1.0 g, 7.04 mmol; prepared as described in JP 6073056) and 2,3,4-trifluoronitrobenzene (1.5 g, 8.45 mmol) in MeCN (100 mL) at −10° C. The mixture was allowed to warm up to r.t. and stirred for 6 h. Solvent was removed under vacuum, and the residue was taken into EtOAc (60 mL), washed with water (40 mL×3), brine (40 mL), and dried ($Na_2SO_4$). Solvent was removed under vacuum, and the product was purified by column chromatography (gradient 17% to 75% petroleum ether/ethyl acetate). Yellow solid. $^1$H NMR (400 MHz): 7.54 (m, 1H), 7.27 (d, J=6.4 Hz, 1H), 6.95 (m, 1H), 4.54 (s, 2H), 4.49 (s, 2H), 3.85 (s, 3H).

Intermediate 58. $NH_4Cl$ (1.14 g, 21.3 mmol) in water (3 mL) was added to a hot solution of the Intermediate 57 (0.60 g, 2.1 mmol) in EtOH (6 mL). Iron powder (5.2 g, 92.8 mmol) was added portionwise with stirring, and the mixture at 95° C. for 1 h. The solution was filtered through Celite, and the precipitate washed with EtOH. EtOH was removed under vacuum, and residue distributed between EtOAc (20 mL) and water (10 mL). Aq. layer was washed with EtOAc, and combined organic layers were washed with water (3×7 mL), brine, and dried ($MgSO_4$). Solvent was removed under vacuum to afford the product as yellow crystals. $^1$H NMR (400 MHz): 7.27 (d, J=2.8 Hz, 1H), 6.90 (m, 1H), 6.45 (m, 1H), 4.35 (d, J=2.0 Hz, 2H), 4.28 (s, 2H), 3.85 (s, 3H), 1.64 (s, 2H). MS (m/z): 251 [M+H].

Intermediate 59. 60% NaH in mineral oil (224.6 mg, 5.62 mmol) was added portionwise with stirring to the Intermediate 58 (391.6 mg, 1.56 mmol) in THF (6 mL) at −10° C., followed by a solution of benzyl chloroformate (0.4 mL, 2.82 mmol) in THF (2 mL). The mixture was allowed to warm up to r.t. and stirred o.n. The reaction was quenched with saturated $NH_4Cl$ (5 mL) and extracted with EtOAc (3×20 mL). Combined organic layers were washed with brine (15 mL), and dried ($Na_2SO_4$). Solvent was removed under vacuum, and the residue was purified by column chromatography (80% to 75% petroleum ether/ethyl acetate) to afford the product as a white solid. $^1$H NMR (400 MHz): 8.12 (s, 1H), 7.99 (s, 1H), 6.10 (t, J=15.6 Hz, 6H), 7.09 (m, 1H), 5.21 (s, 1H), 5.13 (s, 1H), 4.31 (s, 2H), 4.24 (s, 2H). MS (m/z): 385 [M+H].

Intermediate 60. 1.06M LHMDS in THF (0.19 ml, 0.20 mmol) was added dropwise with stirring to a solution of the Intermediate 59 (65.0 mg, 0.17 mmol) in THF (2.0 mL) at −78° C., and the mixture was stirred at this temperature for 1 h. (R)-Glycidyl butyrate (48.7 mg, 0.34 mmol) was added dropwise, and the mixture was allowed to warm up to r.t. and stirred o.n. The reaction was quenched with saturated aq. $NH_4Cl$ (10 mL), and extracted with EtOAc (3×15 mL). Combined organic layers were washed with brine and dried ($Na_2SO_4$). Solvent was removed under vacuum and the crude product was purified by preparative TLC (5% DCM/MeOH) gave the desired product as a white solid. $^1$H NMR (400 MHz): 7.25 (d, J=14.4 Hz, 1H), 7.15 (t, J=14.4 Hz, 1H), 7.04 (m, 1H), 4.77 (t, J=14.4 Hz, 1H), 4.47 (s, 1H), 4.40 (s, 1H), 3.99 (t, J=16.8 Hz, 2H) 3.90 (t, J=14.8 Hz, 1H), 3.81 (s, 3H), 3.71 (t, J=6.1 Hz, 2H). MS (m/z): 351 [M+H].

Intermediate 61. MsCl (20 μL, 0.27 mmol) was added dropwise with stirring to the Intermediate 60 (78.9 mg, 0.22 mmol) and TEA (94 μL, 0.67 mmol) in DCM (2 mL) at ca. 0° C. The mixture was stirred for 30 min and allowed to warm up to r.t. The reaction mixture distributed between water (5 mL) and DCM (10 mL). Aq. layer was extracted with DCM (2×10 mL), and the combined organic layers washed with brine and dried (Na$_2$SO$_4$). Solvent was removed under vacuum to afford the product as a white solid.

Intermediate 62. A solution of tert-butyl isoxazol-3-ylcarbamate (45.0 mg, 0.24 mmol) in DMF (1 mL) was added dropwise with stirring to a suspension of NaH (60% in mineral oil, 9.8 mg, 0.24 mmol) in DMF (2 mL). The mixture was stirred under Ar for 15 min. at 35° C., and then cooled down to r.t. The Intermediate 61 (95.1 mg, 0.22 mmol) in DMF (1 mL) was added, and the mixture was stirred at 50° C. for 1.5 h. The reaction mixture was taken into EtOAc (30 mL), washed with 10% aq. NH$_4$Cl (2×15 mL), brine, and dried (Na$_2$SO$_4$). Solvent was removed under vacuum and the crude product was purified by preparative TLC (2.4% MeOH/DCM) to afford the product as a white solid. MS (m/z): 517 [M+H].

Compound of Example 24. TFA (0.2 mL) was added dropwise to the solution of the Intermediate 62 (25 mg, 0.048 mmol) in DCE (1 mL) at 0° C., and the solution was stirred at 0° C. for 1 h. The reaction was quenched with 5% aq. NaHCO$_3$ (5 mL) and extracted with DCM (3×3 mL), brine, and dried (Na$_2$SO$_4$). Solvent was removed under vacuum and the crude product was purified by preparative TLC (5% MeOH/DCM) to afford the product as a white solid. $^1$H NMR (400 MHz): 8.03 (s, 1H), 7.27 (s, 1H), 7.09 (m, 1H), 5.75 (s, 1H), 4.97 (t, J=6.4 Hz, 1H), 4.39 (d, J=12.8 Hz, 2H), 4.32 (s, 2H), 4.03 (t, J=17.6 Hz, 1H), 3.85 (s, 3H), 3.82 (d, J=8.8 Hz, 1H), 3.70 (d, J=14.4 Hz, 1H), 3.56 (m, 1H). MS (m/z): 417 [M+H].

Example 25

Compound of Structure

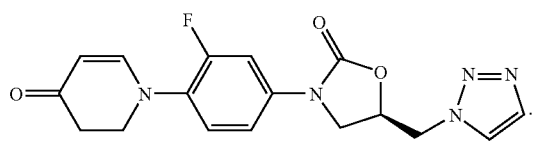

Compound of Example 25. Compound of Example 25 was prepared following the procedure described in International Patent Publication No. WO 2004/033449. $^1$H NMR (300 MHz): 7.78 (dd, J=1.2 and 9.5 Hz, 1H); 7.44 (dd, J=2.1 and 13.5 Hz, 1H), 7.20-7.06 (m, 4H), 5.25 (d, J=7.5 Hz, 1H), 5.14 (m, 1H), 4.83 (d, J=4.2 Hz, 2H), 4.18 (m, 1H), 4.03-3.90 (m, 3H), 2.67 (m, 2H). MS (m/z): 358 [M+H].

Example 26

Compound of Structure

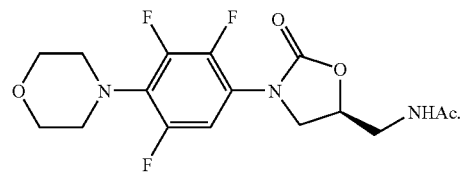

Compound of Example 26. Compound of Example 26 was prepared following the procedure described in International Patent Publication No. WO 2005/113520, except that benzyl chloroformate was substituted for isobutyl chloroformate. $^1$H NMR (300 MHz): 7.06 (m, 1H); 5.99 (br. t, 1H), 4.83 (m, 1H); 4.07 (m, 1H); 3.80-3.77 (m, 5H), 3.68 (m, 2H); 3.24 (m, 4H), 2.07 (s, 3H). MS (m/z): 375 [M+H].

Utility and Testing

Compounds of the subject invention exhibit potent activities against a variety of microorganisms, including gram positive microorganisms. Accordingly, compounds of the subject invention have useful antibacterial activity. Thus, compounds of the present invention are useful antimicrobial agents and may be effective against a number of human and veterinary pathogens, including gram positive aerobic bacteria such as multiply-resistant staphylococci, enterococci, and streptococci, as well as anaerobic microorganisms such as bacteroides and clostridia species, and acid-fast microorganisms such as *Mycobacterium tuberculosis* and *Mycobacterium avium*.

Compounds of this invention can have useful activity against a variety of pathogenic microorganisms. The in vitro activity of compounds of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa., USA. Minimum inhibitory concentration (MIC) refers to the lowest concentration of drug (μg/mL) that inhibits visible growth of the organism. Lower MIC values indicate a higher antibacterial activity. Typically, compounds of present invention have useful potency against Gram-positive or Gram-negative pathogens with MIC values of ≦16 μg/mL. The useful activity of compounds of the present invention against a clinical isolate of methicillin-resistant *Staphylococcus aureus* (MRSA; from the Massachusetts General Hospital, USA) is illustrated by the MIC data of Table 1.

TABLE 1

Antibacterial Activity (MIC) Against MRSA

| EXAMPLES | MRSA, MIC, μg/mL |
| --- | --- |
| Linezolid | 2.0 |
| Example 1 | 4.0 |
| Example 2 | 2.0 |
| Example 3 | 1.0 |

TABLE 1-continued

Antibacterial Activity (MIC) Against MRSA

| EXAMPLES | MRSA, MIC, µg/mL |
| --- | --- |
| Example 4 | 2.0 |
| Example 5 | 1.0 |
| Example 6 | 4.0 |
| Example 7 | 2.0 |
| Example 8 | 4.0 |
| Example 9 | 1.0 |
| Example 10 | 2.0 |
| Example 11 | 1.0 |
| Example 12 | 4.0 |
| Example 13 | 1.0 |
| Example 14 | 0.25 |
| Example 15 | 2.0 |
| Example 16 | 4.0 |
| Example 17 | 4.0 |
| Example 18 | 4.0 |
| Example 19 | 4.0 |
| Example 20 | 4.0 |
| Example 21 | 2.0 |
| Example 22 | 1.0 |
| Example 23 | 1.0 |
| Example 26 | 2.0 |

Monoamine oxidase inhibitory and myelosuppression (i.e. bone marrow or hematopoietic toxicity) for compounds invented herein can be assessed using established protocols as described below.

Human monoamine oxidase (MOA) A type enzyme inhibition activity for select compounds was measured using a commercial MAO assay kit MAO-Glo™ from Promega Co. (USA). The assay was performed as described in the company's technical bulletin "MAO-Glo™ Assay". The protocol involves an incubation of the MAO A enzyme (BD Gentest™) with a luminogenic MAO substrate to produce an enzymatic product which is converted to luciferin by a coupled reaction. The released luciferin undergoes further transformation to generate light that is detected and measured. The amount of the light is directly proportional to the activity of MAO. Percent inhibition at several concentrations is established relative to the uninhibited control rate, and the $IC_{50}$ (µg/mL) values are calculated. A low $IC_{50}$ value indicates that the tested inhibitor possesses a strong affinity or binding to MAO enzyme, thus being a stronger inhibitor, as compared to the compound with a higher $IC_{50}$ value. The MAO inhibition data for select compound of this invention are illustrated in the Table 2 below.

Myelosuppressive potential (hematopoietic or bone marrow toxicity) was evaluated using human $CD34^+$ bone marrow cells, generally following methods described by Leach in International Patent Publication No. WO 2006/097828. Thus, an oxazolidinone compound was incubated with fresh human bone marrow cells for 9-10 days at 37° C. in 5% $CO_2$ atmosphere. At end of the incubation period, the bone marrow toxicity was accessed by measuring inhibition ($IC_{50}$, µg/mL) of $CD34^+$ cell growth using a luminescence assay. Lower $IC_{50}$ value indicates a higher myelosuppression potential with enhanced probability of undesired adverse effects in vivo, while a higher $IC_{50}$ value indicates reduced bone marrow toxicity. The $CD34^+$ inhibition data for representative compounds of this invention are illustrated in the Table 2 below.

As evident from the data of the Table 2, certain compounds of the present invention offer a significantly reduced MAO inhibition over the current antibacterial therapy standard of this class linezolid (Zyvox®).

TABLE 2

Monoamine Oxidase and Bone Marrow $CD34^+$ Cells Inhibition

| EXAMPLES | MAO A[a] $IC_{50}$, µg/mL | $CD34^a$ $IC_{50}$, µg/mL |
| --- | --- | --- |
| Linezolid (Lin.) | Range 3.8-4.1 | Range 7.9-14.0 |
| Example 2 | 56.9 (Lin. 4.1) | 13.2 (Lin. 7.9) |
| Example 4 | 21.7 (Lin. 3.8) | 17.7 (Lin. 8.1) |
| Example 5 | 12.3 (Lin. 4.1) | 15.7 (Lin. 7.9) |
| Example 13 | 17.1 (Lin. 4.1) | 6.3 (Lin. 7.9) |
| Example 25 | 1.8 (Lin. 3.8) | 2.6 (Lin. 14.0) |

[a]Linezolid value in a side-by-side test in parenthesis

It is also evident from the Table 2, that certain compounds of the present invention display a beneficially reduced myelosuppressive potential, as demonstrated by the data for bone marrow $CD34^+$ cell growth suppression assay.

Thus, the biological testing data of Tables 1 and 2 demonstrate that certain compounds of this invention offer an excellent antibacterial activity beneficially coupled with a reduced propensity for monoamine oxidase inhibition and myelosuppression.

Administration and Pharmaceutical Formulations

In general, the compounds of the subject invention can be administered in a therapeutically effective amount by any of the accepted modes of administration for agents that serve similar utilities. By way of example, compounds of the subject invention may be administered orally, parenterally, transdermally, topically, rectally, or intranasally. The actual amount of a compound of the subject invention, i.e., the active ingredient, will depend on a number of factors, such as the severity of the disease, i.e., the infection, to be treated, the age and relative health of the subject, the potency of the compound used, the route and form of administration, and other factors, all of which are within the purview of the attending clinician.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

When employed as pharmaceuticals, the compounds of the subject invention are usually administered in the form of pharmaceutical compositions. These compounds can be administered by a variety of routes including oral, parenteral, transdermal, topical, rectal, and intranasal.

Compounds provided herein are effective as injectable, oral, inhaleable, or topical compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 0.1 to about 2000 mg, more usually about 1 to about 900 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

An active compound is effective over a wide dosage range and is generally administered in a pharmaceutically or therapeutically effective amount. It, will be understood, however, that the amount of the compound actually administered can be determined by a physician, in the light of the relevant circumstances, including the condition to be treated, the severity of the bacterial infection being treated, the chosen route of administration, the actual compound administered, the age, weight, and response of the individual patient, the severity of the patient's symptoms, and the like.

In therapeutic use for treating, or combating, bacterial infections in warm-blooded animals, compounds or pharmaceutical compositions thereof can be administered orally, topically, transdermally, and/or parenterally at a dosage to obtain and maintain a concentration, that is, an amount, or blood-level of active component in the animal undergoing treatment which will be antibacterially effective. Generally, such antibacterially or therapeutically effective amount of dosage of active component (i.e., an effective dosage) will be in the range of about 0.1 mg/kg to about 250 mg/kg, more preferably about 1.0 mg/kg to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure-breathing machine. Solution, suspension, or powder compositions may be administered, preferably orally or nasally, from devices that deliver the formulation in an appropriate manner.

The following formulation examples illustrate representative pharmaceutical compositions of the present invention. Amount of a compound of present invention in a formulation composition can be in a range of 10-10000 mg. Preferably, said amount can be in a range of 20-900 mg. More preferably, said amount can be in a range of 50-750 mg, or even more preferably, in a range of 200-600 mg.

Formulation Example 1

Hard gelatin capsules containing the following ingredients are prepared:

| Ingredient | Quantity (mg/capsule) |
| --- | --- |
| Active Ingredient | 200-600 |
| Starch | 100-300 |
| Magnesium stearate | 5-15 |

The above ingredients are mixed and filled into hard gelatin capsules for oral administration.

Formulation Example 2

A tablet formula is prepared using the ingredients below:

| Ingredient | Quantity (mg/tablet) |
| --- | --- |
| Active Ingredient | 50-750 |
| Cellulose, microcrystalline | 100-250 |
| Colloidal silicon dioxide | 10-20 |
| Stearic acid | 5-10 |

The components are blended and compressed to form tablets for oral administration.

Formulation Example 3

A dry powder inhaler formulation is prepared containing the following components:

| Ingredient | Weight % |
| --- | --- |
| Active Ingredient | 100-600 |
| Lactose | 40-100 |

The active ingredient is mixed with the lactose and the mixture is added to a dry powder inhaling appliance.

Formulation Example 4

Tablets, each containing 200-600 mg of active ingredient, are prepared as follows

| Ingredient | Quantity (mg/tablet) |
| --- | --- |
| Active Ingredient | 200-600 mg |
| Starch | 15-45 mg |
| Microcrystalline cellulose | 10-35 mg |
| Polyvinylpyrrolidone (as 10% solution in sterile water) | 5-10 mg |
| Sodium carboxymethyl starch | 5-10 mg |
| Magnesium stearate | 0.5-2 mg |
| Talc | 1.0-5 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets for oral administration.

Formulation Example 5

Capsules, each containing 200-600 mg of medicament are made as follows:

| Ingredient | Quantity (mg/capsule) |
| --- | --- |
| Active Ingredient | 200-600 mg |
| Starch | 75-150 mg |
| Magnesium stearate | 1-4 mg |

The active ingredient, starch and magnesium stearate are blended, passed through a No. 20 mesh U.S. sieve, and filled into hard gelatin capsules for oral administration.

Formulation Example 6

Suppositories, each containing 200-600 mg of active ingredient are made as follows:

| Ingredient | Amount |
| --- | --- |
| Active Ingredient | 200-600 mg |
| Saturated fatty acid glycerides to | 1000-2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 200-600 mg of medicament per 7 mL dose are made as follows:

| Ingredient | Amount |
| --- | --- |
| Active Ingredient | 200-600 mg |
| Xanthan gum | 2-8 mg |
| Sodium carboxymethyl cellulose (11%) Microcrystalline cellulose (89%) | 20-50 mg |
| Sucrose | 1.0-1.75 g |
| Sodium benzoate | 10-20 mg |

-continued

| Ingredient | Amount |
|---|---|
| Flavor and Color | q.v. |
| Purified water to | 5-7 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
|---|---|
| Active Ingredient | 200-600 mg |
| Starch | 200-410 mg |
| Magnesium stearate | 3-6 mg |

The active ingredient, starch, and magnesium stearate are blended, passed through a No. 20 mesh U.S. sieve, and filled into hard gelatin capsules for oral administration.

Formulation Example 9

A subcutaneous formulation may be prepared as follows:

| Ingredient | Quantity |
|---|---|
| Active Ingredient | 200-600 mg |
| Corn Oil | 1.0-1.5 mL |

Formulation Example 10

A topical formulation may be prepared as follows:

| Ingredient | Quantity |
|---|---|
| Active Ingredient | 1-10 g |
| Emulsifying Wax | 20-30 g |
| Liquid Paraffin | 10-20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions that can transiently open the blood-brain barrier.

Other suitable formulations for use in the present invention can be found in Remington's Pharmaceutical Sciences, Mace Publishing Company, Philadelphia, Pa., 17th ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

The disclosures of each and every patent, patent application and publication (for example, journals, articles and/or textbooks) cited herein are hereby incorporated by reference in their entirety. Also, as used herein and in the appended claims, singular articles such as "a", "an" and "one" are intended to refer to singular or plural. While the present invention has been described herein in conjunction with a preferred aspect, a person with ordinary skills in the art, after reading the foregoing specification, can affect changes, substitutions of equivalents and other types of alterations to the invention as set forth herein. Each aspect described above can also have included or incorporated therewith such variations or aspects as disclosed in regard to any or all of the other aspects. The present invention is also not to be limited in terms of the particular aspects described herein, which are intended as single illustrations of individual aspects of the invention. Many modifications and variations of this invention can be made without departing from its spirit and scope, as will be apparent to those skilled in the art. Functionally equivalent methods within the scope of this invention, in addition to those enumerated herein, will be apparent to those skilled in the art from the foregoing descriptions. It is to be understood that this invention is not limited to particular methods, reagents, process conditions, materials and so forth, which can, of course, vary. It is also to be understood that the terminology used herein is for the purpose of describing particular aspects only, and is not intended to be limiting. Thus, it is intended that the specification be considered as exemplary.

What is claimed is:

1. A compound according to formula II:

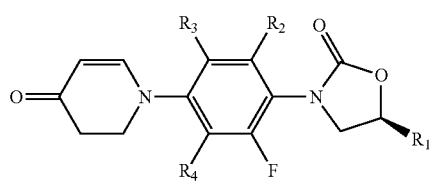

or a pharmaceutically acceptable salt thereof
wherein $R^1$ is (1,2,3-triazol-1-yl)methyl or isoxazol-3-yl) aminomethyl;
$R^2$ is H; and
$R^3$ and $R^4$ are each F.

2. The compound of claim 1, according to the following formula:

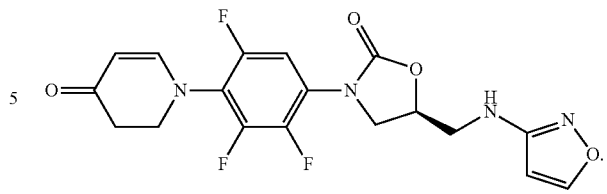

3. A method for the treatment of a bacterial infection in a mammal comprising administering to the mammal in need thereof a therapeutically effective amount of a compound of claim 1.

4. The method according to claim 3, wherein the compound is administered to the mammal orally, parenterally, transdermally, topically, rectally, or intranasally in a pharmaceutical composition.

5. The method according to claim 3, wherein the compound is administered once-daily in an amount of from about 1 to about 75 mg/kg of body weight/day.

6. The method according to claim 3, wherein the bacterial infection is a gram-positive microbial infection.

7. A pharmaceutical composition comprising a therapeutically effective amount of a compound of claim 1 and a pharmaceutically acceptable carrier.

* * * * *